(12) United States Patent
Policker et al.

(10) Patent No.: US 8,301,256 B2
(45) Date of Patent: Oct. 30, 2012

(54) GI LEAD IMPLANTATION

(75) Inventors: Shai Policker, Tenafly, NJ (US); David Prutchi, Voorhees, NJ (US); Ophir Bitton, Voorhees, NJ (US); Benny Rousso, Rishon le Zion (IL); Offer Glasberg, Zichron Yakov (IL); Yuval Mika, Closter, NJ (US); Tami Harel, Haifa (IL); Walid Haddad, Closter, NJ (US); Lena Milman, Haifa (IL)

(73) Assignee: Metacure Limited, Hamilton (BM)

( * ) Notice: Subject to any disclaimer, the term of this patent is extended or adjusted under 35 U.S.C. 154(b) by 917 days.

(21) Appl. No.: 11/915,647

(22) PCT Filed: Jun. 4, 2006

(86) PCT No.: PCT/IL2006/000644
§ 371 (c)(1),
(2), (4) Date: Nov. 12, 2008

(87) PCT Pub. No.: WO2006/129321
PCT Pub. Date: Dec. 7, 2006

(65) Prior Publication Data
US 2009/0204063 A1    Aug. 13, 2009

Related U.S. Application Data

(63) Continuation-in-part of application No. PCT/US2006/010911, filed on Mar. 24, 2006.

(60) Provisional application No. 60/687,099, filed on Jun. 2, 2005.

(51) Int. Cl.
*A61N 1/00*    (2006.01)

(52) U.S. Cl. .......................................................... 607/40
(58) Field of Classification Search ..................... 607/40
See application file for complete search history.

(56) References Cited

U.S. PATENT DOCUMENTS

| | | |
|---|---|---|
| 3,411,507 A | 11/1968 | Wingrove |
| 3,516,412 A | 6/1970 | Ackerman |
| 3,737,579 A | 6/1973 | Bolduc |
| 4,000,745 A | 1/1977 | Goldberg et al. |
| 4,010,758 A | 3/1977 | Rockland et al. |
| 4,133,315 A | 1/1979 | Berman et al. |
| 4,177,818 A | 12/1979 | De Pedro |

(Continued)

FOREIGN PATENT DOCUMENTS

| | | |
|---|---|---|
| EP | 0057048 | 8/1982 |

(Continued)

OTHER PUBLICATIONS

Jaremko, et al., "Advances toward the implantable artificial pancreas for treatment of diabetes", Diabetes Care, 21(3), Mar. 1998.

(Continued)

*Primary Examiner* — Niketa Patel
*Assistant Examiner* — William Levicky
(74) *Attorney, Agent, or Firm* — William G. Dippert; Eckert Seamans Cherin & Mellot, LLC

(57) ABSTRACT

A method is provided, including physically contacting a gastric implantation site of a stomach via a transluminal approach, physically contacting the site via a transabdominal approach, stabilizing the site, and implanting an electrode at the site based on the physical contact provided by the transluminal and transabdominal approach. Other embodiments are also described.

12 Claims, 20 Drawing Sheets

U.S. PATENT DOCUMENTS

| | | | |
|---|---|---|---|
| 4,235,246 A | 11/1980 | Weiss |
| 4,280,503 A | 7/1981 | Ackerman |
| 4,313,448 A | 2/1982 | Stokes |
| 4,357,946 A | 11/1982 | Dutcher et al. |
| 4,369,791 A | 1/1983 | Friedman |
| 4,378,023 A | 3/1983 | Trabucco |
| 4,416,267 A | 11/1983 | Garren et al. |
| 4,452,254 A | 6/1984 | Goldberg et al. |
| 4,485,805 A | 12/1984 | Foster, Jr. |
| 4,592,339 A | 6/1986 | Kuzmak |
| 4,717,581 A | 1/1988 | Robblee |
| 4,823,808 A | 4/1989 | Clegg et al. |
| 4,975,682 A | 12/1990 | Kerr et al. |
| 5,074,868 A | 12/1991 | Kuzmak |
| 5,101,814 A | 4/1992 | Palti |
| 5,103,804 A | 4/1992 | Abel et al. |
| 5,105,812 A | 4/1992 | Corman |
| 5,188,104 A | 2/1993 | Wernicke et al. |
| 5,190,041 A | 3/1993 | Palti |
| 5,226,429 A | 7/1993 | Kuzmak |
| 5,234,454 A | 8/1993 | Bangs |
| 5,247,938 A | 9/1993 | Silverstein et al. |
| 5,263,480 A | 11/1993 | Wernicke et al. |
| 5,292,344 A | 3/1994 | Douglas |
| 5,314,461 A | 5/1994 | Borghi |
| 5,314,463 A | 5/1994 | Camps et al. |
| 5,368,028 A | 11/1994 | Palti |
| 5,423,872 A | 6/1995 | Cigaina |
| 5,449,368 A | 9/1995 | Kuzmak |
| 5,514,175 A | 5/1996 | Kim et al. |
| 5,540,730 A | 7/1996 | Terry et al. |
| 5,551,425 A | 9/1996 | Essen-Moller |
| 5,601,604 A | 2/1997 | Vincent |
| 5,654,030 A | 8/1997 | Munshi et al. |
| 5,690,691 A | 11/1997 | Chen et al. |
| 5,704,368 A | 1/1998 | Asano et al. |
| 5,716,385 A | 2/1998 | Mittal et al. |
| 5,741,211 A | 4/1998 | Renirie et al. |
| 5,792,210 A | 8/1998 | Wamubu et al. |
| 5,795,304 A | 8/1998 | Sun et al. |
| 5,836,994 A | 11/1998 | Bourgeois |
| 5,837,006 A | 11/1998 | Ocel et al. |
| 5,861,014 A | 1/1999 | Familoni |
| 5,868,141 A | 2/1999 | Ellias |
| 5,919,216 A | 7/1999 | Houben et al. |
| 5,938,669 A | 8/1999 | Klaiber et al. |
| 5,979,449 A | 11/1999 | Steer |
| 5,991,649 A | 11/1999 | Garfield et al. |
| 5,995,872 A | 11/1999 | Bourgeois |
| 6,026,326 A | 2/2000 | Bardy |
| 6,041,258 A | 3/2000 | Cigaina et al. |
| 6,067,991 A | 5/2000 | Forsell |
| 6,083,249 A | 7/2000 | Familoni |
| 6,091,992 A | 7/2000 | Bourgeois |
| 6,092,528 A | 7/2000 | Edwards |
| 6,093,167 A | 7/2000 | Houben et al. |
| 6,104,955 A | 8/2000 | Bourgeois |
| 6,115,635 A | 9/2000 | Bourgeois |
| 6,129,685 A | 10/2000 | Howard |
| 6,132,372 A | 10/2000 | Essen-Moller |
| 6,135,978 A | 10/2000 | Houben |
| 6,185,452 B1 | 2/2001 | Schulman et al. |
| 6,216,045 B1 | 4/2001 | Black et al. |
| 6,243,607 B1 | 6/2001 | Mintchev |
| 6,249,697 B1 | 6/2001 | Asano et al. |
| 6,261,280 B1 | 7/2001 | Houben et al. |
| 6,270,455 B1 | 8/2001 | Brown |
| 6,321,124 B1 | 11/2001 | Cigaina |
| 6,334,073 B1 | 12/2001 | Levine |
| 6,363,937 B1 | 4/2002 | Hovda et al. |
| 6,381,495 B1 | 4/2002 | Jenkins |
| 6,405,732 B1 | 6/2002 | Edwards |
| 6,411,842 B1 | 6/2002 | Cigaina et al. |
| 6,415,178 B1 | 7/2002 | Ben-Haim et al. |
| 6,427,089 B1 | 7/2002 | Knowlton |
| 6,449,511 B1 | 9/2002 | Mintchev |
| 6,454,699 B1 | 9/2002 | Forsell |
| 6,477,423 B1 | 11/2002 | Jenkins |
| 6,510,332 B1 | 1/2003 | Greenstein |
| 6,516,227 B1 | 2/2003 | Meadows et al. |
| 6,535,764 B2 | 3/2003 | Imran et al. |
| 6,571,127 B1 | 5/2003 | Ben-Haim et al. |
| 6,572,542 B1 | 6/2003 | Houben et al. |
| 6,584,348 B2 | 6/2003 | Glukhovsky |
| 6,591,137 B1 | 7/2003 | Fischell et al. |
| 6,600,953 B2 | 7/2003 | Flesler et al. |
| 6,606,523 B1 | 8/2003 | Jenkins |
| 6,609,025 B2 | 8/2003 | Barrett et al. |
| 6,612,983 B1 | 9/2003 | Marchal |
| 6,652,444 B1 | 11/2003 | Ross |
| 6,658,297 B2 | 12/2003 | Loeb |
| 6,684,104 B2 | 1/2004 | Gordon |
| 6,735,477 B2 | 5/2004 | Levine |
| 6,745,079 B2 | 6/2004 | King |
| 6,754,536 B2 | 6/2004 | Swoyer et al. |
| 6,826,428 B1 | 11/2004 | Chen et al. |
| 6,832,114 B1 | 12/2004 | Whitehurst |
| 6,852,110 B2 | 2/2005 | Roy et al. |
| 6,853,862 B1 | 2/2005 | Marchal et al. |
| 6,869,431 B2 | 3/2005 | Maguire et al. |
| 6,876,885 B2 | 4/2005 | Swoyer et al. |
| 6,895,279 B2 | 5/2005 | Loeb et al. |
| 6,918,871 B2 | 7/2005 | Schulze |
| 6,918,906 B2 | 7/2005 | Long |
| 6,939,349 B2 | 9/2005 | Fleischman et al. |
| 6,947,792 B2 | 9/2005 | Ben-Haim et al. |
| 6,952,613 B2 | 10/2005 | Swoyer et al. |
| 7,006,871 B1 | 2/2006 | Darvish et al. |
| 7,016,735 B2 | 3/2006 | Imran et al. |
| 7,043,295 B2 | 5/2006 | Starkebaum |
| 7,054,690 B2 | 5/2006 | Imran |
| 7,076,305 B2 | 7/2006 | Imran et al. |
| 7,076,306 B2 | 7/2006 | Marchal et al. |
| 2001/0011543 A1 | 8/2001 | Forsell |
| 2002/0026141 A1 | 2/2002 | Houben |
| 2002/0103424 A1 | 8/2002 | Swoyer et al. |
| 2002/0161414 A1 | 10/2002 | Flesler et al. |
| 2002/0165589 A1 | 11/2002 | Imran et al. |
| 2003/0045919 A1 | 3/2003 | Swoyer et al. |
| 2003/0055464 A1 | 3/2003 | Darvish et al. |
| 2003/0055467 A1 | 3/2003 | Ben-Haim et al. |
| 2003/0066536 A1 | 4/2003 | Forsell |
| 2003/0114899 A1 | 6/2003 | Woods et al. |
| 2003/0135091 A1* | 7/2003 | Nakazawa et al. ............ 600/113 |
| 2003/0144708 A1 | 7/2003 | Starkebaum |
| 2003/0195600 A1 | 10/2003 | Tronnes et al. |
| 2003/0208212 A1 | 11/2003 | Cigaina |
| 2003/0208242 A1 | 11/2003 | Harel et al. |
| 2003/0220678 A1 | 11/2003 | Tronnes et al. |
| 2004/0044376 A1 | 3/2004 | Flesler et al. |
| 2004/0059393 A1 | 3/2004 | Policker et al. |
| 2004/0088023 A1* | 5/2004 | Imran et al. .................. 607/40 |
| 2004/0098068 A1 | 5/2004 | Carbunaru et al. |
| 2004/0106963 A1 | 6/2004 | Tsukamoto et al. |
| 2004/0107004 A1 | 6/2004 | Levine et al. |
| 2004/0147816 A1 | 7/2004 | Policker et al. |
| 2004/0158138 A1 | 8/2004 | Kilcoyne et al. |
| 2004/0162469 A1 | 8/2004 | Imran |
| 2004/0162595 A1 | 8/2004 | Foley |
| 2004/0167583 A1 | 8/2004 | Knudson et al. |
| 2004/0193184 A1 | 9/2004 | Laufer et al. |
| 2004/0236316 A1 | 11/2004 | Danitz et al. |
| 2004/0243195 A1 | 12/2004 | Imran et al. |
| 2004/0243211 A1 | 12/2004 | Colliou et al. |
| 2004/0249421 A1 | 12/2004 | Harel et al. |
| 2005/0021101 A1 | 1/2005 | Chen et al. |
| 2005/0055038 A1 | 3/2005 | Kelleher et al. |
| 2005/0065505 A1 | 3/2005 | Ryan |
| 2005/0075654 A1 | 4/2005 | Kelleher |
| 2005/0090873 A1 | 4/2005 | Imran |
| 2005/0107829 A1 | 5/2005 | Edwards et al. |
| 2005/0143784 A1 | 6/2005 | Imran |
| 2005/0164925 A1 | 7/2005 | Jakubowski et al. |
| 2005/0183732 A1 | 8/2005 | Edwards |
| 2005/0192615 A1 | 9/2005 | Torre et al. |
| 2005/0203500 A1 | 9/2005 | Saadat |
| 2005/0209653 A1 | 9/2005 | Herbert et al. |

| | | | |
|---|---|---|---|
| 2005/0222638 | A1 | 10/2005 | Foley et al. |
| 2005/0251219 | A1 | 11/2005 | Evans |
| 2006/0074459 | A1 | 4/2006 | Flesler et al. |
| 2006/0085045 | A1 | 4/2006 | Harel et al. |
| 2006/0089690 | A1 | 4/2006 | Gerber |
| 2006/0142803 | A1 | 6/2006 | Mintchev |
| 2006/0173238 | A1 | 8/2006 | Starkebaum |
| 2006/0184207 | A1 | 8/2006 | Darvish et al. |
| 2006/0247718 | A1 | 11/2006 | Starkebaum |
| 2007/0006081 | A1 | 1/2007 | Harel et al. |
| 2007/0027493 | A1 | 2/2007 | Ben-Haim et al. |
| 2007/0051849 | A1 | 3/2007 | Watts et al. |
| 2007/0060971 | A1 | 3/2007 | Glasberg et al. |
| 2007/0092446 | A1 | 4/2007 | Haddad et al. |
| 2007/0156177 | A1 | 7/2007 | Harel et al. |
| 2007/0179556 | A1 | 8/2007 | Ben-Haim et al. |
| 2007/0185540 | A1 | 8/2007 | Ben-Haim et al. |
| 2007/0299320 | A1 | 12/2007 | Policker et al. |
| 2008/0046062 | A1 | 2/2008 | Camps et al. |
| 2008/0058889 | A1 | 3/2008 | Ben-Haim et al. |
| 2008/0058891 | A1 | 3/2008 | Ben-Haim et al. |
| 2008/0065168 | A1 | 3/2008 | Bitton et al. |
| 2008/0178684 | A1 | 7/2008 | Spehr |
| 2009/0062893 | A1 | 3/2009 | Spehr |
| 2009/0088816 | A1 | 4/2009 | Harel et al. |
| 2009/0118797 | A1 | 5/2009 | Kliger et al. |
| 2009/0131993 | A1 | 5/2009 | Rousso et al. |
| 2009/0204063 | A1 | 8/2009 | Policker et al. |
| 2009/0281449 | A1 | 11/2009 | Thrower et al. |
| 2010/0228105 | A1 | 9/2010 | Policker et al. |
| 2010/0305468 | A1 | 12/2010 | Policker et al. |
| 2010/0324644 | A1 | 12/2010 | Levi et al. |

FOREIGN PATENT DOCUMENTS

| | | |
|---|---|---|
| EP | 0129483 | 12/1984 |
| EP | 1036545 | 9/2000 |
| EP | 1 447 052 | 8/2004 |
| JP | 2003/319945 | 11/2003 |
| WO | WO 2004/112883 | 9/1978 |
| WO | WO 94/01172 | 1/1994 |
| WO | WO 97/25098 | 7/1997 |
| WO | WO 98/10830 | 3/1998 |
| WO | WO 01/10375 | 5/1998 |
| WO | WO 99/03533 | 1/1999 |
| WO | WO 2006/097934 | 8/2000 |
| WO | WO 00/53257 | 9/2000 |
| WO | WO 01/41671 | 6/2001 |
| WO | WO 01/66183 | 9/2001 |
| WO | WO 01/83019 | 11/2001 |
| WO | WO 01/91854 | 12/2001 |
| WO | WO 02/053093 | 7/2002 |
| WO | WO 02/082968 | 10/2002 |
| WO | WO 02/089655 | 11/2002 |
| WO | WO 03/020365 | 3/2003 |
| WO | WO 03/045493 | 6/2003 |
| WO | WO 2004/021858 | 3/2004 |
| WO | WO 2004/043280 | 5/2004 |
| WO | WO 2004/066903 | 8/2004 |
| WO | WO 2004/069330 | 8/2004 |
| WO | WO 2004/091361 | 10/2004 |
| WO | WO 2004/096337 | 11/2004 |
| WO | WO 2004/112563 | 12/2004 |
| WO | WO 2005/007232 | 1/2005 |
| WO | WO 2005/007237 | 1/2005 |
| WO | WO 2005/009288 | 2/2005 |
| WO | WO 2005/016181 | 2/2005 |
| WO | WO 2005/023081 | 3/2005 |
| WO | WO 2005/037152 | 4/2005 |
| WO | WO 2005/041749 | 5/2005 |
| WO | WO 2005/087310 | 9/2005 |
| WO | WO 2006/018851 | 2/2006 |
| WO | WO 2006/035446 | 4/2006 |
| WO | WO 2006/087712 | 8/2006 |
| WO | WO 2006/087717 | 8/2006 |
| WO | WO 2006/102626 | 9/2006 |
| WO | WO 2006/129321 | 9/2006 |
| WO | WO 2006/045075 | 10/2006 |
| WO | WO 2006/118790 | 11/2006 |
| WO | WO 2007/080595 | 7/2007 |
| WO | WO 2008/117296 | 10/2008 |
| WO | WO 2008/139463 | 11/2008 |
| WO | WO 2011/092710 | 8/2011 |

OTHER PUBLICATIONS

Lamb F.S. et al., "Cyclosporine augments reactivity of isolated blood vessels", Life Sciences, 40, pp. 2571-2578, 1987.

Johansson B. et al., "Static and dynamic components in the vascular myogenic response to passive changes in length as revealed by electrical and mechanical recordings from the rat portal vein", Circulation Research, 36, pp. 76-83, 1975.

Zelcer E. et al., "Spontaneous electrical activity in pressurized small mesenteric arteries", Blood Vessels, 19, pp. 301-310, 1982.

Schobel H.P. et al., "Preeclampsia—a state of sympathetic overactivity", New England Journal of Medicine, 335, pp. 148-1485, 1996.

Rosenpire A.J. et al., "Pulsed DC Electric Fields Couple to Natural NAD(P)H Oscillations in HT-1080 Fibrosarcoma Cells", Journal of Cell Science, 114(Pt. 8), pp. 1515-1520, Apr. 2001.

Gomis A. et al., "Oscillatory patterns of electrical activity in mouse pancreatic islets of Langerhans recorded in vivo", Pflugers Archiv European Journal of Physiology, Abstract vol. 432(3), pp. 510-515, 1996.

Soria B. et al., "Cytosolic calcium oscillations and insulin release in pancreatic islets of Langerhans", Diabetes Metab., 24(1), pp. 37-40, Feb. 1998.

Magnus G. et al., "Model of Beta-cell mitochondrial calcium handling and electrical activity. II. Mitochondrial variables", American Journal of Physiology, 274(4 Pt 1): C1174-1184, Apr. 1998.

Yamada, "Effects of drugs on electromechanical activities of the stomach and duodenum of conscious dogs", Nippon Heikatsukin Gakkai Zasshi. Feb. 1983;19(1):25-35. (abstract only).

Nadal A. et al., "Homologous and heterologous asynchronicity between identified alpha-, beta-, and delta-cells within intact islets of Langerhans in the mouse", Journal of Physiology, 517(Pt. 1), pp. 85-93, May 1999.

M D Robertson, et al, "The influence of the colon on postprandial glucagons-like peptide 1 (7-36) amide concentration in man", Journal of Endocrinology (1999) 161, 25-31.

J Schirra, et al, "Mechanisms of the antidiabetic action of subcutaneous glucagons-like peptide-1 (7-36) amide in non-insulin dependent diabetes mellitus", Journal of Endocrinology (1998) 156, 177-186.

T Vilsboll and Associates, Research design and methods, Diabetes, vol. 50, Mar. 2001, pp. 610-613.

Jeannie F. Todd, et al, "Subcutaneous glucagons-like peptide-1 improves postprandial glycaemic control over 3-week period in patients with early type 2 diabetes", Clinical Science (1998) 95, 325-329.

Daniel J. Drucker, "Development of glucagon-like peptide-1-based pharmaceuticals as therapeutic agents for the treatment of diabetes", Current Pharmaceutical Design, 2001, 7, 1399-1412.

Shemerovskii KA, "Effect of feeding on the activity of duodenal smooth muscle in dogs", Biull Eksp Biol Med. Oct. 1978;86(10):394-7. (Abstract only).

Swain et al., in "An endoscopically deliverable tissue-transfixing device for securing biosensors in the gastrointestinal tract", Gastrointestinal Endoscopy 40(6): 730-734 (1994).

Kalloo AN et al. (2004) Flexible transgastric peritoneoscopy: a novel approach to diagnostic and therapeutic interventions. Gastrointest Endosc 60: 114- 117.

Park PO et al. (2005) Experimental studies of transgastric gall bladder surgery: cholecystectomy and cholecystogastric anastomosis. Gastrointest Endosc 61: 601-606.

Kantsevoy SV et al. (2006) Transgastric endoscopic splenectomy: Is it possible? Surg Endosc 20:522-526.

Rattner D, Kalloo A, et al. (2006) White Paper: ASGE/SAGES Working Group on Natural Orifice Transluminal Endoscopic Surgery. Surg Endosc 20:329-333.

Stein et al., "Carrots and sticks: Impact of an incentive/disincentive employee flexible credit benefit plan on health status and medical costs", American Journal of Health Promotion, May/Jun. 1999, V5, I13, 5.

Giuffrida, "Should we pay the patient? Review of financial incentives to enhance patient compliance", Biomedical Journal, vol. 315, pp. 703-707, 1997.

An abstract entitled "Gastric myoelectrical pacing as therapy for morbid obesity: Preliminary results", by Cigaina, et al., Dec. 24, 2000.

An abstract entitled "Implantable gastric stimulator (IGS) as therapy for morbid obesity: Equipment, surgical technique and stimulation parameters", by Cigaina, et al., Dec. 24, 2000.

Quesada, et al—"Different Effects of Tolbutermide . . . ", Diabetes, vol. 48, Dec. 1999, pp. 2390-2397.

Kim, et al—"Development and Characterization . . . ", Diabetes, vol. 52, Mar. 2003, pp. 751-759.

EPO Communication dated Oct. 24, 2008 issued to Metacure—Appln. No. 02 724 592.7-2305.

EPO Communication dated Apr. 7, 2009 issued to Metacure—Appln. No. 06748690.2-2305 / 1861160.

An Office Action dated Oct. 24, 2008, which issued during the prosecution of Applicant's European Patent Application No. EP 02 724 592.7.

An Examination Report dated Apr. 7, 2009, which issued during the prosecution of Applicant's European Patent Application No. EP 06 74 8690.

International Search Report and The Written Opinion Dated Sep. 2, 2011 From the International Searching Authority Re. Application No. PCT/IL 11/00116.

\* cited by examiner

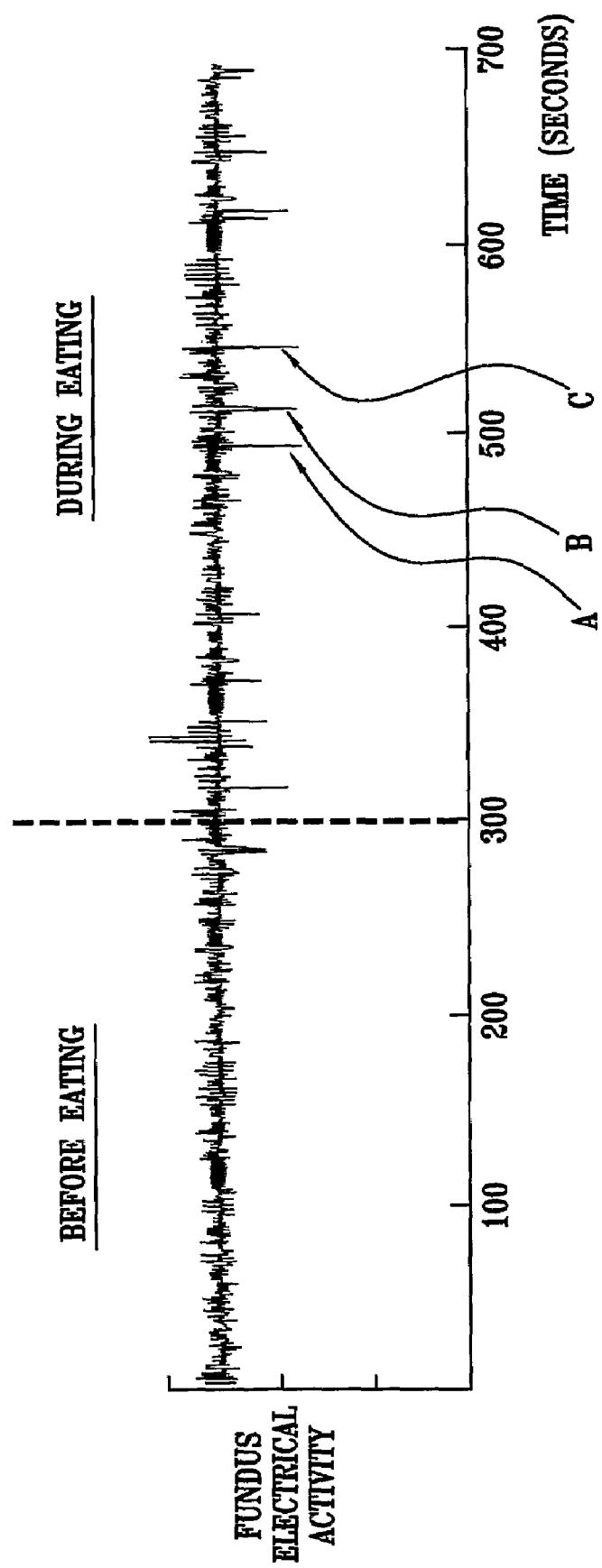

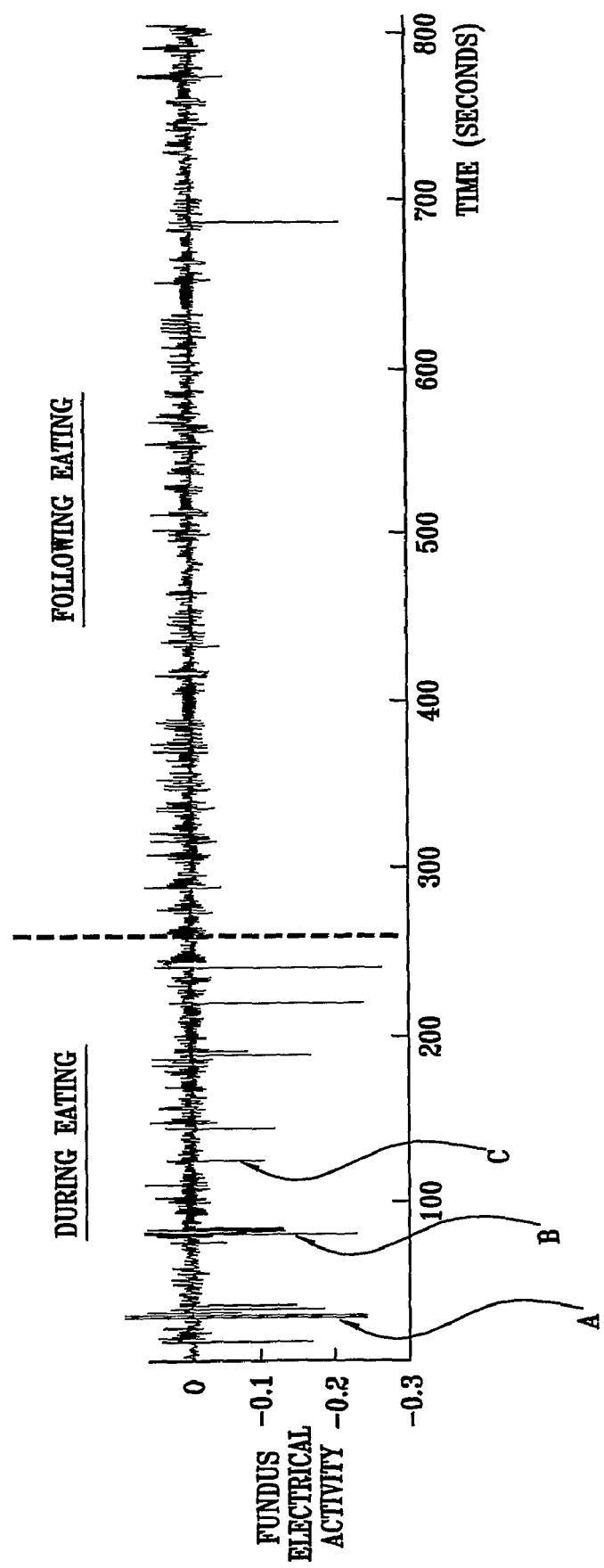

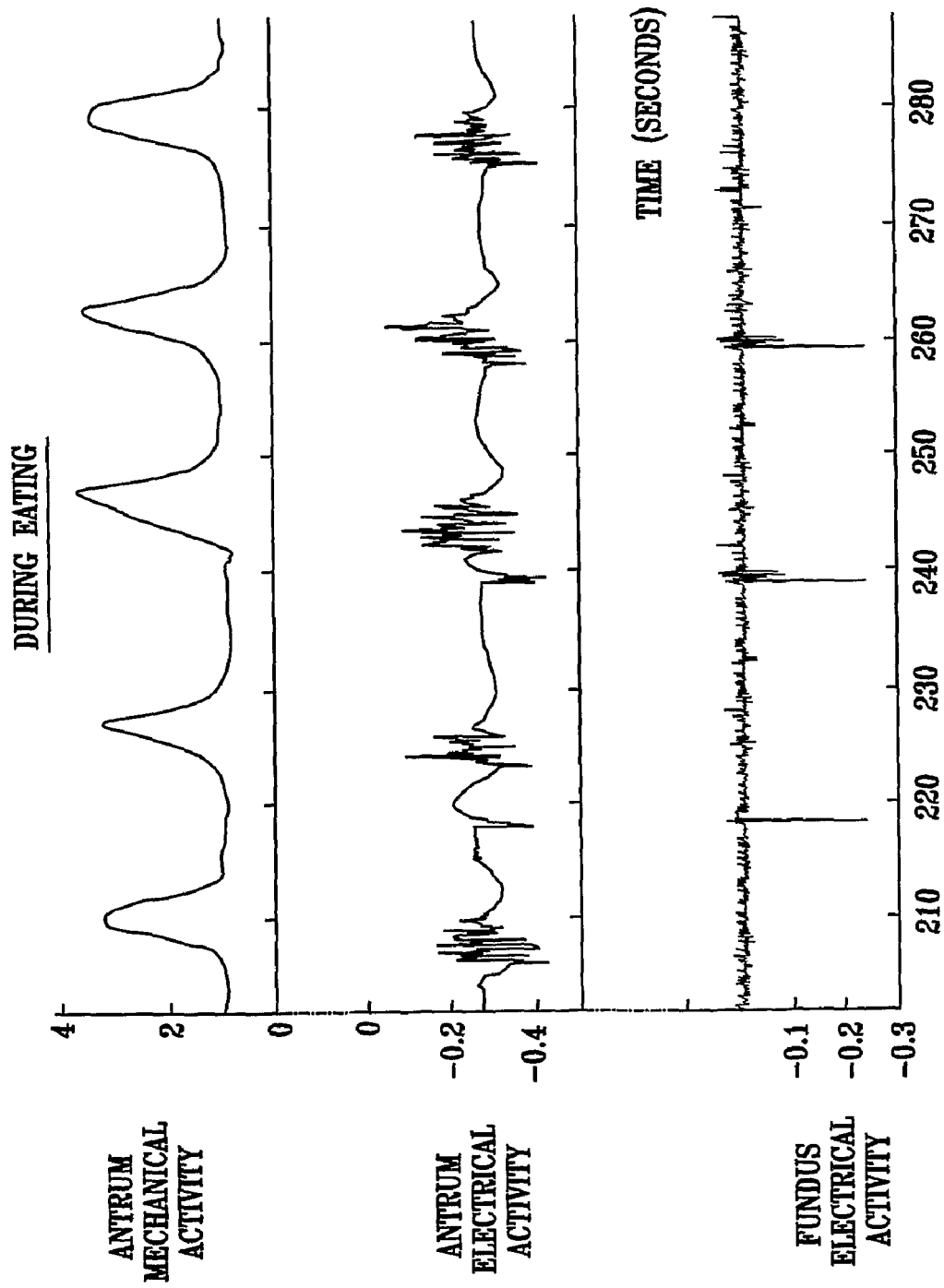

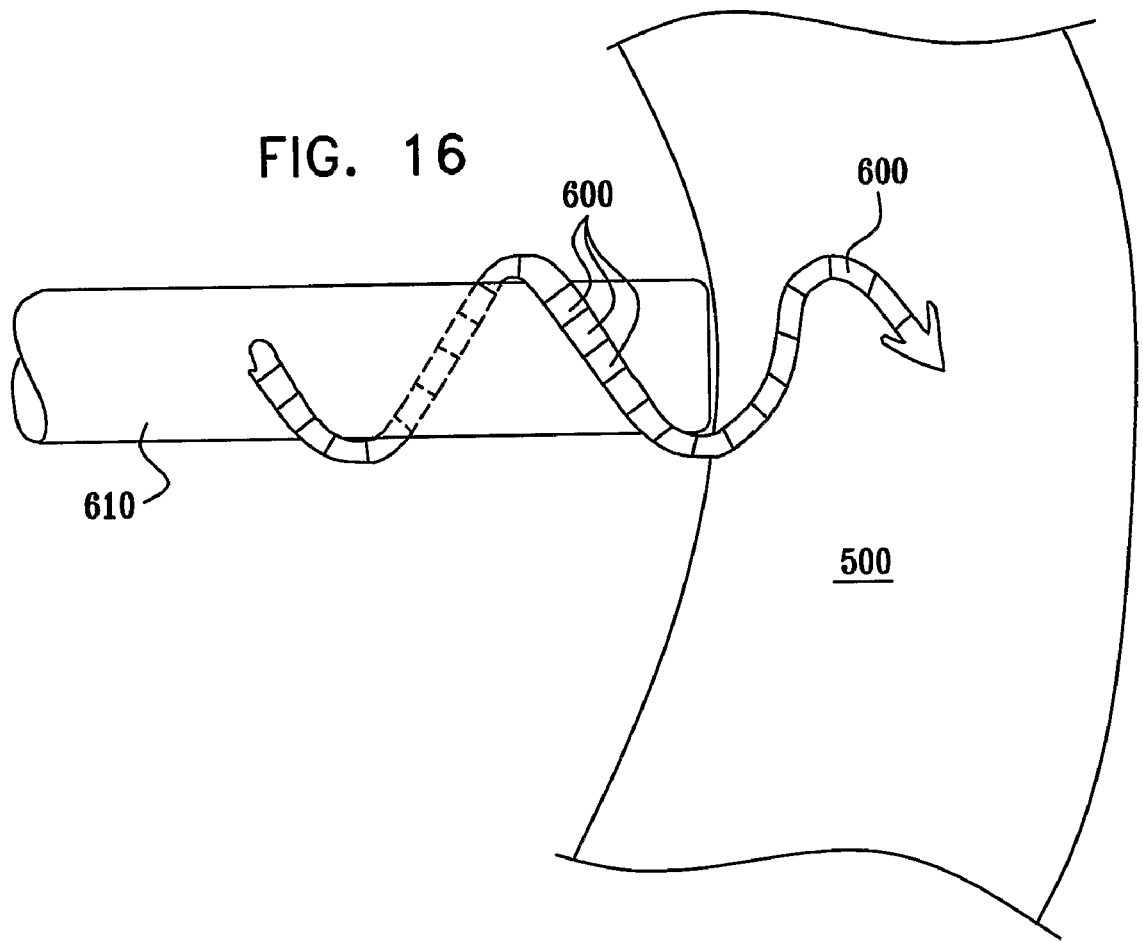

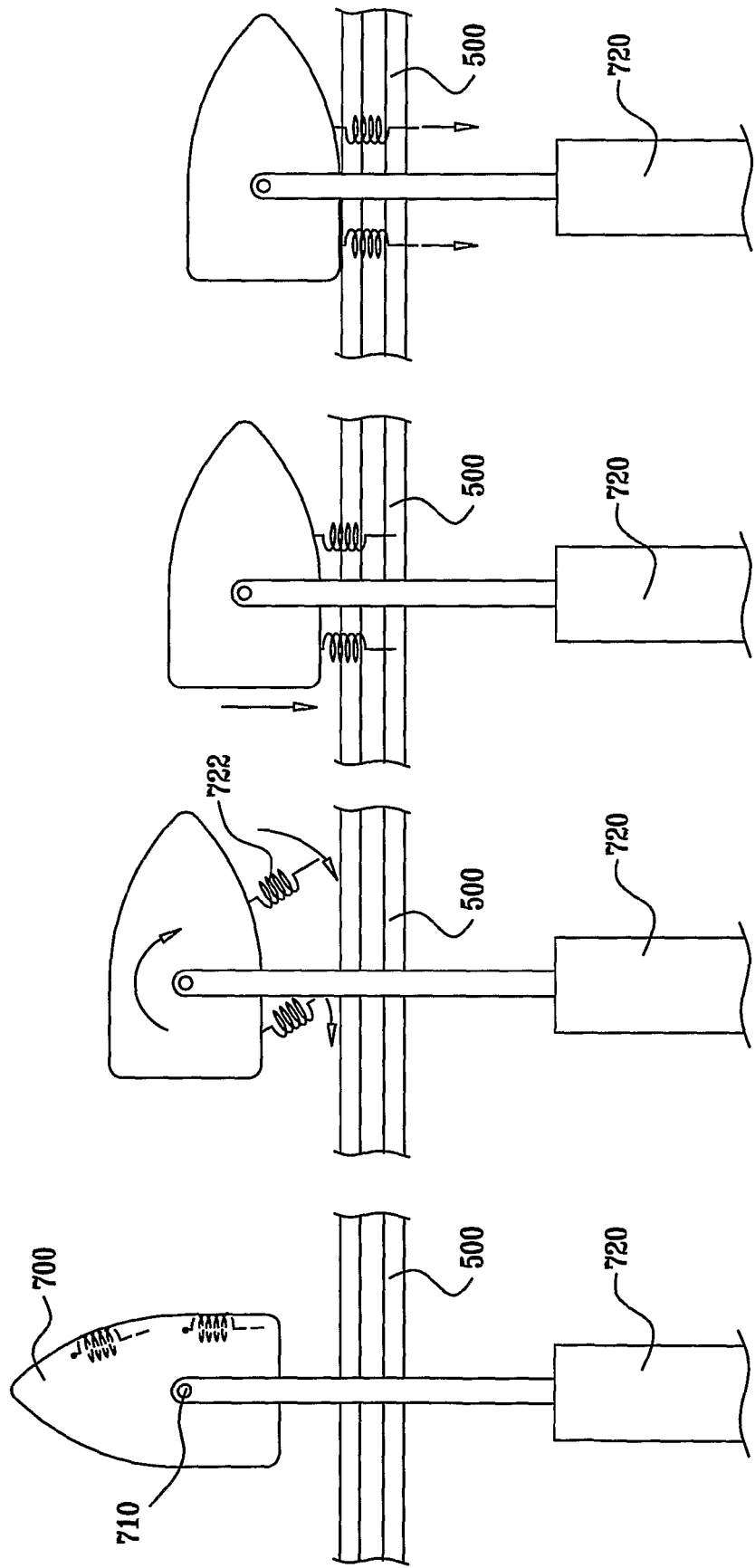

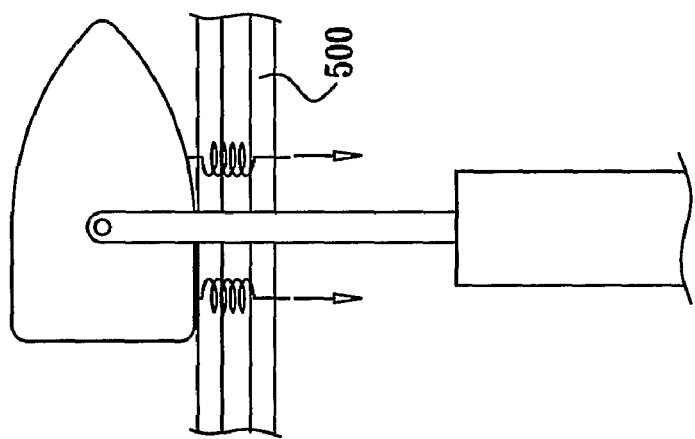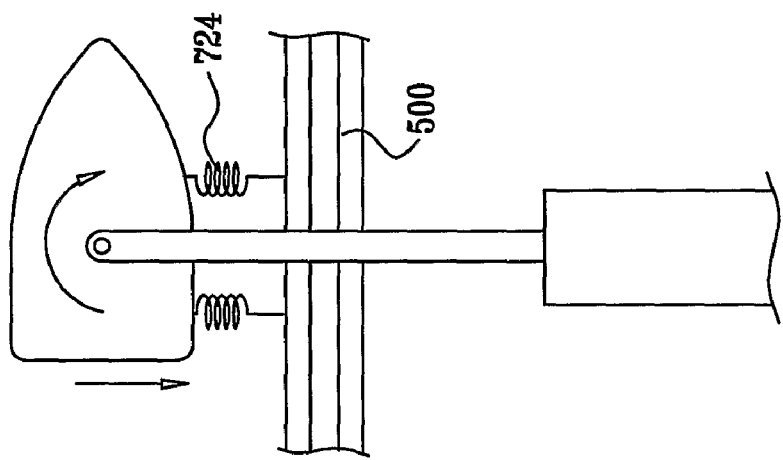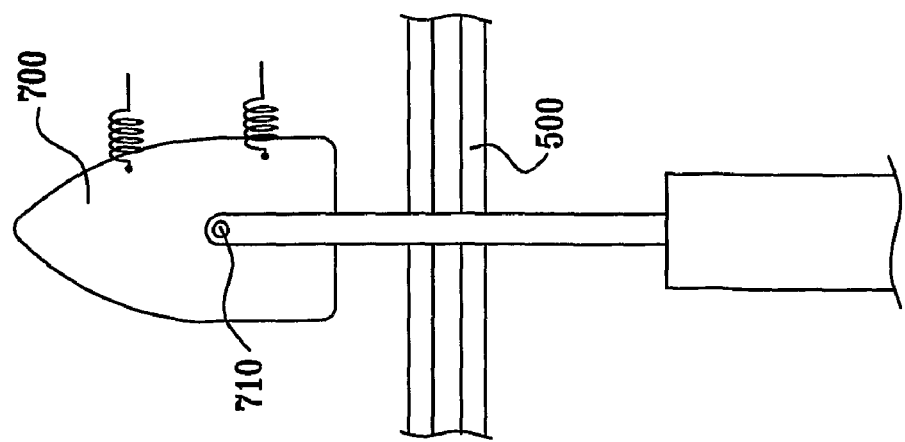

GI LEAD IMPLANTATION

CROSS-REFERENCES TO RELATED APPLICATIONS

The present patent application:

(a) claims priority from U.S. Provisional Patent Application 60/687,099 to Mika et al., filed Jun. 2, 2005, entitled, "Endoscopic implantation of gastric leads," and (b) is a continuation-in-part of PCT Patent Application PCT/US2006/010911 to Policker et al., filed Mar. 24, 2006, entitled, "Wireless leads for gastrointestinal tract applications," which claims priority from U.S. Provisional Patent Application 60/665,320 to Policker et al., filed Mar. 24, 2005.

All of the above-cited applications are assigned to the assignee of the present patent application and are incorporated herein by reference.

FIELD OF THE INVENTION

The present invention relates generally to tracking eating habits, and specifically to invasive techniques and apparatus for detecting and analyzing the swallowing and digesting of food.

BACKGROUND OF THE INVENTION

Obesity is a difficult to treat chronic condition defined by a body mass index (BMI=mass/height$^2$ [kg/m$^2$]) greater than 30. For obese persons, excessive weight is commonly associated with increased risk of cardiovascular disease, diabetes, degenerative arthritis, endocrine and pulmonary abnormalities, gallbladder disease and hypertension. Additionally, such persons are highly likely to experience psychological difficulties because of lifestyle restrictions such as reduced mobility and physical capacity, due to back pain, joint problems, and shortness of breath. In severe cases, this can contribute to absenteeism and unemployment. Moreover, impairment of body image can lead to significant psychological disturbances. Repeated failures of dieting and exercise to resolve the problem of obesity can result in feelings of despair and the development of clinical depression.

Bariatric surgery is often recommended for persons suffering from morbid obesity. Preferably, the invasive treatment is accompanied by changes in lifestyle, such as improved regulation of eating habits and an appropriate exercise regimen. Such lifestyle changes are dependent upon the self-discipline and cooperation of the patient.

US Patent Application Publication 2006/0089690 to Gerber, which is incorporated herein by reference, describes devices and methods for use in laparoscopic surgical procedures in which a medical implant is affixed to or implanted within an exterior surface of a body organ. A system is described that includes a laparoscopic cannula and a delivery instrument disposed within the cannula to fix a medical implant to an exterior surface of an organ. The delivery instrument has a distal end including a cavity and a vacuum port to draw a portion of the exterior surface of the organ into the cavity. The medical implant is affixed to the portion of the exterior surface drawn into the cavity of the delivery instrument.

U.S. Pat. No. 7,016,735 to Imran et al., which is incorporated herein by reference, describes a device, system and method for diagnosing and treating gastric disorders. A functional device resides within the patient's stomach and is secured to the stomach wall by an attachment device. The functional device may be a sensor for sensing various parameters of the stomach or stomach environment, or may be a therapeutic delivery device. The functional device in one embodiment provides a device, system and method for gastric electrical stimulation where stimulating electrodes are secured to the wall of the stomach by the attachment device or otherwise. A preferred device includes: at least one stimulating electrode in electrical contact with the stomach wall; an electronics unit containing the electronic circuitry of the device; and an attachment mechanism for attaching the device to the stomach wall. The functional devices may be programmed to respond to sensed information or signals. An endoscopic delivery system delivers the functional device through the esophagus and into the stomach where it is attached the stomach wall. The endoscopic instruments attach or remove the attachment devices and functional devices from the stomach and may be used to assist in determining the optimal attachment location.

US Patent Application Publication 2004/008023 to Imran et al., which is incorporated herein by reference, describes a device for diagnosing and treating gastric disorders. A functional device resides within the patient's stomach and is secured to the stomach wall by an attachment device. The functional device may be a sensor for sensing various parameters of the stomach or stomach environment, or may be a therapeutic delivery device. The functional device in one embodiment provides a device for gastric electrical stimulation where stimulating electrodes are secured to the wall of the stomach by the attachment device or otherwise. One device described includes: at least one stimulating electrode in electrical contact with the stomach wall; an electronics unit containing the electronic circuitry of the device; and an attachment mechanism for attaching the device to the stomach wall. The functional devices may be programmed to respond to sensed information or signals. An endoscopic delivery system delivers the functional device through the esophagus and into the stomach where it is attached the stomach wall. The endoscopic instruments attach or remove the attachment devices and functional devices from the stomach and may be used to assist in determining the optimal attachment location.

US Patent Application Publication 2005/0251219 to Evans, which is incorporated herein by reference, describes a device and method for placement of an instrument, specifically electrodes, in the GI tract, and allows for placement of electrodes for gastric electrical stimulation into the gastric wall using endoscopic techniques. The device has one or more electrodes disposed on an elongated body having a pointed first end and a "bolster" disposed on a second end. When placed within the GI tract, the first end of the device extends through the gastric and abdominal walls, extending outside of the patient's body with the bolster in contact against the inner lining of the gastric wall to retain the device. Exposed electrodes contact the gastric smooth muscle. Insulated wires in electrical connection with the electrodes run the length of the device body. Once the device is placed, the first end of the device body is removed to expose the wires, allowing electrical connection to an external electrical signal generator to provide electrical stimulus. In a described embodiment, the device is intended for endoscopic placement into, the GI tract, bringing an electrode into contact with the gastric smooth muscle where electrical stimulation is desired. Placement of the device follows a generally conventional percutaneous endoscopic gastrostomy (PEG) technique known as the "pull" method. Following known procedures of gastric insufflation to bring the stomach into apposition with the abdominal wall, and endoscopic transillumination of the abdominal wall to identify the implant site, a hollow needle is inserted through the abdominal wall and into the gastric lumen. A guide wire is inserted through the needle and into the gastric lumen, from whence the guide wire is withdrawn through the patient's mouth. The device is attached to the guide wire using a placement loop. The device is drawn through the patient's mouth and esophagus into the stomach and is positioned by the guide wire.

A book entitled, *Textbook of Gastroenterology*, 3rd edition, edited by Yamada (Lippincott, Williams & Wilkins), which is incorporated herein by reference, has in Chapter 10 thereof a description of the physiology of gastric motility and gastric emptying.

An abstract entitled, "Gastric myoelectrical pacing as therapy for morbid obesity: Preliminary results," by Cigaina et al., retrieved on Dec. 24, 2000 from the Web-site http://www.med-online.com/transneuronix/Product/abstract.htm, which is incorporated herein by reference, describes a method for applying monopolar and bipolar gastric stimulation to achieve weight loss.

An abstract entitled, "Implantable gastric stimulator (IGS) as therapy for morbid obesity: Equipment, surgical technique and stimulation parameters," by Cigaina et al., retrieved on Dec. 24, 2000 from the Web-site http://www.med-online.com/transneuronix/Product/abstract.htm, which is incorporated herein by reference, describes techniques of electrical signal therapy designed to treat obesity.

Stein et al. wrote an article related to providing incentives relating to medical care, entitled, "Carrots and sticks: Impact of an incentive/disincentive employee flexible credit benefit plan on health status and medical costs," American Journal of Health Promotion, May/June 1999, V5, I13, 5, which is incorporated herein by reference.

Giuffrida wrote an article regarding providing incentives for enhanced patient compliance, entitled, "Should we pay the patient? Review of financial incentives to enhance patient compliance," Biomedical Journal, vol. 315, pp. 703-707, 1997, which is incorporated herein by reference.

U.S. Pat. No. 6,270,455 to Brown, which is incorporated herein by reference, describes a networked system for communicating information to a patient and for remotely monitoring the patient. The system includes a server and a remote interface for entering in the server a set of queries to be answered by the patient. The server may be a web server and the remote interface may be a personal computer or remote terminal connected to the server via the Internet. The system also includes measurement apparatus for providing measurement data related to a patient's condition and treatment, and remotely programmable apparatus connected to the server via a communication network, such as the Internet. The remotely programmable apparatus interacts with the patient in accordance with a script program received from the server. The server includes a script generator for generating the script program from the set of queries entered through the remote interface. The script program is received and executed by the remotely programmable apparatus to communicate the queries to the patient, to receive responses to the queries, and to transmit the responses from the apparatus to the server. The measurement data provided by the measurement apparatus may include physiological condition data and drug delivery measurement data for paperless recordation at a remote location.

With respect to one embodiment, the Brown patent describes each patient to be monitored being provided with a monitoring device, designed to provide measurements of a physiological condition of the patient, to record the physiological condition measurements, and to transmit the measurements to the patient's remotely programmable apparatus, e.g., through a standard connection cable 30. Examples of suitable types of monitoring devices include blood glucose meters, respiratory flow meters, blood pressure cuffs, electronic weight scales, and pulse rate monitors. The specific type of monitoring device provided to each patient is dependent upon the patient's disease. For example, diabetes patients are provided with a blood glucose meter for measuring blood glucose concentrations, asthma patients are provided with respiratory flow meters for measuring peak flow rates, and obesity patients are provided with weight scales.

U.S. Pat. No. 6,129,685 to Howard, which is incorporated herein by reference, describes apparatus and methods for regulating appetite by electrical stimulation of the hypothalamus and by microinfusion of an appropriate quantity of a suitable drug to a distinct site or region within the hypothalamus.

U.S. Pat. No. 4,823,808 to Clegg et al., which is incorporated herein by reference, describes a method for treating obesity, including receiving a physiological measurement and generating audio or visual feedback for the patient to hear or see. The feedback is used for purposes of teaching behavior modification.

U.S. Pat. No. 5,868,141 to Ellias, which is incorporated herein by reference, describes an endoscopic stomach insert for reducing a patient's desire to eat.

U.S. Pat. Nos. 6,067,991 to Forsell, 5,601,604 to Vincent, 5,234,454 to Bangs, 4,133,315 to Berman et al., 4,416,267 to Garren et al., and U.S. Pat. Nos. 4,592,339, 5,449,368, 5,226,429 and 5,074,868 to Kuzmak, which are incorporated herein by reference, describe mechanical instruments for implantation in or around the stomach of an obese patient.

U.S. Pat. No. 5,690,691 to Chen et al., which is incorporated herein by reference, describes a gastric pacemaker for treating obesity and other disorders. The pacemaker includes multiple electrodes which are placed at various positions on the gastrointestinal (GI) tract, and deliver phased electrical stimulation to pace peristaltic movement of material through the GI tract.

U.S. Pat. No. 5,423,872 to Cigaina, which is incorporated herein by reference, describes apparatus for applying electrical pulses to the distal gastric antrum of a patient, so as to reduce the motility of the stomach and to thereby treat obesity or another disorder.

U.S. Pat. Nos. 5,188,104 and 5,263,480 to Wernicke et al., which are incorporated herein by reference, describe a method for stimulating the vagus nerve of a patient so as to alleviate an eating disorder.

U.S. Pat. Nos. 6,104,955, 6,091,992, and 5,836,994 to Bourgeois, 6,026,326 to Bardy, and 3,411,507 to Wingrove, which are incorporated herein by reference, describe the application of electrical signals to the GI tract to treat various physiological disorders.

U.S. Pat. No. 5,979,449 to Steer, which is incorporated herein by reference, describes an oral appliance for appetite suppression.

U.S. Pat. No. 4,975,682 to Kerr et al., which is incorporated herein by reference, describes apparatus for food intake regulation which is external to the body and which is based upon the voluntary cooperation of the subject in order to be effective.

U.S. Pat. Nos. 5,861,014 to Familoni, 5,716,385 to Mittal et al., and 5,995,872 to Bourgeois, are incorporated herein by reference, and describe methods and apparatus for stimulation of tissue, particularly gastrointestinal tract tissue.

PCT Patent Publication WO 98/10830 to Ben-Haim et al., entitled, "Fencing of cardiac muscles," and U.S. patent application Ser. No. 09/254,903 in the national phase thereof, both of which are assigned to the assignee of the present patent application and are incorporated herein by reference, describe various methods for controlling the behavior of muscle tissue, for example by blocking or altering the transmission of signals therethrough.

PCT Patent Publication WO 99/03533 to Ben-Haim et al., entitled, "Smooth muscle controller," and U.S. patent application Ser. No. 09/481,253 in the national phase thereof, both of which are assigned to the assignee of the present patent application and are incorporated herein by reference, describe apparatus and methods for applying signals to smooth muscle so as to modify the behavior thereof. In particular, apparatus for controlling the stomach is described in which a controller applies an electrical field to electrodes on the stomach wall so as to modify the reaction of muscle tissue therein to an activation signal, while not generating a propagating action potential in the tissue. In the context of the present patent application and in the claims, the use of such a non-excitatory signal to modify the response of one or more cells to electrical activation thereof, without inducing action potentials in the cells, is referred to as Excitable-Tissue Control (ETC). Use of an ETC signal is described in the PCT Patent Publication with respect to treating obesity, by applying the ETC signal to the stomach so as to delay or prevent emptying of the stomach. In addition, a method is described for increasing the motility of the gastrointestinal tract, by applying an ETC signal to a portion of the tract in order to increase the contraction force generated in the portion.

PCT Patent Publication WO 02/082968 to Policker et al., entitled, "Analysis of eating habits," which is assigned to the assignee of the present patent application and is incorporated herein by reference, describes apparatus and methods for detecting the occurrence of an eating event by a subject and analyzing the quantity and characteristics of the food ingested.

US Patent Application Publication 2004/0098068 to Carbunaru et al., which is incorporated herein by reference, describes techniques for both recharging and communicating with a stimulator having a rechargeable battery, which stimulator is implanted deeply in the body, in particular where the stimulator is a microstimulator. The system includes a base station and an external device, e.g., a chair pad. The chair pad may contain an antenna/charging coil and a booster coil. The antenna/charging coil can be used for charging the rechargeable battery and also for communicating with the stimulator using frequency shift keying and on-off keying. The booster coil can be used to recharge a battery depleted to zero volts. The base station connected to the chair pad may be used to power the antenna/charging coil and the booster coil.

U.S. Pat. No. 6,516,227 to Meadows et al., which is incorporated herein by reference, describes a spinal cord stimulation (SCS) system including a replenishable power source, e.g., a rechargeable battery, that requires only an occasional recharge. The SCS system monitors the state of charge of the internal power source and controls the charging process by monitoring the amount of energy used by the SCS system, and hence the state of charge of the power source. A suitable bidirectional telemetry link allows the SCS system to inform the patient or clinician regarding the status of the system, including the state of charge, and makes requests to initiate an external charge process.

US Patent Application Publication 2003/0114899 to Woods et al., which is incorporated herein by reference, describes techniques for detecting the status of a rechargeable battery included within an implantable medical device. The medical device can incorporate a status indicator which signals the user concerning the battery status, e.g., low battery level. The signal may be audible or it may arise from an electrical stimulation that is perceptually distinguished from the operative, therapeutic stimulation. The external programmer may also incorporate a second battery status indicator that is visual, audible, or physically felt. Battery status data may be conveyed on visual displays on the external programmer by uploading this information from the medical device using a bi-directional telemetry link.

U.S. Pat. No. 6,185,452 to Schulman et al., which is incorporated herein by reference, describes a device configured for implanting beneath a patient's skin for the purpose of tissue stimulation (e.g., nerve or muscle stimulation) and/or parameter monitoring and/or data communication. Alternatively, the device is configurable to monitor a biological parameter or to operate as a transponder to retransmit received command messages.

US Patent Application Publication 2004/0106963 to Tsukamoto et al., which is incorporated herein by reference, describes an implantable integrated power module incorporating a power source (e.g., a battery), a power management circuit, a magnetically inductive coupling system for remote communication and/or inductive charging, and a homing device for locating the implanted inductive charging coil. Communication (one- or two-way) may be carried out using the inductive charging link, a separate inductive pathway, or another pathway such as RF or light waves.

SUMMARY OF THE INVENTION

An embodiment of the invention provides apparatus and methods for detecting and tracking the swallowing of solids and liquids.

An embodiment of the invention provides apparatus and methods for detecting, tracking, quantifying and determining the qualitative character of ingested liquids and solids.

An embodiment of the invention provides apparatus and methods for treating obesity.

An embodiment of the invention provides apparatus and methods that enable the implementation of changes in food ingestion habits in a predictable and controlled manner.

An embodiment of the invention provides methods and apparatus for regulating food ingestion.

An embodiment of the invention provides apparatus and methods for bariatric surgery that are less drastic than those currently employed.

In some embodiments of the present invention, apparatus for detecting, tracking, quantifying and determining the qualitative character of ingested liquids and solids comprises a sensor coupled to a patient's gastrointestinal tract. Typically, the sensor generates a signal indicative of the swallowing of food. An analysis module typically determines a quality of the food, for example, whether it is predominantly solid or liquid, and stores this information in an electronic memory. Alternatively or additionally, the analysis module determines other characteristics of the ingested material, for example, the nutritional, chemical, and/or caloric content. "Food," as used in the context of the present patent application and in the claims, is to be understood as including both solid and liquid food. "Swallowing," as used in the context of the present patent application and in the claims, is to be understood as being indicative of the onset of eating.

In some embodiments of the present invention, swallowing is detected by tracking the electrical activity in muscle tissue in the fundic region of the stomach. Typically, the commencement of enhanced electrical activity is also detected in muscle tissue in the antral region of the stomach. Measurement of the time delay between swallowing and the commencement of electrical activity in the antrum is typically used to differentiate between solid and liquid matter, which are generally passed at different rates through the stomach.

Alternatively or additionally, swallowing is detected by at least one sensor placed at a site on the gastrointestinal tract other than the fundic region of the stomach, and the sensor generates a signal indicative of swallowing. Appropriate sites include, but are not limited to, a site on the esophagus, a site on the stomach, and a site on the throat. Whenever detection of swallowing is described in the present patent application with respect to fundic activity, it is to be understood as being by way of example, and not as excluding detection by a sensor located elsewhere on the gastrointestinal tract.

Typically, measurement of the intensity and/or duration of the electrical activity in the antral region is correlated with aspects of fundic electrical activity denoting swallowing, as described hereinbelow, such that ingested matter of differing chemical and nutritional content can be distinguished. Further typically, the amount of food accumulated in the fundus or antrum is estimated by measuring a level of electrical activity at various sites in the stomach.

Typically, electrical activity response criteria of the stomach of an individual patient are determined and calibrated by measuring the response of the patient's stomach to various types of solid and liquid food. To ensure appropriate compliance, calibration is typically performed under the supervision of a healthcare worker. For illustration, a table such as the following may be established for a particular patient. Except with respect to the example of sugarless chewing gum, these illustrative values are shown with respect to a constant volume of food or liquid ingested (e.g., 100 ml of steak, water, or tomato juice).

TABLE I

| Substance | Fundic activity level | Antral activity level | Time delay until onset of antral activity |
|---|---|---|---|
| Sugarless chewing gum | 1 | 1 | — |
| Non-caloric liquid - Water | 2 | 1 | — |
| Caloric liquid - Tomato juice | 2 | 2 | <1 Minute |
| Caloric liquid - Milk | 2 | 2 | <1 Minute |
| Solid - Apple | 2 | 2 | Minutes |
| Solid - Meat | 2 | 3 | Minutes |

In this illustration, the measured data are typically analyzed to determine signal characteristics corresponding to the indicated fundic and antral electrical activity levels. For example, calibration of fundic activity during the chewing of sugarless gum typically yields a low level indication of swallowing, while calibration during the swallowing of liquids and solids yields a greater fundic response. Similarly, there is typically no significant antral response to the patient drinking water, while calibration during the digestion of liquids or solids having higher caloric content yields a greater antral response. Measurements are typically made of the delay time between swallowing and the commencement of antral activity, because consumption of liquids is typically characterized by a rapid transition from the fundus to the antrum, while solids typically stay in the fundus for at least about 10 minutes prior to being passed to the antrum. Typically, a large variety of liquids and solids are used to establish a profile of electrical response characteristics for each patient.

In some embodiments of the present invention, eating detection is accomplished by monitoring the mechanical impedance of the fundus and the rate of the antral slow waves, whereby an eating event is indicated when both the mechanical impedance of the fundus and the rate of the antral slow waves cross threshold values within a certain time period. Threshold values may be (a) generally predetermined, or (b) determined for each individual patient during a calibration process, in which the patient ingests various types of food while the mechanical impedance of the fundus and the rate of the antral slow waves are monitored, along with other relevant physiological data.

The threshold values indicating an eating event are typically updated to ensure accurate detection of eating by the patient. For some applications, the threshold values indicative of eating are modified through the use of a control unit that adapts the threshold values by checking that an indicated eating event corresponds to an actual eating event. Such checking may include relying on the patient to periodically verify or deny an eating event and/or through additional sensor information. For example, a repeated false positive indication of eating due to normal gastric activity would cause one or more of the threshold values used to signify an eating event to be modified.

Alternatively or additionally, the control unit is adapted to change one or more of the threshold values in response to a physiological event that has a tendency to cause false indications of eating activity. For example, a phenomenon known as the migrating motor complex (MMC) is characterized by a change in rhythm of antral electrical activity. This change in antral electrical activity is largely unrelated to eating, but can lead to false indications of eating activity. Since MMC activity lasts about 10 minutes and appears in a cyclical manner with a period of about 40 minutes, the control unit is adapted to identify MMC activity and respond, such that false positive identifications of eating activity are reduced. For example, when a change in antral electrical activity is detected, which may be indicative of eating, the control unit examines data on antral electrical activity from 30 to 50 minutes prior thereto, searching for similar activity that may be indicative of MMC activity. If the current activity is likely to be related to MMC activity, then the fundic threshold level signifying an eating event is increased during the subsequent times that are between 30 and 50 minutes in the future (i.e., when subsequent MMC activity is expected), thus reducing the likelihood of false positives relating to MMC contractions. As appropriate, other periodic physiological activities of the gastrointestinal system are treated in a similar manner. It is to be understood that the period of the MMC activity is described herein as being between 30 and 50 minutes by way of illustration and not limitation. In some patients, the period of the MMC activity may be higher, e.g., 50 to 90 minutes, or 90 to 120 minutes. For some applications, a calibration period is provided to determine the length of the period for each patient.

For some applications, various supplemental sensors are also applied to the gastrointestinal tract or elsewhere on or in the patient's body. These supplemental sensors, which may comprise pH sensors, blood sugar sensors, ultrasound transducers or mechanical sensors, typically convey signals to a control unit of the apparatus indicative of a characteristic of solids or liquids ingested by the patient. For example, an ultrasound transducer may be coupled to indicate whether ingesta are solid or liquid, and a pH sensor may indicate that an acidic drink such as tomato juice was consumed rather than a more basic liquid such as milk.

In some embodiments, the collected data are stored and intermittently uploaded to an external computer, typically by a wireless communications link, for review by the patient's physician, to enable monitoring of the patient's adherence to a dietary regimen.

For some applications, a specific schedule of allowed food ingestion is pre-programmed by the physician into the memory, and a processor is continuously operative to detect whether food consumption is taking place in accordance with the programmed schedule. For some patients, the schedule may be less strict with respect to drinking certain types of liquids, and more strict with respect to eating certain types of solid food. When an exception from the schedule is detected, the processor typically actuates a signal generator to convey an ingestion-control signal to the patient, in order to encourage the patient to adhere to the schedule. Typically, but not necessarily, apparatus and methods described in U.S. Provisional Patent Application 60/259,925, entitled, "Regulation of eating habits," filed Jan. 5, 2001, and in a PCT patent application entitled, "Regulation of eating habits," filed in January, 2002, both of which are assigned to the assignee of the present patent application and incorporated herein by reference, are utilized in the administration of the ingestion-control signal. Alternatively or additionally, the signal generator generates a visual, audio, or other cue or causes another reasonable discomfort to encourage the patient to adhere to the schedule.

For embodiments in which this form of dietary monitoring is supplemented by dietary regulation, the apparatus typically compares the indications of actual food and drink consumption with the pre-programmed schedule. In the event of a sufficient level of patient non-compliance, the ingestion-control signal is typically delivered to the patient's stomach via a set of electrodes placed in a vicinity thereof, so as to induce a sensation of discomfort or minor nausea. For example, an unpleasant sensation, such as nausea, may be induced by altering the natural electrical activity of the stomach, thereby inducing gastric dysrhythmia, or, alternatively, discomfort may be induced by pacing the rectus abdominus muscle.

Alternatively or additionally, the signal is applied to another site on or in the patient's body. For example, the ingestion-control signal may be applied mechanically or electrically in a vicinity of the cochlear nerve, so as to induce vertigo. Alternatively, the signal is applied so as to generate a brief pain sensation anywhere on the patient's body, which only recurs if the patient continues to eat. Further alternatively, the signal is applied to the esophagus or to the lower esophageal sphincter, so as to cause contraction of muscle tissue therein, thereby making any further eating difficult or very uncomfortable.

Alternatively or additionally, the ingestion-control signal is configured so as to induce a feeling of satiation, typically but not necessarily in accordance with methods described in U.S. patent application Ser. No. 09/734,358, entitled, "Acute and chronic electrical signal therapy for obesity," filed on Dec. 21, 2000, which is assigned to the assignee of the present patent application and is incorporated herein by reference. For example, methods described in that application for engendering a feeling of satiation may be applied in conjunction with embodiments of the present invention, such that muscles in the vicinity of stretch receptors in the stomach are caused to contract, thereby resulting in decreased hunger sensations. Alternatively or additionally, the feeling of satiation is induced by applying electrical signals which enhance the mobility of chyme from the fundus to the antrum of the stomach, where stretch-receptor signals are generally generated to a greater extent for a given quantity of food than in the fundus.

In another embodiment, when an exception from the schedule of allowed food ingestion is detected, the processor typically conveys the exception to an external operator control unit, which in turn wirelessly communicates the exception in real time to a remote computer system. The remote computer system can be configured to analyze the exception based on predetermined rules and, if necessary, perform an appropriate action, such as notification of a healthcare worker, care provider, or family member of the patient, in order to encourage the patient to adhere to the schedule.

Typically, the schedule of allowed food ingestion can be modified after implantation of the apparatus, typically by means of a wireless communications link. In this manner, the schedule can be adjusted in response to changes in the patient's eating habits and experience with the apparatus.

In an embodiment, antral electrical activity of a subject is monitored, and a signal is applied to a vagus nerve of the subject in temporal coordination with the monitored antral electrical activity. For example, the signal may be applied during a slow wave as indicated by antral electrical or mechanical activity, or by other means. Alternatively or additionally, the signal is applied within 5 or 10 seconds before an anticipated slow wave, or within 5 or 10 seconds after a slow wave. As appropriate, this technique of vagus nerve stimulation may be coordinated, alternatively or additionally, with measurements of fundic impedance.

Typically, bursts of antral electrical activity occur several times a minute. In an embodiment, a signal is applied to the vagus nerve synchronized with each burst (e.g., (a) during the burst, (b) shortly following a defined feature of the burst, (c) prior to an anticipated feature of the burst, or (d) following a slow wave). For some applications, techniques described: (a) herein, (b) in the above-cited U.S. Pat. Nos. 5,188,104 and 5,263,480 to Wernicke et al., and/or (c) in the other references cited in the Background section of this application, are adapted for use in carrying out this embodiment of the present invention.

There is therefore provided, in accordance with an embodiment of the present invention, gastric apparatus, including:

a gastrointestinal sensor, adapted to be coupled to a gastrointestinal site of a subject and to generate a gastrointestinal sensor signal responsive to a property of the gastrointestinal site;

a set of one or more antral sensors, adapted to be coupled to an antral site of an antrum of the stomach and to generate an antral sensor signal responsive to a property of the antrum; and a control unit, adapted to receive and analyze the gastrointestinal and antral sensor signals, and to determine, responsive thereto, a characteristic of a food ingested by the subject.

Typically, the control unit is adapted to be implanted in the subject.

In an embodiment, the characteristic of the ingested food includes a caloric content of the ingested food, and the control unit is adapted to determine the caloric content. Alternatively or additionally, the characteristic of the ingested food includes a chemical content of the ingested food, and the control unit is adapted to determine the chemical content. Further alternatively or additionally, the characteristic of the ingested food includes a nutritional content of the ingested food, and the control unit is adapted to determine the nutritional content.

For some applications, the apparatus includes an operator unit, which is adapted to be disposed external to the subject and to transmit a control signal to the control unit.

In an embodiment, the gastrointestinal sensor is adapted to generate a swallowing sensor signal responsive to swallowing by the subject. Typically, the gastrointestinal sensor is adapted to be placed at an esophageal site of the subject, a site of the stomach of the subject, and/or a site of a throat of the subject.

Typically, the gastrointestinal sensor includes a set of one or more fundic sensors, adapted to be coupled to a fundic site of a fundus of the stomach of the subject and to generate a fundic sensor signal responsive to a property of the fundus, and the control unit is adapted to receive and analyze the fundic and antral sensor signals, and to determine, responsive thereto, the characteristic of the ingested food. In an embodiment, the fundic sensor set includes one or more strain gauges. Alternatively or additionally, the antral sensor set includes one or more strain gauges.

Typically, the fundic sensor set includes a set of fundic electrodes, adapted to generate a fundic electrode signal responsive to a property of the fundus, the antral sensor set includes a set of antral electrodes, adapted to generate an antral electrode signal responsive to a property of the antrum, and the control unit is adapted to receive and analyze the fundic and antral electrode signals, and to determine, responsive thereto, the characteristic of the ingested food. For example, the control unit may be adapted to determine, responsive to an analysis of at least one of the electrode signals, an amount of the ingested food accumulated in a region of the stomach. Alternatively or additionally, the control unit is adapted to count, responsive to an analysis of at least one of the electrode signals, a number of meals ingested by the subject during a period of time.

The antral electrode set typically includes two antral electrodes, adapted to be coupled to two sites of the antrum, and the control unit is adapted to identify a measure of electrical impedance between the two sites of the antrum. In this case, the control unit is typically adapted to determine the characteristic of the ingested food, responsive to a change in the measure of electrical impedance. For some applications, the fundic electrode set includes two fundic electrodes, adapted to be coupled to two sites of the fundus, and the control unit is adapted to identify a measure of electrical impedance between the two sites of the fundus. For example, the control unit may be adapted to determine the characteristic of the ingested food, responsive to a change in the measure of electrical impedance. Alternatively or additionally, the control unit is adapted to identify an increased measure of electrical impedance relative to a baseline value as indicative of eating. Further alternatively or additionally, the control unit is adapted to identify a substantial return towards a baseline value of the measure of electrical impedance as indicative of a termination of eating.

For some applications, the control unit is adapted to identify an increase in the measure of electrical impedance as indicative of an onset of eating. For example, the control unit may be adapted to detect the onset of eating, responsive to the increase in the measure of electrical impedance being greater than 5 ohms per centimeter of distance between the two sites of the fundus.

In an embodiment, the control unit is adapted to perform a calibration including measurement of a response of the fundic and antral electrode signals to ingestion by the subject of one or more test foods. For example, the one or more foods may include one or more solid foods, and the control unit may be adapted to perform the calibration responsive to ingestion of the one or more solid foods. Alternatively or additionally, the one or more foods includes one or more liquid foods, and the control unit is adapted to perform the calibration responsive to ingestion of the one or more liquid foods. Further alternatively or additionally, the one or more foods includes one or more solid foods and one or more liquid foods, and herein the control unit is adapted to perform the calibration responsive to ingestion of the one or more solid foods and the one or more liquid foods.

In an embodiment, the antral electrode set is adapted to generate the antral electrode signal responsive to an electrical potential change generated responsive to a contraction of a muscle of the antrum. In this case, the control unit is typically adapted to determine, responsive to an amplitude of the antral electrode signal, the characteristic of the ingested food. Alternatively or additionally, the control unit is adapted to determine, responsive to a frequency of the antral electrode signal, the characteristic of the ingested food. Further alternatively or additionally, the control unit is adapted to determine, responsive to a spike energy per antral cycle of electrical activity, the characteristic of the ingested food. Still further alternatively or additionally, the control unit is adapted to determine, responsive to a duration of the antral electrode signal, the characteristic of the ingested food.

In an embodiment, the control unit is adapted to determine, responsive to a change in a rate of antral electrode signal events, the characteristic of the ingested food. The control unit may alternatively or additionally be adapted to identify an increase in an amplitude of the antral electrode signal as indicative of an onset of a cephalic phase occurring in the subject. For some applications, the control unit is adapted to identify an increase in an amplitude of the antral electrode signal as indicative of an onset of antral digestion. Alternatively or additionally, the control unit is adapted to identify a reduction in a rate of antral electrode signal events as indicative of an onset of antral digestion.

For some applications, the control unit is adapted to identify an increased amplitude of the antral electrode signal relative to a baseline value as indicative of antral digestion. Alternatively or additionally, the control unit is adapted to identify a reduced rate of antral electrode signal events relative to a baseline value as indicative of antral digestion. Further alternatively or additionally, the control unit is adapted to identify a substantial return towards a baseline value of an amplitude of the antral electrode signal as indicative of a termination of antral digestion. Still further alternatively or additionally, the control unit is adapted to identify a substantial return towards a baseline value of a rate of antral electrode signal events as indicative of a termination of antral digestion.

The control unit is typically adapted to determine the characteristic of the ingested food, responsive to a time delay between an onset of eating and an onset of a decreased rate of electrical events in the antrum. For some applications, the control unit is adapted to determine the characteristic of the ingested food, responsive to the time delay and responsive to a threshold time delay. Alternatively or additionally, the control unit is adapted to determine, responsive to the time delay, an extent to which the ingested food includes solid food matter. In this case, the control unit is typically adapted to determine that the ingested food includes solid food matter, responsive to the time delay being more than about one minute. For some applications, the control unit is adapted to determine that the ingested food includes predominantly solid food matter, responsive to the time delay being more than about 5 minutes.

In an embodiment, the control unit is adapted to determine, responsive to the time delay, an extent to which the ingested food includes liquid food matter. For example, the control unit may be adapted to determine that the ingested food includes liquid food matter, responsive to the time delay being less than about 5 minutes. Alternatively or additionally, the control unit is adapted to determine that the ingested food includes predominantly liquid food matter, responsive to the time delay being less than about one minute.

For some applications, the control unit is adapted to determine the characteristic of the ingested food, responsive to a time delay between an onset of eating and an onset of increased electrical activity in the antrum. In this case, the control unit is typically adapted to determine the characteristic of the ingested food, responsive to the time delay and responsive to a threshold time delay. In an embodiment, the control unit is adapted to determine, responsive to the time delay, an extent to which the ingested food includes solid food matter. For example, the control unit may be adapted to determine that the ingested food includes solid food matter, responsive to the time delay being more than about one minute. Alternatively or additionally, the control unit may be adapted to determine that the ingested food includes predominantly solid food matter, responsive to the time delay being more than about 5 minutes. In an embodiment, the control unit is adapted to determine, responsive to the time delay, an extent to which the ingested food includes liquid food matter. For example, the control unit may be adapted to determine that the ingested food includes liquid food matter, responsive to the time delay being less than about 5 minutes. Alternatively or additionally, the control unit is adapted to determine that the ingested food includes predominantly liquid food matter, responsive to the time delay being less than about one minute.

Typically, the fundic electrode set is adapted to generate the fundic electrode signal responsive to an electrical potential change generated responsive to a contraction of a muscle of the fundus. For example, the control unit may be adapted to determine the characteristic of the ingested food responsive to an amplitude of the fundic electrode signal, a frequency of the fundic electrode signal, a duration of the fundic electrode signal, and/or a change in a rate of fundic electrode signal events of the fundic electrode signal.

In an embodiment, the control unit is adapted to identify an increased amplitude of the fundic electrode signal relative to a baseline value as indicative of eating. Alternatively or additionally, the control unit is adapted to identify an increased frequency of the fundic electrode signal relative to a baseline value as indicative of eating. Further alternatively or additionally, the control unit is adapted to identify a substantial return towards a baseline value of an amplitude of the fundic electrode signal as indicative of a termination of eating. Still further alternatively or additionally, the control unit is adapted to identify a substantial return towards a baseline value of a frequency of the fundic electrode signal as indicative of a termination of eating. For some applications, the control unit is adapted to identify an increase in an amplitude of the fundic electrode signal as indicative of an onset of eating. For example, the control unit may be adapted to detect the onset of eating responsive to the increase in the amplitude of the fundic electrode signal being greater than about 20 percent.

In an embodiment, the control unit is adapted to identify an increase in a frequency of the fundic electrode signal as indicative of an onset of eating. For example, the control unit may be adapted to detect the onset of eating, responsive to the increase in the frequency being greater than about 10 percent.

In an embodiment, the control unit includes a memory, adapted to store a result of the analysis performed by the control unit. Typically, the memory is adapted to upload the stored result to an external computer, e.g., by using a wireless communications link.

In an embodiment, the apparatus includes a supplemental sensor adapted to be placed at a site of the subject and to convey a supplemental sensor signal to the control unit. The control unit is typically adapted to receive and analyze the supplemental sensor signal, and to determine, responsive thereto, the characteristic of the ingested food. Alternatively or additionally, the control unit is adapted to receive and analyze the supplemental sensor signal, and to determine, responsive thereto, an onset of eating by the subject. Further alternatively or additionally, the control unit is adapted to receive and analyze the supplemental sensor signal, and to determine, responsive thereto, eating by the subject. Still further alternatively or additionally, the control unit is adapted to receive and analyze the supplemental sensor signal, and to determine, responsive thereto, a termination of eating by the subject. Typically, the supplemental sensor includes an electrode, a pH sensor, a blood sugar sensor, an ultrasound transducer, and/or a mechanical sensor. In an embodiment, the supplemental sensor is adapted to be placed at a gastrointestinal site of the subject, an esophageal site of the subject, a site of the stomach of the subject, and/or a site of a throat of the subject.

For some applications, the control unit includes a memory, adapted to store a schedule of allowed food ingestion, wherein the apparatus includes an operator unit, which is adapted to be disposed external to the subject, and wherein the operator unit is adapted to generate an external cue when the analysis performed by the control unit is indicative of the subject not eating in accordance with the ingestion schedule. For example, the external cue may include a visual cue, and the operator unit is adapted to generate the visual cue. Alternatively or additionally, the external cue includes an audio cue, and the operator unit is adapted to generate the audio cue. For some applications, the operator unit includes a user override, adapted to be used by the subject and adapted to disable the cue. Alternatively or additionally, the operator unit is adapted to modify the schedule stored in the memory. For example, the operator unit may be adapted to modify the schedule responsive to information obtained by the operator unit, e.g., via a wireless communications link.

In an embodiment, the apparatus includes a set of one or more current-application electrodes, adapted to be coupled to a tissue of the subject, and wherein the control unit is adapted to drive a current, responsive to the analysis, through the set of current-application electrodes into the tissue. For example, the current-application electrode set may be adapted to be placed at an aural site of the subject, at an esophageal site of the subject, and/or at a site of the stomach of the subject. For some applications, the control unit is adapted to drive the current into the tissue responsive to the characteristic of the ingested food. In an embodiment, the control unit is adapted to apply a pacing signal to a rectus abdominus muscle of the subject. For some applications, the control unit is adapted to drive the current into the tissue responsive to a time of the subject eating.

In an embodiment, the control unit is adapted to configure the current such that driving the current induces gastric dysrhythmia. Alternatively or additionally, the control unit is adapted to configure the current such that driving the current disrupts coupling of gastric mechanical activity and gastric electrical activity of the subject. Further alternatively or additionally, the control unit is adapted to configure the current such that driving the current induces a sensation of discomfort in the subject. Still further alternatively or additionally, the control unit is adapted to configure the current such that driving the current induces a sensation of nausea in the subject. Yet further alternatively or additionally, the control unit is adapted to configure the current such that driving the current induces a sensation of vertigo in the subject.

In an embodiment, the control unit is adapted to drive the current-application electrode set to apply an Excitable-Tissue Control (ETC) signal to the tissue. For example, the control unit may be adapted to drive the current-application electrode set to apply a stimulatory pulse at a site of application of the ETC signal. Alternatively or additionally, the control unit is adapted to drive the current-application electrode set to apply a stimulatory pulse to tissue at a site other than a site of application of the ETC signal. Still further alternatively or additionally, the control unit is adapted to drive the current-application electrode set to apply the ETC signal in order to increase an aspect of contraction of the tissue. For some applications, the control unit is adapted to drive the current-application electrode set to apply the ETC signal in order to cause tissue contraction in a first portion of the stomach of the subject, and stretching of a stretch receptor of the stomach in a second portion of the stomach. Alternatively or additionally, the control unit is adapted to drive the current-application electrode set to apply the ETC signal in order to increase a contraction strength of tissue in a vicinity of a stretch receptor of the stomach of the subject, so as to increase a sensation of satiation of the subject. Further alternatively or additionally, the control unit is adapted to drive the current-application electrode set to apply the ETC signal to the tissue so as to enhance movement of chyme from a fundus to the antrum of the stomach of the subject.

In an embodiment, the control unit includes a memory, adapted to store a schedule of allowed food ingestion, and wherein the control unit is adapted to withhold driving the current when the analysis performed by the control unit is indicative of the subject eating in accordance with the ingestion schedule. Typically, the ingestion schedule includes types of foods and associated amounts permitted during a time period, and the control unit is adapted to withhold driving the current when the analysis is indicative of the subject eating in accordance with the ingestion schedule. Alternatively or additionally, the ingestion schedule includes a number of meals permitted during a time period, and the control is adapted to withhold driving the current when the analysis is indicative of the subject eating in accordance with the ingestion schedule. Further alternatively or additionally, the ingestion schedule includes an amount of food permitted at a certain meal, and the control is adapted to withhold driving the current when the analysis is indicative of the subject eating in accordance with the ingestion schedule.

Typically, the memory is adapted to download a new schedule from an external computer. For some applications, the apparatus includes an operator unit, which is adapted to be disposed external to the subject and to transmit a control signal to the control unit. In an embodiment, the operator unit includes a user override, adapted to be used by the subject and adapted to withhold driving the current.

There is further provided, in accordance with an embodiment of the present invention, a method for analyzing gastric function of a stomach of a subject, including:

sensing a property of a gastrointestinal tract of the stomach;
sensing a property of an antrum of the stomach;
analyzing the property of the gastrointestinal tract and the property of the antrum; and
determining, responsive to the analysis, a characteristic of a food ingested by the subject.

There is also provided, in accordance with an embodiment of the present invention, gastric apparatus, including:

one or more sensors, adapted to generate respective sensor signals responsive to activity of a gastrointestinal tract of a subject; and
a control unit, adapted to:
receive and analyze the sensor signals,
determine that an eating event has occurred, responsive to at least one of the sensor signals and a threshold,
identify an aspect of at least one of the sensor signals deriving from rhythmic activity of the gastrointestinal tract that is not indicative of current eating by the subject, and
modify the threshold responsive to the aspect of the signals that derives from activity that is not indicative of current eating.

In an embodiment, the control unit is adapted to modify the threshold if the aspect is indicative of a migrating motor complex (MMC).

In an embodiment:
in modifying the threshold, the control unit is adapted to modify the threshold in a threshold-modification direction, and
the control unit is adapted, at a later time at least 30 minutes following modifying the threshold, to further modify the threshold in the threshold-modification direction responsive to identifying at the later time the aspect of the signals deriving from activity that is not indicative of current eating by the subject.

In an embodiment, the control unit is adapted, at a later time at least 30 minutes following modifying the threshold, to at least partially restore the threshold towards a previous value thereof, responsive to not identifying at the later time the aspect of the signals deriving from activity that is not indicative of current eating by the subject.

In an embodiment, the control unit is adapted to modify the threshold responsive to a relationship between a previous portion of the sensor signals and a current portion of the sensor signals.

In an embodiment, the control unit is adapted to modify the threshold responsive to the relationship, the previous portion being between about 30 and about 50 minutes prior to the current portion.

In an embodiment, the control unit is adapted to identify the previous portion of the sensor signals as being indicative of a migrating motor complex (MMC) and to identify the current portion of the sensor signals as being indicative of a MMC, and to modify the threshold responsive to identifying the previous and current portions as being indicative of the MMC.

There is additionally provided, in accordance with an embodiment of the present invention, apparatus, including:

a sensor, adapted to generate a signal responsive to antral electrical activity of a subject; and
a vagus nerve stimulator, adapted to receive the signal and, responsive thereto, to stimulate a vagus nerve of the subject in temporal coordination with an aspect of the sensed signal.

There is still additionally provided, in accordance with an embodiment of the present invention, a selection method, including:

non-invasively recording a fasting electrogastrogram of a patient; and
identifying the patient as a candidate for implantation of a medical device responsive to a rate of slow wave activity of the patient being greater than a threshold rate.

In an embodiment, the threshold rate is at least 2.9 cycles per minute.

In an embodiment, identifying the patient includes identifying the patient as a candidate for implantation of a device capable of applying an ETC signal, responsive to the rate of slow wave activity being greater than the threshold rate.

In an embodiment, the method includes rejecting the patient as a candidate for implantation of the medical device responsive to the rate of slow wave activity being less than 2.9 cycles per minute.

There is also provided, in accordance with an embodiment of the present invention, gastric apparatus, including:

one or more sensors, adapted to generate respective sensor signals responsive to activity of a gastrointestinal tract of a subject;

an implantable control unit, comprising a rechargeable battery and at least one first coil, the implantable control unit adapted to receive the sensor signals, and transmit data responsive thereto; and an external control unit, comprising a power source and at least one second coil, the external control unit adapted to:

drive the power source to inductively transfer energy via the second coil to the first coil, so as to recharge the battery, and receive the transmitted data.

There is also provided, in accordance with an embodiment of the invention apparatus, including:

a control unit, adapted to be implanted within a patient; and a corkscrew-shaped electrode mount, adapted to be implanted in a wall of a stomach of the patient, including:

first and second electrodes, at respective sites of the electrode mount; and a controller, wirelessly coupled to the control unit.

In an embodiment, the corkscrew-shaped electrode mount extends in its corkscrew shape for between 150 and 270 degrees, between 270 and 360 degrees, between 360 and 540 degrees, between 540 and 720 degrees, or for greater than 720 degrees.

In an embodiment, the apparatus includes an implantation tool, wherein the corkscrew-shaped electrode mount is coiled around the implantation tool and corkscrewed therefrom into the wall of the stomach.

In an embodiment, the corkscrew-shaped electrode mount includes at least a number of electrodes selected from the group consisting of: 4, 5, 20, 50, and 100.

In an embodiment, the corkscrew-shaped electrode mount includes a force transducer, adapted to generate a signal in response to filling of the stomach.

In an embodiment, the controller is disposed at a site along the corkscrew-shaped electrode mount between the first and second electrodes.

In an embodiment, the first and second electrodes are disposed at non-opposing sites with respect to a longitudinal axis of the corkscrew-shaped electrode mount.

In an embodiment, the apparatus includes an endoscope including a plurality of cartridges, each cartridge including a respective corkscrew-shaped electrode mount.

In an embodiment, the first and second electrodes are adapted to both be in contact with a muscular layer of the stomach following implantation.

In an embodiment, the first and second electrodes are adapted to be not in contact with a mucosal layer of the stomach following implantation.

In an embodiment, with respect to a longitudinal axis of the corkscrew-shaped electrode mount, the first electrode is disposed at 12 o'clock and the second electrode is disposed at a site between 4 o'clock and 6 o'clock.

In an embodiment, the second electrode is disposed at 6 o'clock with respect to the longitudinal axis.

In an embodiment, the second electrode is disposed at a site along the corkscrew-shaped electrode mount between the first electrode and the controller.

In an embodiment, the apparatus includes a tool for implanting the mount in the wall of the stomach, and wherein the mount is adapted to be coupled to the tool during the implantation such that the controller enters the wall of the stomach before the first and second electrodes enter the wall.

In an embodiment, the tool is adapted to place at least a portion of the controller at a site outside of the stomach.

In an embodiment, the controller is adapted to wirelessly transmit data to the control unit, responsively to a current between the electrodes.

In an embodiment, the electrode mount is adapted to flex in response to filling of the stomach, wherein the current varies in response to the flexing, and wherein the control unit is adapted to identify filling of the stomach in response to variation of the current.

In an embodiment, the controller is adapted to wirelessly receive power from the control unit, responsively to the data.

In an embodiment, the controller is adapted to apply a signal to the stomach responsively to receiving the power.

There is further provided, in accordance with an embodiment of the invention, apparatus, including:

an electrode, adapted to be implanted in a wall of a stomach of the patient;

a clamshell cover, adapted to enclose the electrode and to penetrate a mucosal layer of the stomach in a closed clamshell disposition; and a tool, adapted to be activated by an operator to open the clamshell cover at a time after the clamshell cover has entered the mucosal layer to allow the electrode to be coupled to a muscular layer of the stomach.

There is yet further provided, in accordance with an embodiment of the invention, apparatus, including:

an endoscope;

a flexible arrangement including first and second electrodes; and a shape-defining element coupled to the endoscope and to the flexible arrangement, the element having a property of being able to be placed in one shape during the application of forces thereto, and to assume a natural shape thereof in the absence of external forces applied thereto, the element adapted to enter a wall of a stomach with the flexible arrangement.

In an embodiment, the natural shape of the shape-defining element is a corkscrew shape.

In an embodiment, the shape-defining element and the flexible arrangement are wound around an outer surface of a portion of the endoscope.

In an embodiment, the flexible arrangement is disposed within the shape-defining element.

In an embodiment, the shape-defining element is disposed within the endoscope.

In an embodiment, the shape-defining element includes a shape-defining catheter.

In an embodiment, the shape-defining element is adapted to have its natural shape defined at a time of being separated from the endoscope.

In an embodiment, the shape-defining element is adapted to have its natural shape defined by being extruded from the endoscope.

In an embodiment, the shape-defining element is dissolvable after implantation in a patient.

In an embodiment, the shape-defining element includes a dissolvable coating on the flexible arrangement.

In an embodiment, the shape-defining element is adapted to be advanced by the endoscope to a site within the stomach, to be inserted into the wall of the stomach, to be in a curved shape after insertion into the wall, to cause the flexible arrangement to be in the curved shape in the wall, and to remain in the wall for less than one week.

In an embodiment, the shape-defining element is adapted to be withdrawn from the wall and wherein the flexible arrangement is adapted to remain in the wall.

In an embodiment, the apparatus includes a hooking element coupled to the flexible arrangement, adapted to maintain the flexible arrangement in the wall when the shape-defining element is withdrawn.

There is still further provided, in accordance with an embodiment of the invention, apparatus, including:

an endoscope; and a plurality of electrode cartridges within the endoscope, each cartridge including at least one electrode for implantation in a patient.

In an embodiment, each component associated with any given cartridge is (a) adapted to be implanted in the patient, (b) dissolvable within the patient, or (c) able to pass through a gastrointestinal tract of the patient and be passed out of the patient during a bowel movement.

There is also provided, in accordance with an embodiment of the invention, apparatus, including:

an endoscope; and an insertion head coupled to the endoscope and including an electrode, the insertion head being adapted to be pushed through a wall of a stomach to a site outside of the stomach and to be subsequently moved by the endoscope in a manner that places the electrode in contact with a muscular layer of the stomach.

In an embodiment, the insertion head is adapted to be rotated by the endoscope to place the electrode in contact with the muscular layer.

In an embodiment, the insertion head is adapted to be pulled by the endoscope to place the electrode in contact with the muscular layer.

In an embodiment, the electrode includes a needle electrode.

In an embodiment, the electrode includes a single electrode.

In an embodiment, the electrode includes a plurality of electrodes.

There is also provided, in accordance with an embodiment of the invention, a method, including:

passing into a stomach of a patient an endoscope having electrode apparatus, the electrode apparatus including at least one electrode;

pushing the electrode apparatus through a wall of the stomach to a site outside of the stomach;

moving the electrode apparatus while it is outside of the stomach in a manner that places the electrode in contact with the wall (e.g., a muscular or submucosal layer) of the stomach; and leaving the electrode in the wall.

There is additionally provided, in accordance with an embodiment of the invention, a method, including:

passing electrode apparatus into a stomach of a patient, the electrode apparatus including at least one electrode;

pushing the electrode apparatus through a wall of the stomach to a site outside of the stomach;

moving the electrode apparatus while it is outside of the stomach in a manner that places the electrode in contact with a wall (e.g., muscular or submucosal layer) of the stomach; and leaving the electrode in the wall.

In an embodiment, passing the electrode apparatus includes passing an endoscope to which the electrode apparatus is coupled.

In an embodiment, the electrode apparatus includes at least one needle electrode, and wherein leaving the electrode includes leaving the needle electrode in the muscular layer.

There is yet additionally provided, in accordance with an embodiment of the invention, a method for implanting gastric leads, including:

applying positive gas pressure through one lumen of an endoscope;

applying negative gas pressure through another lumen of the endoscope; and implanting the leads using the endoscope.

There is still additionally provided, in accordance with an embodiment of the invention, an implantation system, including:

transluminal apparatus configured to provide access to a gastric implantation site of a patient and to apply pressure to the gastric implantation site;

an electrode, configured for implantation at the implantation site; and abdominal cavity apparatus configured to be positioned within an abdomen of the patient, outside of the stomach, wherein the system is configured such that application of the pressure by the transluminal apparatus facilitates insertion of the electrode into the wall by the abdominal cavity apparatus.

In an embodiment, the transluminal apparatus is configured to apply the pressure in a manner that brings the site adjacent to an abdominal wall of the patient.

In an embodiment, the transluminal apparatus includes at least one endoscope.

In an embodiment, prior to the insertion of the electrode, the transluminal apparatus and the abdominal cavity apparatus are independently manipulatable.

In an embodiment, the transluminal apparatus is configured to apply suction to the gastric implantation site.

In an embodiment, the electrode includes a needle electrode.

In an embodiment, the abdominal cavity apparatus is configured to be passed through an abdominal wall of the patient, towards the stomach.

In an embodiment, a distal tip of the transluminal apparatus is configured to be within the stomach, adjacent to the implantation site, when the abdominal cavity apparatus inserts the electrode into the wall.

In an embodiment, the transluminal apparatus is configured to apply the pressure by inflating the stomach.

In an embodiment, a physical portion of the transluminal apparatus is configured to apply the pressure to the gastric implantation site.

In an embodiment, the physical portion of the transluminal apparatus includes a tip of the transluminal apparatus.

In an embodiment, the abdominal cavity apparatus is configured to be coupled to the transluminal apparatus at least during the insertion of the electrode.

In an embodiment, the abdominal cavity apparatus is in contact with the transluminal apparatus at least during the insertion of the electrode.

There is also provided, in accordance with an embodiment of the invention, an implantation system, including:

an electrode, configured for implantation at a gastric implantation site of a patient; and an endoscope configured to provide access to the gastric implantation site, to stabilize itself and the site with respect to each other by using suction, and to facilitate insertion of the electrode into the gastric implantation site.

In an embodiment, the electrode is disposed within the endoscope prior to being inserted into the gastric implantation site.

In an embodiment, a distal tip of the endoscope is configured to be within the stomach, adjacent to the implantation site, when the electrode is inserted into the implantation site.

There is further provided, in accordance with an embodiment of the invention, a method, including:

physically contacting a gastric implantation site of a stomach via a transluminal approach;

physically contacting the site via a transabdominal approach;

stabilizing the site; and implanting an electrode at the site based on the physical contact provided by the transluminal and transabdominal approach.

In an embodiment, stabilizing the site includes inflating the stomach.

In an embodiment, stabilizing the site includes applying pressure to the stomach.

In an embodiment, stabilizing the site includes applying suction.

The present invention will be more fully understood from the following detailed description of embodiments thereof, taken together with the drawings, in which:

BRIEF DESCRIPTION OF THE DRAWINGS

FIG. 5 is a graph showing electrical activity in the fundus of a normal rabbit before and during eating, and results of analysis thereof, in accordance with a typical embodiment of the present invention;

FIG. 6A is a graph showing electrical activity in the fundus of a normal rabbit during and following eating, and results of analysis thereof, in accordance with a typical embodiment of the present invention;

FIG. 6B is a graph showing details of electrical and mechanical activity recorded during the taking of the data shown in FIG. 6A;

FIG. 16 is a schematic illustration of a curved arrangement, in accordance with an embodiment of the present invention;

FIGS. 17A, 17B, 17C, and 17D are schematic illustrations of respective stages in an endoscopic electrode implantation procedure, in accordance with an embodiment of the present invention;

FIGS. 18A, 18B, and 18C are schematic illustrations of respective stages in an endoscopic electrode implantation procedure, in accordance with another embodiment of the present invention;

DETAILED DESCRIPTION OF EMBODIMENTS

Figure 1:
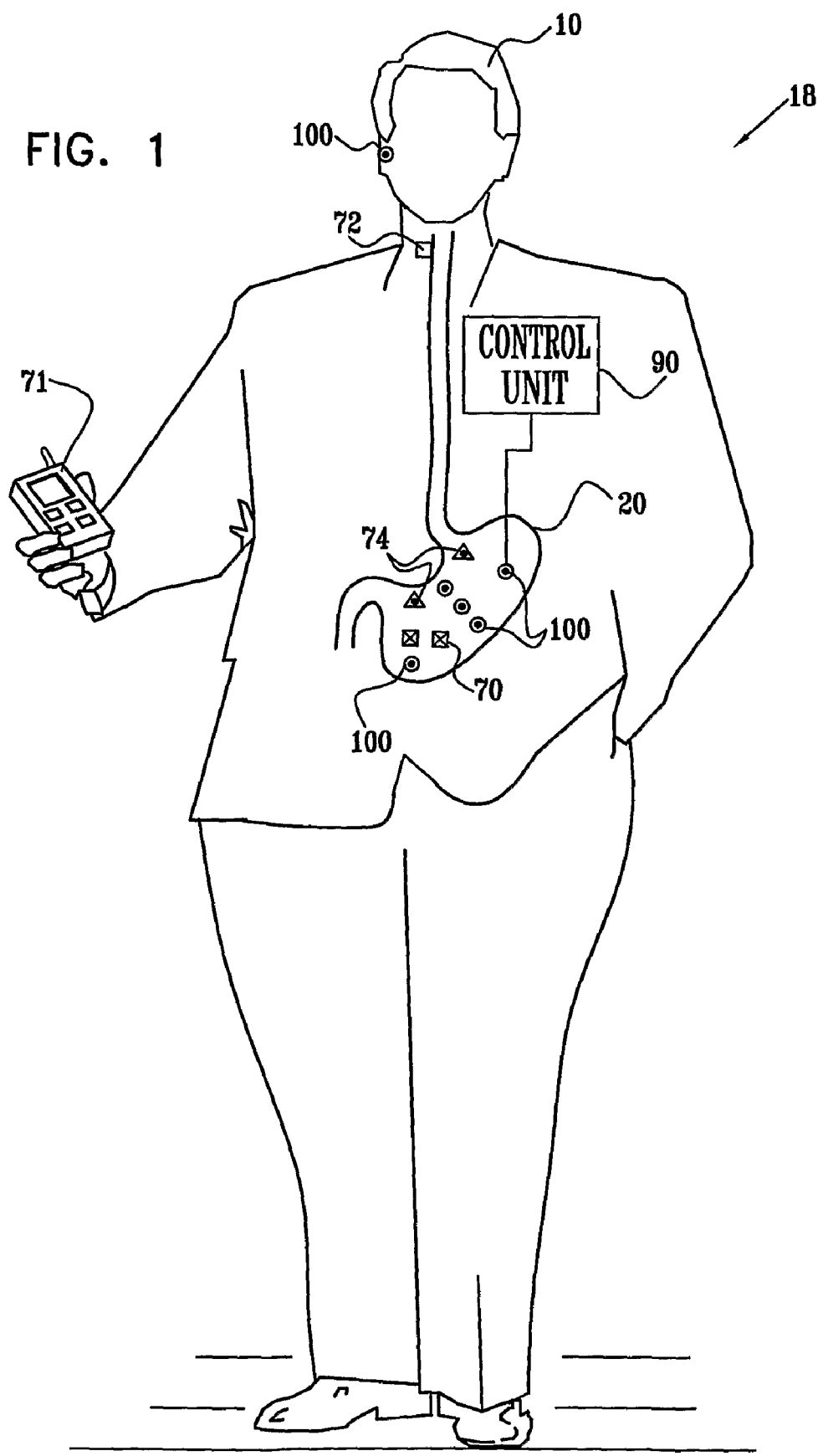
FIG. 1 is a schematic illustration of apparatus for treating obesity, in accordance with a typical embodiment of the present invention.

FIG. 1 is a schematic illustration of diet evaluation apparatus 18, which detects when a patient 10 swallows, and detects the type and amount of matter ingested, in accordance with a typical embodiment of the present invention. Typically, but not necessarily, apparatus 18 additionally determines, responsive to the detection, whether to apply electrical energy to modify the activity of tissue of patient 10. Apparatus 18 typically comprises mechanical sensors 70, supplemental sensors 72, local sense electrodes 74, operator controls 71, and one or more current-application electrodes 100.

Electrodes 74 and 100 are typically coupled to the serosal layer of a stomach 20 and/or inserted into the muscular layer of the stomach in the fundic and antral regions. Alternatively or additionally, the electrodes are coupled elsewhere on the stomach, gastrointestinal tract, or to other suitable locations in or on the patient's body. The number of electrodes and sensors, as well as the positions thereof, are shown in FIG. 1 by way of example, and other sites on stomach 20 or in or on the patient's body are appropriate for electrode and sensor placement in other applications of the present invention. Different types of electrodes known in the art are typically selected based on the specific condition of the patient's disorder, and may comprise stitch, coil, screw, patch, basket, needle and/or wire electrodes, or substantially any other electrode known in the art of electrical stimulation or sensing in tissue.

Typically, apparatus 18 is implanted in patient 10 in a manner generally similar to that used to implant gastric pacemakers or other apparatus for stimulating or sensing in the gastrointestinal tract that are known in the art. As appropriate, techniques described in one or more of the references cited in the Background section of the present patent application may be adapted for use with these embodiments of the present invention. Other methods and apparatus useful in carrying out some embodiments of the present invention are described in the above-cited U.S. Provisional Patent Application 60/259, 925, entitled, "Regulation of eating habits," filed on Jan. 5, 2001, and in the above-cited PCT patent application and in the above-cited U.S. patent application Ser. No. 09/734,358, entitled, "Acute and chronic electrical signal therapy for obesity," filed on Dec. 11, 2000, which are assigned to the assignee of the present patent application and are incorporated herein by reference.

Figure 2:
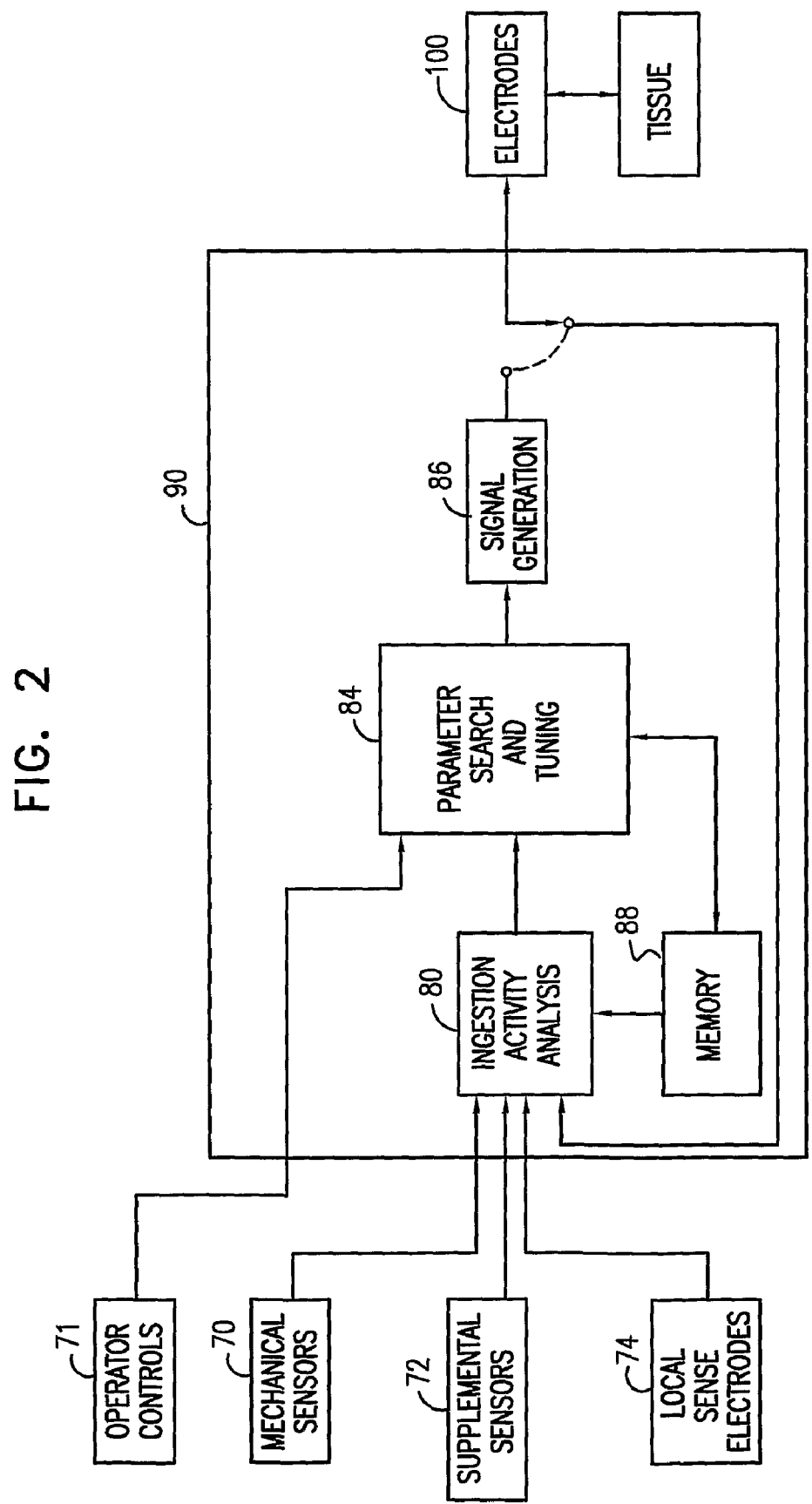
FIG. 2 is a schematic block diagram showing a control unit of the apparatus of FIG. 1, in accordance with a typical embodiment of the present invention.

FIG. 2 is a schematic block diagram illustrating details of operation of a control unit 90 of apparatus 18, in accordance with a typical embodiment of the present invention. Typically, control unit 90 is implanted in patient 10, and receives signals from mechanical sensors 70, supplemental sensors 72, and local sense electrodes 74, all of which are typically implanted on the gastrointestinal tract of the patient or elsewhere on or in the body of the patient. These sensors and electrodes are typically adapted to provide an "ingestion activity analysis" block 80 of the control unit with information about food ingestion and/or the present state of the stomach.

Typically, using techniques described hereinbelow, analysis block 80 determines each time that the patient swallows, and also the character and amount of the ingested matter. For example, local sense electrodes 74 coupled to the fundus of the stomach may send signals indicative of fundic electrical activity to analysis block 80, and analysis block 80 identifies aspects of these signals that are characteristic of swallowing of food by the patient. Additionally, mechanical sensors 70 and local sensor electrodes 74 coupled to the corpus and antral regions of the stomach typically send signals which analysis block 80 identifies as indicative of the onset, duration, and/or intensity of the digestive process in those regions. Typically, these data are utilized by analysis block 80 to determine a quality of the ingested matter, for example, whether it is predominantly solid or liquid. Alternatively or additionally, these data may be used to determine other characteristics of the ingested material, for example, its nutritional, chemical, and/or caloric content.

In a typical embodiment, analysis block 80 determines the time delay between swallowing (as measured, typically, by local sense electrodes 74 on the fundus) and the commencement of electrical and mechanical activity in the antrum. This delay is typically used to differentiate between the ingestion of solid and liquid matter, because solids are generally held in the fundus for at least about 10 minutes before being passed to the antrum, while liquids are generally passed to the antrum essentially immediately.

Alternatively or additionally, the amount of food accumulated in the various regions of stomach 20 is estimated by measuring a level of electrical or mechanical activity in a vicinity of those regions. For example, in some embodiments of the present invention, eating detection is accomplished by monitoring the mechanical impedance of the fundus and the rate of the antral slow waves, whereby an eating event is indicated when both the mechanical impedance of the fundus and the rate of the antral slow waves cross threshold values within a certain time period.

Further alternatively or additionally, analysis block 80 processes data from supplemental sensors 72 indicative of the blood sugar level of the patient, to enable an evaluation of whether and of what type of food has been ingested.

In order to improve the accuracy of the analyses described hereinabove, analysis block 80 is typically calibrated by measuring the appropriate electrical response criteria of stomach 20 of patient 10 to various types of solid and liquid food.

For some applications, analysis block 80 stores the results of its analysis in a memory block 88 of control unit 90, and these results are later uploaded to an external computer, typically by a wireless communications link, for review by the patient's physician. Alternatively or additionally, analysis block 80 conveys results of its analysis of the inputs from mechanical sensors 70, supplemental sensors 72, and local sense electrodes 74, to a "parameter search and tuning" block 84 of control unit 90. The parameter search and tuning block adapts the threshold values indicative of eating by checking that an indicated eating event corresponds to an actual eating event. For example, the parameter search and tuning block may rely on the patient to periodically verify or deny an eating event by using operator control 71. Alternatively or additionally, the parameter search and tuning block utilizes additional sensor information such as antrum impedance, which varies during eating while remaining steady in the absence of eating. In an embodiment, a false positive indication of an eating event may cause one or more of the threshold values to be increased, while a false negative may cause one or more of the threshold values to be decreased.

Alternatively or additionally, search and tuning block 84 is adapted to change one or more of the threshold values in response to a physiological event that has a tendency to cause false indications of eating activity. For example, the migrating motor complex (MMC) is characterized by increased antral electrical activity, which can lead to false indications of eating activity. Since MMC activity lasts about 10 minutes and appears in a cyclical manner with a time lag of about 40 minutes between events, the search and tuning block is adapted to identify MMC activity and respond, such that false positive identifications of eating activity are reduced.

In an embodiment, a calibration period is provided in which a record is generated of actual eating events by the subject. As appropriate, the calibration period may be about one day, several days, or longer than a week. The record of actual eating events may comprise, for example, entries made by the subject or another person in an electronic or non-electronic journal, or using other techniques known in the art for detecting swallowing or otherwise detecting eating. In this embodiment, thresholds for fundic impedance and antral electrical activity are set responsive to (a) the record of actual eating events and (b) measurements of fundic impedance and antral electrical activity made during the calibration period. Typically (but not necessarily), some preference is given to reducing false negatives relative to reducing false positives. In other words, for many applications, it is more important to avoid missing a detection of an eating event than to avoid incorrectly reporting that an eating event occurred. (For other applications, both are of equal importance, or the latter is more important.)

In an embodiment, two parallel matrices are generated in response to the record of actual eating events and the measurements of fundic impedance and antral electrical activity made during the calibration period. The first matrix, a false negative matrix, has a range of thresholds for changes in fundic impedance on the x-axis of the matrix, and a range of antral electrical activity on the y-axis of the matrix. For clarity of description (although not necessarily in practice), the range of fundic impedance extends from normalized values of 1 to 20, and the range of antral electrical activity also extends from 1 to 20. The false negative matrix is then generated as a 20×20 matrix. Each cell in the false negative matrix represents a given combination of possible thresholds of fundic impedance and antral electrical activity. The value stored in a given cell represents a value associated with the extent of false negatives that would have been generated for the given fundic impedance threshold and antral electrical activity threshold represented by that cell. For example, if a normalized fundic impedance threshold of 2 and a normalized antral electrical activity threshold of 7 yielded no false negatives during the calibration period, then the value of the false negative matrix at cell (2, 7) would be zero. Similarly, if a normalized fundic impedance threshold of 20 and a normalized antral electrical activity value of 20 did not result in an identification of any of several actual eating events during the calibration period, then the value of the false negative matrix at cell (20, 20) would be 100%. For some applications, the value of a given cell in the false negative matrix is defined as: 1−(number of correct detections/number of actual eating events).

A corresponding false positive matrix is generated. The x-axis and y-axis of the false positive matrix are analogous to the corresponding axes of the false negative matrix. Typically, the value in each cell of the false positive matrix reflects the total or average number of false positive indications of eating in a given time period (e.g., one day, or throughout the calibration period).

A calibration period analysis algorithm typically identifies one or more near-minimum values in the false negative matrix. These near-minimum values (NMV's) typically are located in one or more "clouds" on the false negative matrix. Similarly, the calibration period analysis algorithm typically identifies one or more NMV's in the false positive matrix. (The term "near-minimum value" is understood to include actual minimum values, as well.) The near-minimum values are typically located in one or more clouds on the false positive matrix, as well. For some applications, in order to determine a suitable fundic impedance threshold and a suitable antral electrical activity threshold for use during regular operation of an eating detection algorithm, the calibration period analysis algorithm first identifies cells in the false negative matrix that are NMV's, and then determines which of the corresponding cells in the false positive matrix are also NMV's.

In some cases, only a single set of fundic impedance and antral electrical activity threshold values (x, y) is an NMV in both the false negative and the false positive matrix. In these cases, this set typically defines the thresholds for use in regular operation of the eating detection algorithm.

In other cases, multiple sets (x(i), y(i)) of thresholds are identified that correspond to an NMV in both the false negative matrix and the false positive matrix. In these cases, for some applications, the calibration period analysis algorithm determines one of the multiple threshold sets that is likely to have a high level of "stability" during regular operation of the eating detection algorithm. To determine stability, the calibration period analysis algorithm typically determines which cell in the false negative matrix having an NMV is not adjacent to or relatively near to one or more cells in the false negative matrix having relatively high values (i.e., indicating many false negatives).

For example, one cell (x1, y1) in the false negative matrix having an NMV of 5% may be relatively near to a second cell (x1−1, y1+2) having an NMV of 30%. Another cell (x2, y2) in the false negative matrix having an NMV of 5% may have no cells within +/−2 on the x-axis or the y-axis having an NMV greater than 25%. In this case, the fundic impedance and antral electrical activity thresholds represented by the second cell would be selected by the calibration period analysis algorithm.

In another example, a summing algorithm typically weighted by proximity is used to evaluate the neighborhood (e.g., +/−3 cells) of all cells having an NMV. The cell that is both NMV and having the lowest "false negative sum" for its neighborhood is selected by the calibration period analysis algorithm to represent the fundic impedance and antral electrical activity thresholds during regular operation of the eating detection algorithm.

For some applications, the stability determination described hereinabove is performed with respect to values in the false positive matrix or with respect to values in both the false positive matrix and the false negative matrix.

In an embodiment, if the calibration period analysis algorithm identifies n cells having stable NMV's in both the false negative and false positive matrices, then during regular operation of the eating detection algorithm, an evaluation of each of the corresponding n sets of fundic impedance and antral electrical activity thresholds is performed. A determination of an eating event is made responsive to some or all of the n sets of thresholds (e.g., responsive to the measured fundic impedance and antral electrical activity exceeding the corresponding thresholds of ½ of the n sets).

Table II and Table III (below) display results obtained based on an experiment with an obese human patient having (a) electrodes implanted on the fundus, for measuring fundic impedance, and (b) electrodes implanted on the antrum, for measuring the rate of antral electrical activity, in accordance with an embodiment of the present invention. During an approximately six hour monitoring period, the patient was free to eat whatever she chose, whenever she chose to eat. During this period, the patient recorded eating three times (pizza bread at 09:45, pasta with cheese at 12:30, and candy at 14:30).

TABLE II

| | Sample false negative matrix | | | | | | | | | | |
|---|---|---|---|---|---|---|---|---|---|---|---|
| | 18 | 18.5 | 19 | 19.5 | 20 | 20.5 | 21 | 21.5 | 22 | 22.5 | 23 |
| 10 | 33 | 33 | 33 | 33 | 33 | 33 | 33 | 33 | 33 | 67 | 67 |
| 12 | 33 | 33 | 33 | 33 | 33 | 33 | 33 | 33 | 33 | 67 | 67 |
| 14 | 33 | 33 | 33 | 33 | 33 | 33 | 33 | 33 | 33 | 67 | 67 |
| 16 | 33 | 33 | 33 | 33 | 33 | 33 | 33 | 33 | 33 | 67 | 67 |
| 18 | 33 | 33 | 33 | 33 | 33 | 33 | 33 | 33 | 33 | 67 | 67 |
| 20 | 33 | 33 | 33 | 33 | 33 | 33 | 33 | 33 | 33 | 67 | 67 |

TABLE II-continued

Sample false negative matrix

| | 18 | 18.5 | 19 | 19.5 | 20 | 20.5 | 21 | 21.5 | 22 | 22.5 | 23 |
|---|---|---|---|---|---|---|---|---|---|---|---|
| 22 | 33 | 33 | 33 | 33 | 33 | 33 | 33 | 33 | 33 | 67 | 67 |
| 24 | 33 | 33 | 33 | 33 | 33 | 33 | 33 | 33 | 33 | 67 | 67 |
| 26 | 33 | 33 | 33 | 33 | 33 | 33 | 33 | 33 | 33 | 67 | 67 |
| 28 | 33 | 33 | 33 | 33 | 33 | 33 | 33 | 33 | 33 | 67 | 67 |
| 30 | [33] | [33] | [33] | [33] | [33] | [33] | [33] | [33] | [33] | 67 | 67 |
| 32 | [33] | [33] | [33] | [33] | *33* | [33] | [33] | [33] | [33] | 67 | 67 |
| 34 | [33] | [33] | [33] | [33] | [33] | [33] | [33] | [33] | [33] | 67 | 67 |
| 36 | [33] | [33] | [33] | [33] | [33] | [33] | [33] | [33] | [33] | 67 | 67 |
| 38 | [33] | [33] | [33] | [33] | [33] | [33] | [33] | [33] | [33] | 67 | 67 |
| 40 | 67 | 67 | 67 | 67 | 67 | 67 | 67 | 67 | 67 | 100 | 100 |
| 42 | 67 | 67 | 67 | 67 | 67 | 67 | 67 | 67 | 67 | 100 | 100 |
| 44 | 100 | 100 | 100 | 100 | 100 | 100 | 100 | 100 | 100 | 100 | 100 |
| 46 | 100 | 100 | 100 | 100 | 100 | 100 | 100 | 100 | 100 | 100 | 100 |

TABLE III

Sample false positive matrix

| | 18 | 18.5 | 19 | 19.5 | 20 | 20.5 | 21 | 21.5 | 22 | 22.5 | 23 |
|---|---|---|---|---|---|---|---|---|---|---|---|
| 10 | 7 | 7 | 7 | 6 | 6 | 4 | 4 | 4 | 4 | 4 | 4 |
| 12 | 5 | 5 | 5 | 5 | 5 | 4 | 4 | 4 | 4 | 4 | 4 |
| 14 | 4 | 4 | 4 | 4 | 4 | 3 | 3 | 3 | 3 | 3 | 2 |
| 16 | 3 | 3 | 3 | 3 | 3 | 3 | 3 | 3 | 3 | 3 | 2 |
| 18 | 3 | 3 | 3 | 3 | 3 | 3 | 3 | 3 | 3 | 3 | 2 |
| 20 | 2 | 2 | 2 | 2 | 2 | 2 | 2 | 2 | 2 | 2 | 1 |
| 22 | 2 | 2 | 2 | 2 | 2 | 2 | 2 | 2 | 2 | 1 | 1 |
| 24 | 1 | 1 | 1 | 1 | 1 | 1 | 1 | 1 | 1 | 1 | 1 |
| 26 | 1 | 1 | 1 | 1 | 1 | 1 | 1 | 1 | 1 | 1 | 1 |
| 28 | 1 | 1 | 1 | 1 | 1 | 1 | 1 | 1 | 1 | 1 | 1 |
| 30 | [0] | [0] | [0] | [0] | [0] | [0] | [0] | [0] | [0] | 0 | 0 |
| 32 | [0] | [0] | [0] | [0] | *0* | [0] | [0] | [0] | [0] | 0 | 0 |
| 34 | [0] | [0] | [0] | [0] | [0] | [0] | [0] | [0] | [0] | 0 | 0 |
| 36 | [0] | [0] | [0] | [0] | [0] | [0] | [0] | [0] | [0] | 0 | 0 |
| 38 | [0] | [0] | [0] | [0] | [0] | [0] | [0] | [0] | [0] | 0 | 0 |
| 40 | 0 | 0 | 0 | 0 | 0 | 0 | 0 | 0 | 0 | 0 | 0 |
| 42 | 0 | 0 | 0 | 0 | 0 | 0 | 0 | 0 | 0 | 0 | 0 |
| 44 | 0 | 0 | 0 | 0 | 0 | 0 | 0 | 0 | 0 | 0 | 0 |
| 46 | 0 | 0 | 0 | 0 | 0 | 0 | 0 | 0 | 0 | 0 | 0 |

An experiment-analysis algorithm was set to have a "refractory" period of 30 minutes following each detection of eating, during which a new detection of eating would not be registered. A "hysteresis" period of 8 minutes was set, whereby a detection of eating would only be made if fundic impedance and antral electrical activity passed respective thresholds within 8 minutes of each other. Lastly, an identified eating detection was counted as being a true eating detection if it occurred within 15 minutes prior to or following the time of eating as recorded by the patient.

The x-axis in Table II (and Table III) represents threshold rates of antral electrical activity, in minutes. The y-axis represents fundic impedance, in ohms. Thus, for example, Table II shows that if the threshold for antral electrical activity were set at 19 seconds (such that only antral electrical activity occurring slower than once every 19 seconds generates an indication of potential eating), and if the threshold for fundic impedance change were set at 16 ohms (such that an indication of potential eating is only generated if the fundic impedance increases by more than 16 ohms), then two actual eating events would have been correctly detected, and one actual eating event would not have been detected. This defines a false negative percentage of 33%.

Similarly, in Table III, the total number of false positive indications of eating are shown in the matrix as a function of particular threshold settings. For example, for a fundic impedance threshold of 19 ohms, and an antral electrical activity threshold rate of 21 seconds, no false positive indications of eating were generated.

Cells in each matrix were automatically analyzed to determine optimal or near-optimal threshold settings for use in regular operation of an eating detection algorithm. Suitable thresholds optimizing both the fundic impedance threshold and the antral electrical activity rate threshold are marked by cells having square brackets surrounding their values. Thus, for this patient, it was found that a fundic impedance threshold ranging from 30 to 38 ohms and an antral electrical activity rate threshold ranging from 18 to 22 seconds is generally optimal. A particular threshold set (32 ohms, 20 seconds) was identified by the automated analysis as being particularly stable (in addition to minimizing false positive and false negative indications), and is marked by a "*".

In an embodiment, the following algorithm and/or pseudocode is executed to determine the fundic impedance and antral electrical activity thresholds. Typically, the identified user would be a physician reviewing records of actual eating events ("bookmarks") and measured data.

1. Input session
    1. User chooses files of data.
    2. For each selected file, allow the user to review the bookmarks and have the following options:
        א.. remove/approve each bookmark
        ב.. accept all bookmarks without reviewing
        ג.. add a bookmark (e.g., to represent an actual eating event not previously recorded)
        ד.. impose a fixed time shift on all bookmarks (e.g., in case the "time stamps" of the bookmarks are not aligned with the time stamps of measurements of fundic impedance
    3. The user will then select the following detection criteria ranges or approve the default:
        א.. Time before and after a meal bookmark that will be considered as a true detection, if detected (default: +/−15 min)
        ב.. Time before and after a meal that will not be considered as a false detection, if a detection is made (default: from 15 min before bookmark to 45 min after bookmark)
2. For all possible rate and impedance thresholds:
Find all "eating detection events," i.e., times during which both the fundic impedance and the rate of slow waves cross their corresponding thresholds in a common time frame, typically 3-10 minutes
Calculate false negative percentage (FN) (percentage of meals that did not have a detection within the pre-defined "true detection time limits"

Calculate false positives per day (FP) (number of detections that did not correspond to an actual eating event, i.e., a bookmark, within the pre-defined "false detection range," divided by the number of days).

3. Identify the "optimal set" of thresholds combination according to the following rule:
   1. Find all threshold pairs (fundic impedance/rate of antral electrical activity) that generate the minimal (or near minimal) false negative percentage.
   2. In this set of threshold pairs, find the corresponding subset with minimal false positives per day. The results of these two steps are defined as the "optimal set"
   4. Find closed spaces of points in the optimal set:
   א.. Set cloud number=1
   ב.. Unmark all points in the optimal set
   ג.. Find the unmarked point in the optimal set that has minimal value of F and R values: $\min_{r,f}\{P(r,f): P \in \text{optimal set}\}$ and mark it
   ד.. Set Rcount=1; Fcount=0;
   ה.. If P(r+count,f+Fcount)∈optimal set then
      1. mark P(r+Rcount; f+Fcount)
      2. Increment Rcount
      3. goto (iv)
      else
         if there is an unmarked point in the range P(r:r+1, f:f+1) that belongs to the optimal set then
            1. set Rcount and Fcount so that r+Rcount and f+Fcount will point to that pair
            2. mark the selected pair
            3. goto iv
         else
            1. set cloud_number=cloud_number+1
            2. define a set cloud (cloud_number) and assign all marked points from the optimal set to it
            3. remove all marked points from the optimal set
            4. goto (iii)
   5. Find cloud's edges
   1. set $P=\min_{r,f}\{P(r,f):P \in \text{cloud}\}$
   2. set count=1
   3. Unmark all F/R matrix members
   4. set $E(count)=\min_{Rcount}(P(r+Rcount,f) \notin \text{cloud})$
   5. mark E(count)
   6. in the range $P(R_{E(count)} \pm 1, F_{E(count)} \pm 1)$ find an unmarked point P∉cloud for which the set $N(R_P \pm 1, F_P \pm 1) \in \text{cloud}$ is not empty
   7. If P exists then
      i. Set count=count+1
      ii. Set E(count)=P
      iii. Goto 5
      Else
         a. in the range $P(R_{E(1)} \pm 1, F_{E(1)} \pm 1)$ find an unmarked point P∉cloud for which the set $N(R_P \pm 1, F_P \pm 1) \in \text{cloud}$ is not empty
         b. if P exists then
            1. Set count=count+1
            2. Set E(count)=P
            3. Goto 5
         iv. Else check if E(1) and E(count) are neighbors
         v. If they are neighbors, then goto 6 else create a set of additional points for the set E according to the following rules:
            1. the number of the points will equal max(abs $(R_{E(1)}-R_{E(count)})$, abs$(F_{E(1)}-F_{E(count)}))$
            2. Each new point will have the FN, FP values of the opposite edge point 6. Grade each point in each cloud
   1. For each cloud
   2. for each P∈cloud
   3. grade(P)=0
   4. for each $E_{count}$ point in E
   5. grade(P)=grade(P)+(FN($E_{count}$)+FP($E_{count}$)/4)/dist(P, $E_{count}$)
   7. Choose the 3 points with minimal grade.
   8. Offer these three combinations to the user, and specify for each of them the values of false negative and false positive it generates.

Figure 3:
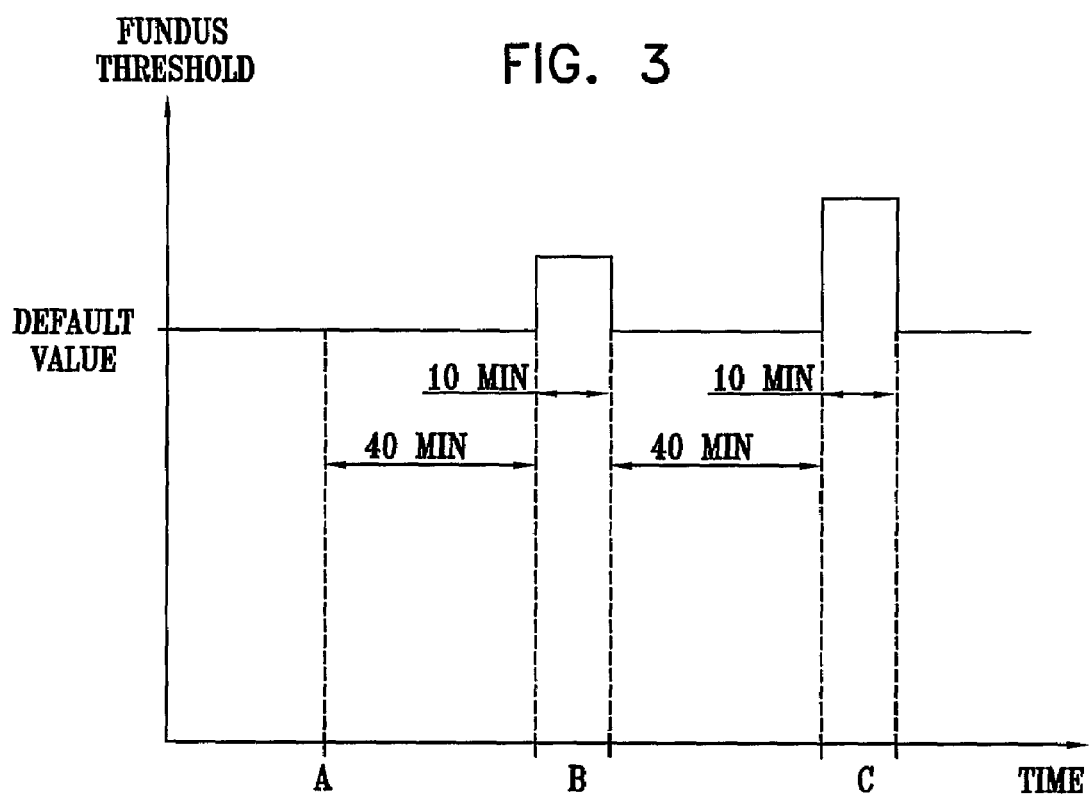
FIG. 3 is a graph showing a default fundus threshold value signifying an eating event, and modifications of the threshold value, in accordance with an embodiment of the present invention.

FIG. 3 is a graph showing an example of a change in a sensing threshold value during suspected periods of MMC activity, in accordance with an embodiment of the present invention. Time period B indicates a time when increased antral electrical activity is detected, which may be indicative of either eating or MMC activity. Search and tuning block 84 then examines data indicating antral electrical activity from 30 to 50 minutes prior to the present activity (i.e., around time A) to determine whether similar activity occurred at time A. If similar activity occurred at time A, the present activity during time period B is of increased likelihood to be related to MMC activity. Therefore, as shown in FIG. 3, the fundus threshold level is increased during time period B, thus reducing the likelihood of false positives relating to MMC activity. In this manner, fundus impedance levels measured prior to time period B generally only need to exceed the default value shown in FIG. 3 in order to produce an indication of eating. Fundus impedance levels during time period B, however, typically need to exceed the elevated threshold in order to produce an indication of eating. Typically, the fundus threshold value is further increased in a subsequent time period C, 30 to 50 minutes after time period B, if antral electrical activity is high during period C, as this is evidence of likely MMC activity. For some applications, other periodic physiological activity of the gastrointestinal tract is treated in a similar manner.

In some other embodiments of the present invention, eating detection is accomplished by monitoring the rate of antral electrical events. Results described hereinbelow show that the rate of antral electrical events typically decreases upon the commencement of eating. For some applications, the reduction of antral electrical events is used in addition to or instead of the techniques described hereinabove for the identification of eating activities. Combining several detection criteria for the onset of eating is typically used to reduce the number of false positives and false negatives.

In an embodiment, the standard deviation of the values of event-to-event time differences are evaluated in a given sliding time window. As appropriate, the events can be detection of electrical activity or mechanical activity in the antrum. The length of the sliding time frame is typically between about 20 seconds and about 2 minutes, but, as appropriate, can be between about 20 seconds and about 10 minutes. In order to detect eating, the measured data are evaluated so as to identify a single event-to-event time difference which is more that 2-3 times the standard deviation of the former events.

With reference to FIG. 2, block 84 evaluates the analysis performed by analysis block 80 with respect to a pre-programmed or variable ingestion schedule stored in memory block 88, so as to determine whether the patient is eating in compliance with a schedule. Typically, the schedule can be modified after implantation of control unit 90, by communication from operator controls 71 using methods described hereinbelow. If it is determined that the patient's eating is not in compliance with the schedule (e.g., the patient has eaten too much at one meal, or has eaten too many meals in a day, or has had too much of a certain type of food or drink), then block 84 typically actuates a signal generator block 86 to generate electrical signals that are applied by current-application electrodes 100 to tissue of patient 10. Block 86 typically comprises amplifiers, isolation units, and other standard circuitry known in the art of electrical signal generation.

The signals generated by block 86 are typically configured so as to induce a response appropriate for controlling the patient's eating habits. For example, block 86 may drive current-application electrodes 100 to apply signals to the stomach that induce gastric dysrhythmia and the resultant feeling of discomfort or nausea. Alternatively or additionally, the signals are applied to an aural site of patient 10 (e.g., in a vicinity of the cochlear nerve or the tympanic membrane), and are configured to induce vertigo, or another unpleasant balance-related sensation. Alternatively or additionally, block 86 generates a visual, audio, or other cue to encourage the patient to adhere to the schedule.

For some applications, control unit 90 drives electrodes 100 to apply a modulation signal to muscle in one area of stomach 20, so as to induce a contraction of the stimulated muscle that, in turn, induces satiety when food in an adjacent area of the stomach causes additional stretching of stretch-receptors therein. This signal may be applied in addition to or instead of the signals described hereinabove that produce gastric or other discomfort. The form of contraction-mediated stretching utilized in these applications simulates the normal appetite-reduction action of the stomach's stretch-receptors, without the patient having eaten the quantities of food which would normally be required to trigger this appetite-reduction response. In a typical application, current-application electrodes 100 are placed around the body of the stomach and are driven to induce a generally steady-state contraction of the corpus, which simulates electrically the squeezing of the corpus produced mechanically by implanted gastric bands known in the art.

Typically, the signals applied by current-application electrodes 100 include, as appropriate, an Excitable-Tissue Control (ETC) signal and/or an excitatory signal that induces contraction of muscles of the stomach. Aspects of ETC signal application are typically performed in accordance with techniques described in the above-referenced PCT Publications WO 99/03533 and WO 97/25098 and their corresponding U.S. national phase application Ser. Nos. 09/481,253 and 09/101,723, *mutatis mutandis*.

Typically, evaluation apparatus 18 includes remote operator controls 71, external to the patient's body. This remote unit is typically configured to enable the patient or his physician to change parameters of the ingestion schedule stored in memory block 88. For example, if the patient has lost weight, the physician may change the ingestion schedule to allow a single mid-afternoon snack. Alternatively or additionally, operator controls 71 comprise an override button, so that the patient may eat outside of the designated meal times, or consume a particular food or drink not in accordance with the schedule, if the need arises. Operator controls 71 typically communicate with control unit 90 using standard methods known in the art, such as magnetic induction or radio frequency signals.

Figure 4:
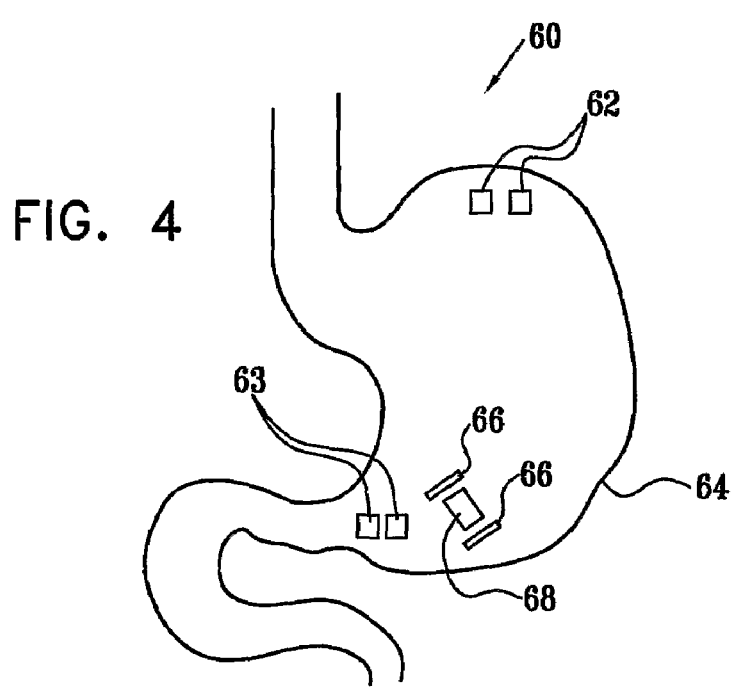
FIG. 4 is a schematic diagram showing experimental apparatus used to measure electrical responses to eating in the stomach of a normal rabbit, in accordance with a typical embodiment of the present invention.

FIG. 4 is a schematic diagram showing experimental apparatus 60 used to measure electrical responses to eating in the stomach 64 of a normal rabbit, in accordance with a typical embodiment of the present invention. Bipolar sense electrodes 62 were coupled to the fundus of stomach 64, and bipolar sense electrodes 63 were coupled to the antrum of the stomach. Additionally, two stitch electrodes 66 with a strain gauge 68 located therebetween were coupled to the antrum.

Reference is now made to FIGS. 5, 6A and 6B, which are graphs showing the results of experiments performed using apparatus 60 in a rabbit, in accordance with a typical embodiment of the present invention. FIG. 5 shows electrical activity in the fundus, measured during a five minute period before the rabbit was fed solid food, and during a more than six minute period while the rabbit was eating solid food. It can be seen that the second period is distinguished by markedly increased electrical activity. Spikes, typified by those marked "A," "B," and "C" in this graph, are typically identified by a control unit operating in accordance with these embodiments of the present invention, and are interpreted as indications of eating. It is noted that in the case of the rabbit experiment shown in FIG. 5, electrical activity as measured by spikes per unit time increased by a factor of about 8, and is therefore considered to be a good indication of the initiation and continuation of eating.

FIG. 6A is a graph showing the electrical response of the fundus of the rabbit stomach, and the results of analysis thereof, in accordance with an embodiment of the present invention. In this experiment, the measurements were first taken for five minutes while the rabbit was eating solid food, and were continued for almost 10 minutes after the rabbit ceased eating. It is clearly seen that the period after the rabbit ate is characterized by significantly less electrical activity than that which occurred during eating. Spikes, such as those marked "A," "B," and "C" in this graph, occur at a rate at least 15 times higher during eating than thereafter, and are therefore typically used by a control unit to determine both the onset and the termination of eating.

FIG. 6B is an expanded view of some of the data shown in FIG. 6A, additionally showing simultaneous mechanical and electrical activity in the antrum of the rabbit. The top graph shows mechanical activity in the antrum as measured by strain gauge 68 (FIG. 4), and the middle graph shows electrical activity in the antrum, measured by electrodes 63 during the same time period. The repeated co-occurrence of antral mechanical and electrical activity, as seen in FIG. 6B, is indicative of the expected antral mechanical response to antral electrical activity.

The bottom graph of FIG. 6B shows the measured electrical activity in the fundus during the same period, i.e., while the rabbit was eating. It can be seen that, while there is close correlation between mechanical and electrical activity in the antrum, there is not such a close correlation between fundic electrical activity and either measure of antral activity. Control unit 90 (FIG. 2) is therefore generally enabled to measure and differentiate between fundic and antral response, and to utilize this information to facilitate the evaluations and determinations described herein.

Figure 7:
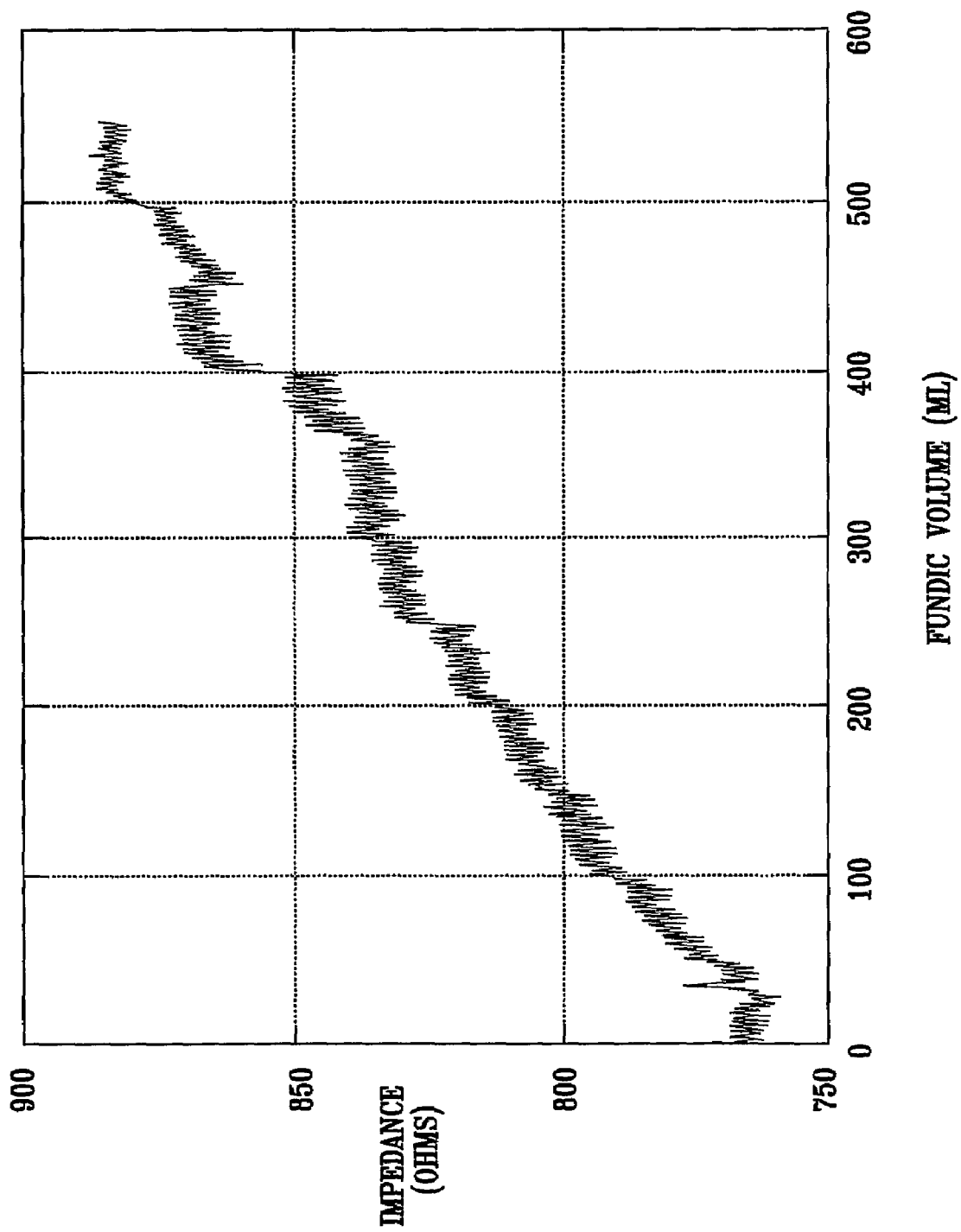
FIG. 7 is a graph showing detail of electrical fundic activity, measured in accordance with a typical embodiment of the present invention.

FIG. 7 is a graph showing electrical impedance measurements made between two stitch electrodes placed in the stomach of a pig, in accordance with an embodiment of the present invention. In this experiment, fundic volume was measured at the same time as the impedance was measured, and the data show a clear dependence of the impedance on the volume. It is hypothesized that as the fundus distends, the fundic wall thickness decreases, producing a corresponding increase in electrical impedance. Alternatively or additionally, the increased distance between the two electrodes produced as a result of the distension causes the electrical impedance to increase. Similar experimental results (not shown) were obtained when impedance and volume measurements were made in the antrum. Moreover, changes in impedance were found to correlate with waves of antral activity.

Reference is now made to FIGS. 8, 9, 10, and 11, which are graphs showing the results of experiments performed using apparatus (not shown) similar to apparatus 60 in several normal dogs, in accordance with a typical embodiment of the present invention. All of the dogs fasted for approximately 24 hours prior to eating during the experiments.

Figure 8:
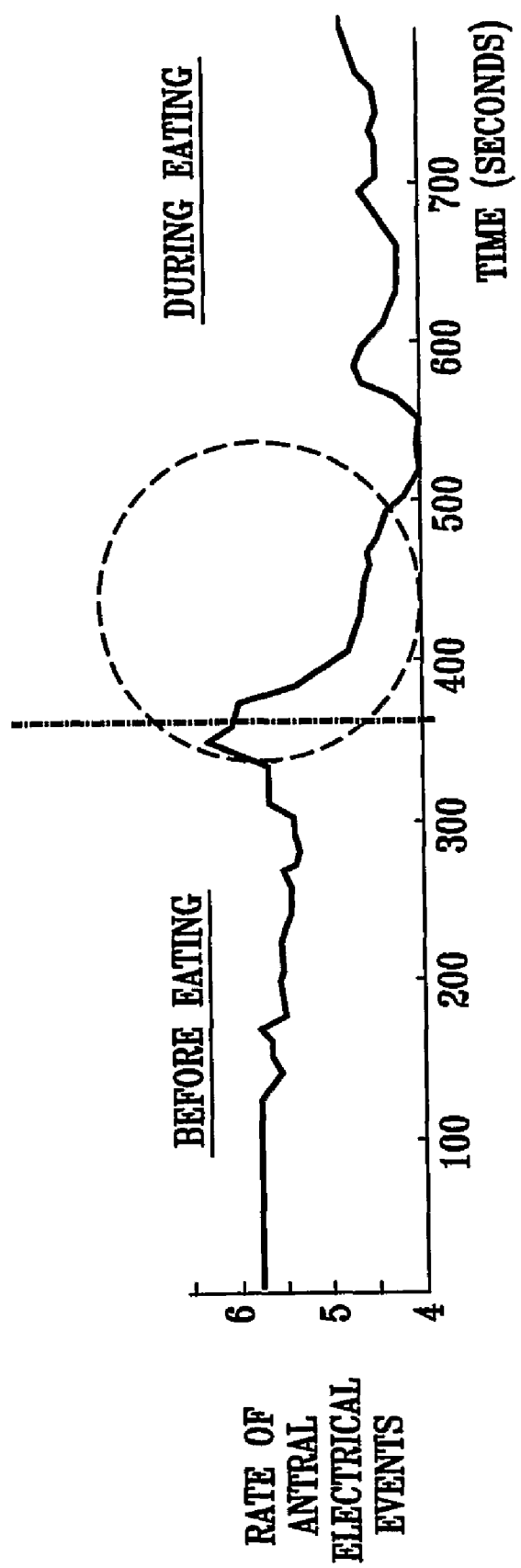
FIG. 8 is a graph showing the rate of electrical events in the antrum of a normal dog before and during eating, and results of analysis thereof, in accordance with a typical embodiment of the present invention.

FIG. 8 shows the rate of electrical events in the antrum in a dog, measured during a six minute period before the dog was fed solid food and during a more than seven minute period while the dog was eating solid food. Electrical events that were recorded were spikes in the signal of amplitude at least a threshold amount greater than the signal noise. It will be appreciated that detecting changes in other events may be useful for some applications. It will also be appreciated that whereas data shown in the figures reflects measurements of antral electrical events, for some applications the analysis techniques described herein may also be implemented with respect to the rate of fundic electrical events.

It can be seen that the second period is distinguished by a markedly decreased rate of antral electrical events. Such a decrease is typically identified by a control unit operating in accordance with these embodiments of the present invention, and is interpreted as an indication of eating. It is noted that the rate of antral electrical events, as measured by events per unit time, decreased on average by about 20% beginning about one minute after the initiation of eating, and is therefore considered to be a good indication of the initiation and continuation of eating. (Decreases of up to about 50% were seen in other experiments.) Alternatively or additionally, responsive to a calibration procedure, such a decrease in the rate of antral electrical events may be used to determine other characteristics of the ingested material, for example, its nutritional, chemical, and/or caloric content. Similar results were obtained in experiments on two other dogs (not shown).

Figure 9:
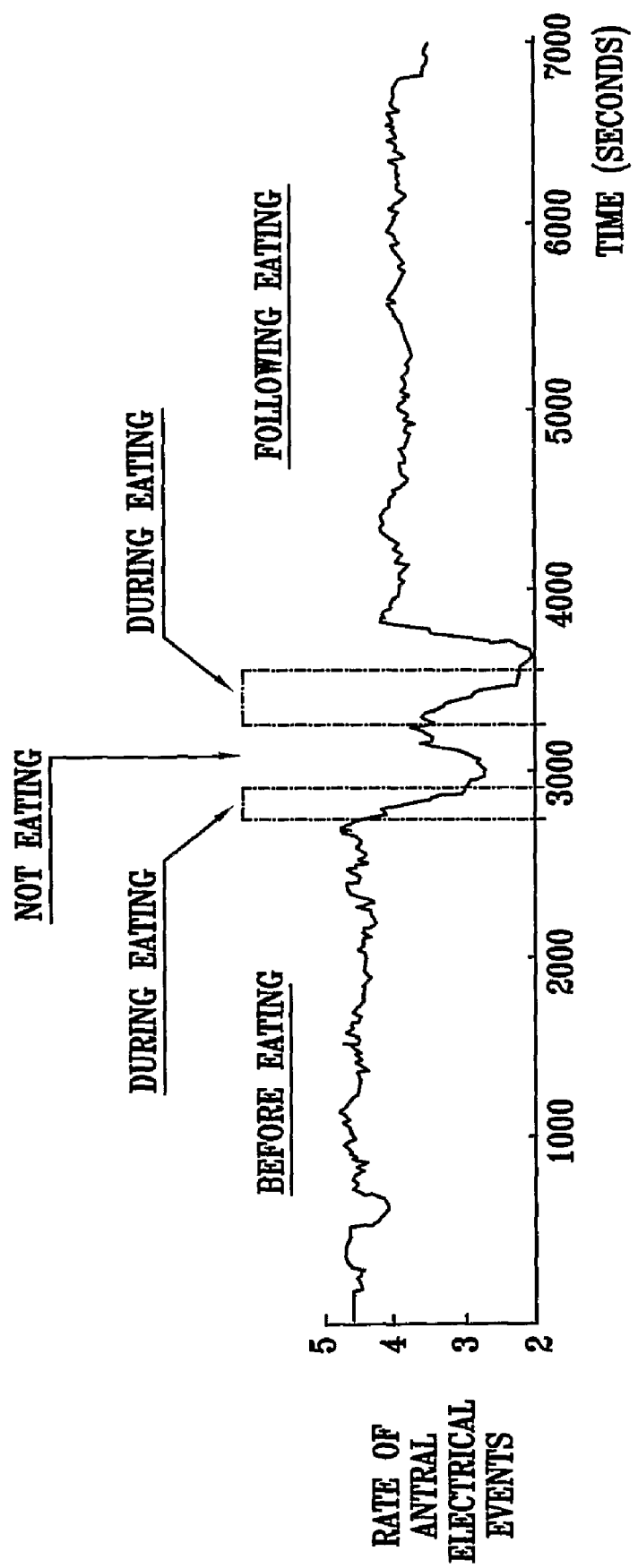
FIG. 9 is a graph showing the rate of electrical events in the antrum of a normal dog before, during, and after eating, and results of analysis thereof, in accordance with a typical embodiment of the present invention.

FIG. 9 is a graph showing the rate of electrical events in the antrum in a second dog, measured during a more than 40 minute period before the dog was fed solid food, during an approximately 13 minute period while the dog was eating solid food (interrupted by an approximately 6 minute period of non-eating), and during an almost 60 minute period after the dog ceased eating. It is clearly seen that the period beginning approximately four minutes after the dog ceased eating is characterized by return to a rate of antral electrical events almost equal to the rate prior to eating, and significantly higher than the reduced rate during eating. The rate of antral electrical events is therefore typically used by a control unit to determine both the onset and the termination of antral activity.

Figure 10:
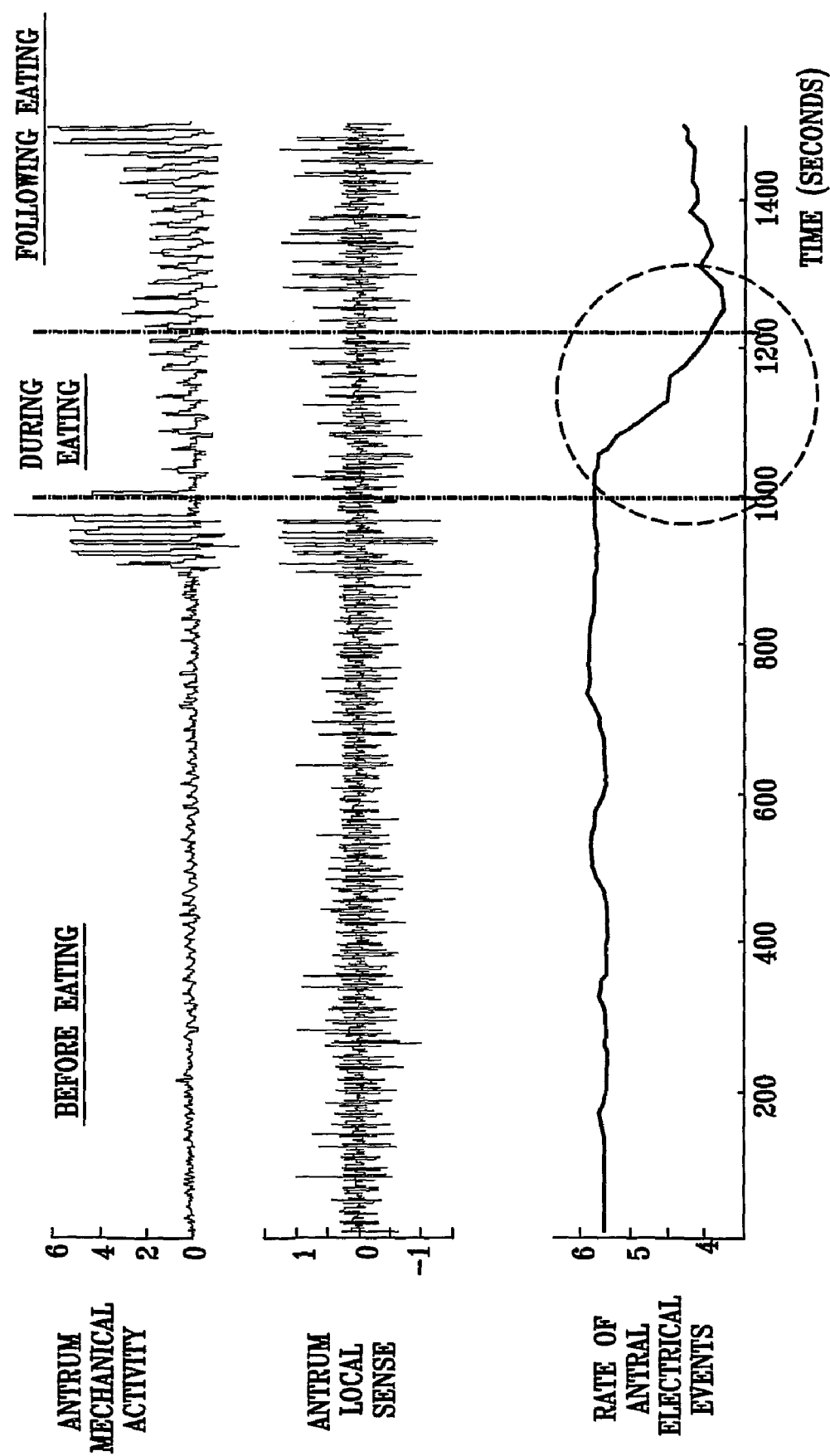
FIG. 10 is a graph showing electrical and mechanical activity and the rate of electrical events in the antrum of a normal dog before, during, and after eating, and results of analysis thereof, in accordance with a typical embodiment of the present invention.

FIG. 10 is a graph showing simultaneous mechanical activity, electrical activity, and rate of electrical events in the antrum of a third dog, measured during a more than 16 minute period before the dog was fed solid food, during an approximately 3.5 minute period while the dog was eating solid food, and during a more than four minute period after the dog ceased eating. The top graph shows mechanical activity in the antrum as measured by a strain gauge, and the middle graph shows electrical activity in the antrum, measured by electrodes during the same time period. It can be seen that co-occurring mechanical and electrical activity began approximately 1.5 minutes prior to the beginning of eating, corresponding with the onset of cephalic phase activity (brain activity reflecting the mental anticipation of eating).

The bottom graph of FIG. 10 shows the rate of electrical events in the antrum of the dog. It can be seen that the second period is distinguished by a markedly decreased rate of antral electrical events, consistent with the results of the first dog experiment described hereinabove. An increase in mechanical and/or electrical antral activity prior to eating as occurred in this experiment is typically identified by a control unit operating in accordance with these embodiments of the present invention, and provides additional information that can be interpreted together with information such as the decreased rate of antral electrical events observed in this experiment to provide indications of anticipation of eating, eating and/or gastric digestion.

Figure 11:
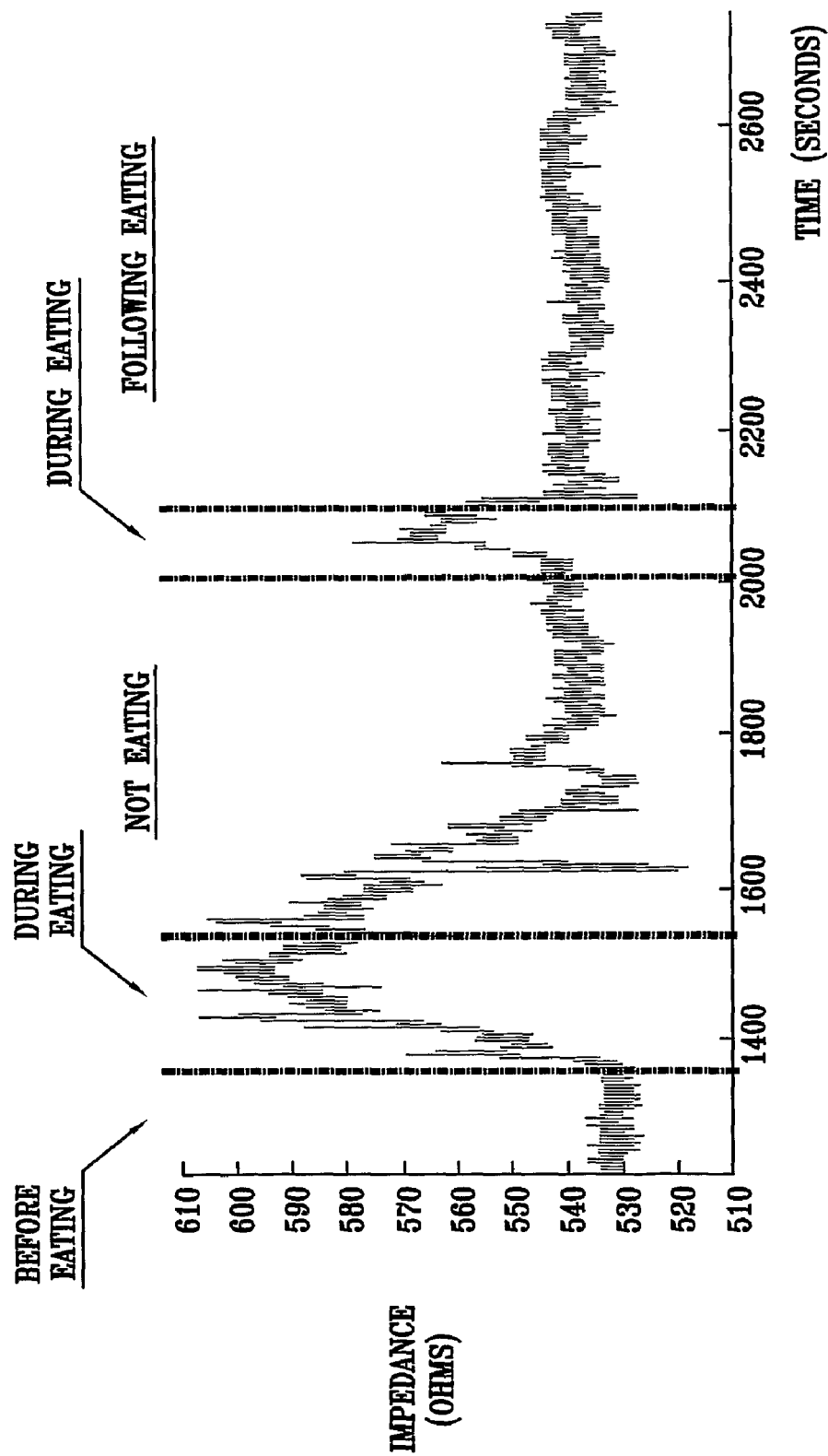
FIG. 11 is a graph showing fundic electrical activity in a normal dog during several periods of eating and non-eating, and results of analysis thereof, in accordance with a typical embodiment of the present invention.

FIG. 11 is a graph showing electrical impedance measurements made between two stitch electrodes in the fundus of a fourth dog, measured during five sequential periods: (1) an approximately 22 minute period before the dog was fed solid food (portion of period not shown), (2) an approximately three minute period while the dog was eating solid food, (3) an approximately 7.5 minute period during which the dog did not eat, (4) an approximately one minute period while the dog was eating solid food, and (5) a greater than 10 minute period after the dog ceased eating.

It can be seen that the eating periods (second and fourth periods) are distinguished by markedly increased fundic electrical impedance. Such increases are typically identified by a control unit operating in accordance with these embodiments of the present invention, and are interpreted as indications of eating. This interpretation is supported by the correlation between impedance and volume measurements in the fundus obtained in the pig experiments described hereinabove. It is noted that in the case of the dog experiment shown in FIG. 11, the fundic electrical impedance, as measured in ohms, increased by more than about 12%, beginning less than about one minute after the initiation of eating during the second period, and by about 5% beginning less than about one minute after the initiation of eating during the fourth period. The fundic electrical impedance is therefore considered to be a good indication of the initiation and continuation of eating. Similar results were obtained in two other experiments on different days on the same dog (not shown).

It is clearly seen in FIG. 11 that the period beginning almost immediately after the dog ceased eating (the fifth period) is characterized by a return of fundic electrical impedance to a value almost equal to that prior to eating, and significantly lower than the increased value observed during eating. Fundic electrical impedance is therefore typically used by a control unit to determine both the onset and the termination of eating.

The inventors have observed that fundic electrical impedance (e.g., as measured in the case of the dog experiment shown in FIG. 11), as an indicator of eating, typically exhibits lower variability than antral electrical impedance, and is less affected by movement and/or change in posture of the subject. Fundic electrical impedance also typically provides more reliable detection of eating than antral activity.

In typical embodiments of the present invention, measurements of antral and/or fundic electrical impedance are used in conjunction with or separately from other indicators of swallowing or digestion, described hereinabove, in order to track a patient's eating habits. Advantageously, impedance measurements made between two electrodes located even at mutually remote sites on a portion of the stomach can be accurate indicators of global strain of that portion, while a mechanical strain gauge placed at a particular site on the stomach generally only yields an indication of strain at that site.

It will be recognized by persons skilled in the art that more complex combinations of variations in levels of electrical or mechanical activity in different regions of the stomach may occur than those demonstrated in the experiments described hereinabove. For example, certain electrical or mechanical activity may lag the eating of certain amounts and types of food. Examples of more complex combinations (not shown) were obtained in additional experiments in other dogs. Analysis block 80, with proper calibration as described hereinabove, can readily be enabled to evaluate such complex combinations.

Figure 12:
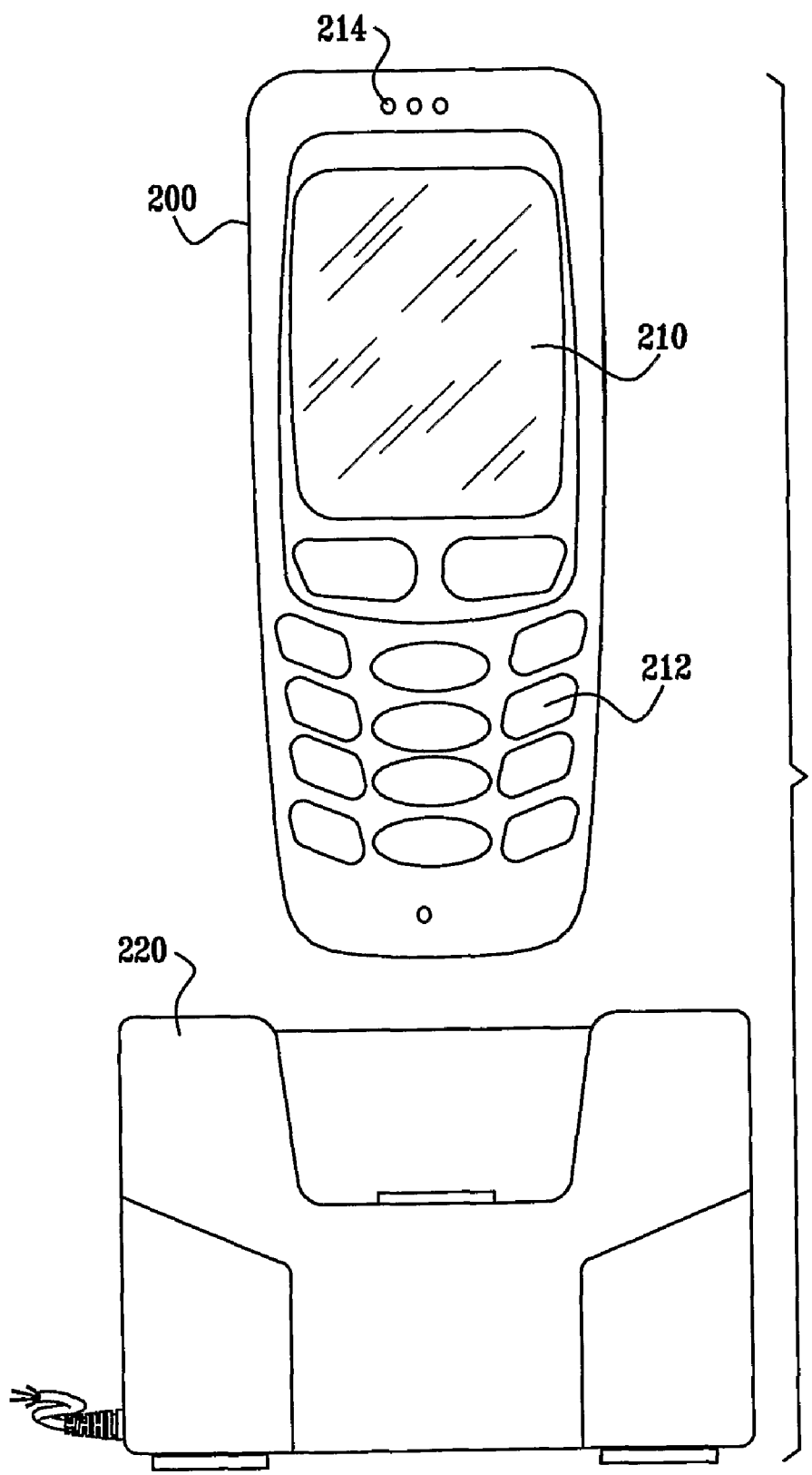
FIG. 12 is a schematic illustration of a portable control charger, in accordance with an embodiment of the present invention.

Reference is now made to FIG. 12, which is a schematic illustration of a portable control charger 200, in accordance with an embodiment of the present invention. In this embodiment, control unit 90 of apparatus 18 further comprises:

(a) a replenishable power source, e.g., a rechargeable battery, which requires periodic recharging, e.g., at least once per week;

(b) recharging circuitry;

(c) at least one coil for inductively receiving externally-generated energy (e.g., RF energy), or another element for receiving energy, such as an e-field antenna, a photovoltaic cell, or an ultrasound transducer; and (d) an antenna for transmitting and/or receiving data.

For some applications, a single set of at least one coil both receives the externally-generated energy and transmits/receives the data.

Control charger 200 typically functions as operator controls 71, described hereinabove with reference to FIGS. 1 and 2, receiving data from and sending data to control unit 90. In addition, control charger 200 is adapted to inductively charge the rechargeable batter of control unit 90.

Control charger 200 typically comprises various input/output elements, such as a display screen 210, a keypad or keyboard 212, and a speaker 214. Control charger 200 also comprises a rechargeable battery, which is typically recharged using standard household AC current, such as via an AC-powered recharging cradle 220, similar to conventional portable telephone recharging cradles. Control charger 200 further comprises at least one coil for inductively transmitting energy to the coil of control unit 90, and an antenna for transmitting data to and/or receiving data from control unit 90. For some applications, a single set of at least one coil both transmits the energy and transmits/receives the data.

In addition to its charging functionality and the functionality of operator controls 71, control charger 200 is typically programmed (in hardware and/or in software) to have functionality related to the patient's eating habits and/or weight loss program. Such functionality optionally utilizes data received from control unit 90, and/or transmits data to control unit 90. Such functionality typically includes one or more of the following:

personal digital assistant (PDA) functionality, e.g., a program for helping the patient keep a record of and/or modify his eating habits. For some applications, data received from control unit 90 are used by the program. For example, the program may record and display the number of meals or quantity of food consumed each day, and give encouraging messages when the number of meals or quantity of food is in compliance with a prescribed eating program. For some applications, the patient maintains a meal log, by keying meal details into keypad 212;

connectivity to a scale, for inputting measurements of the patient's weight. For some applications, a graph of the patient's weight is displayed next to a graph of the number of meals or quantity of food consumed during the same time period, in order to encourage the patient to be in compliance with a prescribed eating program;

glucose monitoring, such as for diabetic patients. For some applications, monitored glucose levels are displayed in conjunction with detected meals, in order to intermittently make the patient aware of how his eating behavior affects an important parameter of health. The blood glucose monitor may be integrated in the charger or control unit 90, or external thereto;

body composition monitoring, measured by control unit 90 or by an external gauge. An example of body composition monitoring is body fat monitoring, e.g., using a body fat caliper;

body size monitoring, e.g., by tracking the circumference of the patient's waist, biceps, thigh, calf, chest, etc.;

heart rate, ECG, oxygen saturation, respiratory peak flow, and/or blood pressure monitoring, which may be integrated in the charger or control unit 90, or external thereto;

monitoring of time or energy invested in exercise, e.g., via a home treadmill or bicycle (typically but not necessarily externally wired to the charger). Alternatively or additionally, an implanted accelerometer monitors body movement, thereby giving an indication of overall physical activity;

monitoring of gastric slow wave rate (e.g., fasting and fed) and/or gastric contraction amplitude (e.g., fasting and fed). This monitoring is typically performed by control unit 90;

connectivity to a remote service provider, such as over a wireless or wired connection, for sending data to or receiving data from the service provider. This connectivity is optionally obtained via cradle 220. In an embodiment, the remote service provider:

a) tracks the patient's eating habits for analysis by a healthcare worker (e.g., dietitian or physician);

b) sends recommendations to control charger 200 for the patient, such as for display on display screen 210. Such recommendations may be patient-specific, such as determined based on analysis of the patient's eating habits, and may include recommendations for specific dietetic foods or recipes. Such recommendations may also be commercial in nature; and/or c) sends reminders to the patient, e.g., regarding setting or going to healthcare appointments, or attending weight-related support group meetings;

displaying system parameters such as time from last battery charge, last known battery voltage, estimated current battery voltage level; and/or displaying average number of eating detections per day and/or a total amount of time each day that control unit 90 applies stimulation to the stomach.

In an embodiment, the charger alerts the patient's physician if the patient has not charged the implanted device in accordance with a recommended schedule. In this case, the physician may call the patient to remind the patient to be compliant with the recommended schedule.

For some applications, glucose monitoring, patient weight data, and/or another external feedback mechanism is used to provide feedback to the patient and/or automatically change a parameter of stimulation. For example, in response to feedback indicating that the patient has attained a desired weight, or is losing weight more quickly than desired, a level of intensity of the stimulation may be lowered, so as to reduce an intensity of the induced sensation or satiety or discomfort.

For some applications, glucose monitoring, patient weight data, and/or another external feedback mechanism is used to automatically change a mode of stimulation. For example, in response to an indication that blood glucose levels are at a desired level, control unit 90 may switch operation of the implanted apparatus from a glucose-level-control mode of operation to an early-satiety-induction (and typically weight-loss-induction) mode of operation. Similarly, if a desired patient weight or rate of weight loss has been attained, then control unit 90 may enter the glucose-level-control mode of operation, or increase the relative amount of time that it is in the glucose-level-control mode of operation compared to the early-satiety-induction mode of operation. As appropriate, the glucose-level-control mode of operation may be such as to: (a) induce an acute reduction of glucose level (e.g., post-prandial glucose level), and/or (b) induce a chronic reduction of glucose level (e.g., as indicated by a fasting glucose level of the patient).

For some applications, control unit 90 receives, from a PDA or other input device, an indication of a particular eating behavior of the patient, and sets an eating detection parameter responsive to the indicated eating behavior. For example, the indicated behavior may include an indication by the patient that he is on a particular eating regimen (e.g., a high protein diet, a low fat diet, a low carbohydrate diet, or a popular diet program, such as the Atkins diet). For some patients, control unit 90 is programmed to regulate a threshold of an eating detection algorithm in response to expected eating behaviors of the patient. For example, in response to a particular diet, a patient or a group of patients may demonstrate modulated intensity or timing parameters of fundic or antral activity, and control unit 90 may be programmed to automatically modify corresponding thresholds in its eating detection algorithm responsive to the effect of the particular diet on the fundic or antral activity.

Alternatively or additionally, control unit 90 receives, from a PDA or other input device, an indication of a particular eating behavior of the patient, and sets a stimulation parameter responsive to the indicated eating behavior.

For some applications, a financial incentive is provided to the patient, based on a measurement of success such as a magnitude of weight loss and/or a rate of weight loss. For example, a patient may receive a coupon to a clothing store or a health food store in response to losing a certain amount of weight in a week.

For some applications, some or all of the data types described above, and/or personal data of the patient (such as a standard medical record) are stored in the implantable device, and may be modified and/or read by an external programmer such as charger 200 or by a customized reading device. For some applications, such personal data are used to improve patient care, e.g., for a patient admitted to a hospital, or for a patient being admitted to a hospital. Alternatively or additionally, the personal data are used to facilitate giving financial incentives to the patient. For example, virtual coupons may be stored in charger 200 or in another device, and physiological data or other collected data may be used to calculate a coupon value for the patient based on the patient's achievements and/or improvements. For some applications, techniques described herein are performed using data stored in charger 200 as well as patient records or other records stored on a server of a healthcare provider.

For some applications, functionality described herein with respect to a charger is embodied in an external device that does not charge control unit 90. For example, such an external device may comprise a cash register in a store, which comprises a reader capable of reading at least some of the personal data stored in the implantable device for the purpose of delivering or receiving virtual coupons or delivering another financial incentive.

For some applications, techniques described herein with respect to treatment of obesity are applied, alternatively or additionally, in the treatment or tracking of another medical condition, such as congestive heart failure (CHF), diabetes, hypertension, snoring, sleep apnea, or a disorder related to the nervous system (e.g., epilepsy, pain, motor dysfunction, or a psychiatric disorder). For example, the techniques described herein may be adapted to provide evaluation and/or monitoring of disease progression, by providing suitable data transfer between an implantable device and an external data logger (e.g., embodied in a charger like charger 200).

For example, apparatus comprising an implantable cardiac-treatment device and an external data logger (e.g., embodied in a charger like charger 200) may comprise any of the functionalities described hereinabove with respect to charger 200 and control unit 90, mutatis mutandis, and/or one or more of the following:

patient activity sensors, e.g., sensors for measuring motion, walking distance, coughing, and/or sleeping of the patient. Such sensors may be used, for example, to facilitate generation of a patient-viewable output correlating gradual increases in daily walking with gradual improvement of a parameter related to heart failure; and internal or external sensors and an analysis unit, for identifying changes in one or more heart-related parameters, such as heart rate variability (typically reduced when heart failure progresses), breathing sounds, ST segment elevation (e.g., as an indirect indication of cardiac ischemia), heart rate elevation, aortic flow (e.g., measured using echo- or impedance-based techniques), dp/dt, or dZ/dt.

As appropriate based on the type of data collected, statistics are typically generated (e.g., hourly, daily, or weekly statistics), and a summary is presented to the patient and/or transmitted to the patient's physician or to a remote data collection center.

For some applications, changes in thoracic electrical impedance are measured and presented to the patient and/or transmitted to the patient's physician or to a remote data collection center. The measurements are used as an indication of changes in thoracic fluid volume, and may be used to facilitate earlier clinical assessment of changes in the patient's state (e.g., worsening CHF), and/or to initiate a behavior-modification program for the patient.

In an embodiment, techniques for data logging, analysis, and transmission, and activities subsequent thereto, are applied with respect to modifying a therapy performed using an intra-body device, such as a pacemaker, ICD, ventricular assist device, or electrical cardiac contractility modulation device (as are known in the art). Alternatively or additionally, techniques for data logging, analysis, and transmission, and activities subsequent thereto, are applied with respect to modifying a therapy performed without using an intra-body device, such a drug therapy.

It is thus to be appreciated that techniques described hereinabove with respect to obesity may be applied, *mutatis mutandis*, with respect to the treatment of cardiac conditions. For example, an external data logger (e.g., incorporated in a charger) may be used to track overall activity levels of a patient via an implanted accelerometer, and to provide virtual coupons to the patient in response to activity levels that are indicative of the patient following a prescribed exercise regimen.

For some applications, techniques described hereinabove with respect to obesity and/or cardiac conditions are applied, *mutatis mutandis*, to the treatment of diabetes. For example, tracking of changes in the condition of a diabetic patient may be facilitated by communication of data between an external data logger and one or more of the following: (a) an implanted pancreatic stimulator, (b) a sensor implanted on the pancreas, (c) an implanted blood constituent sensor (e.g., a blood glucose sensor), or (d) an implanted sensor that detects changes in state of the GI tract.

In an embodiment, incentives are provided to a diabetic patient for following a prescribed health regimen. The health regimen may include, for example, a diet regimen, an exercise regimen, or a behavior regimen (e.g., measuring blood glucose levels a prescribed number of times per day). Alternatively or additionally, the incentives may be provided based upon attainment of a health goal, or one in a series of interim health goals. Such health goals may include, for example, a peak daily blood glucose level that is lower than a prescribed level, an average blood glucose level that is lower than a prescribed level, or a level of weight loss that is in accordance with a prescribed weight loss plan.

It is noted that techniques described separately with respect to obesity, diabetes, hypertension, cardiovascular disease, snoring, and sleep apnea may be performed together. For example, weight data collected with respect to treating obesity may be used, additionally, in the treatment of diabetes or a cardiovascular disease of the patient.

It is noted that coupons are described herein by way of illustration and not limitation, and that the scope of the present invention includes other forms of financial and non-financial incentives, as well (e.g., tax rebates, reduced health insurance premiums, workplace rewards, eligibility for participation in health-related programs or non-health-related programs, and free entrance to theaters or other places of entertainment).

Figure 13:
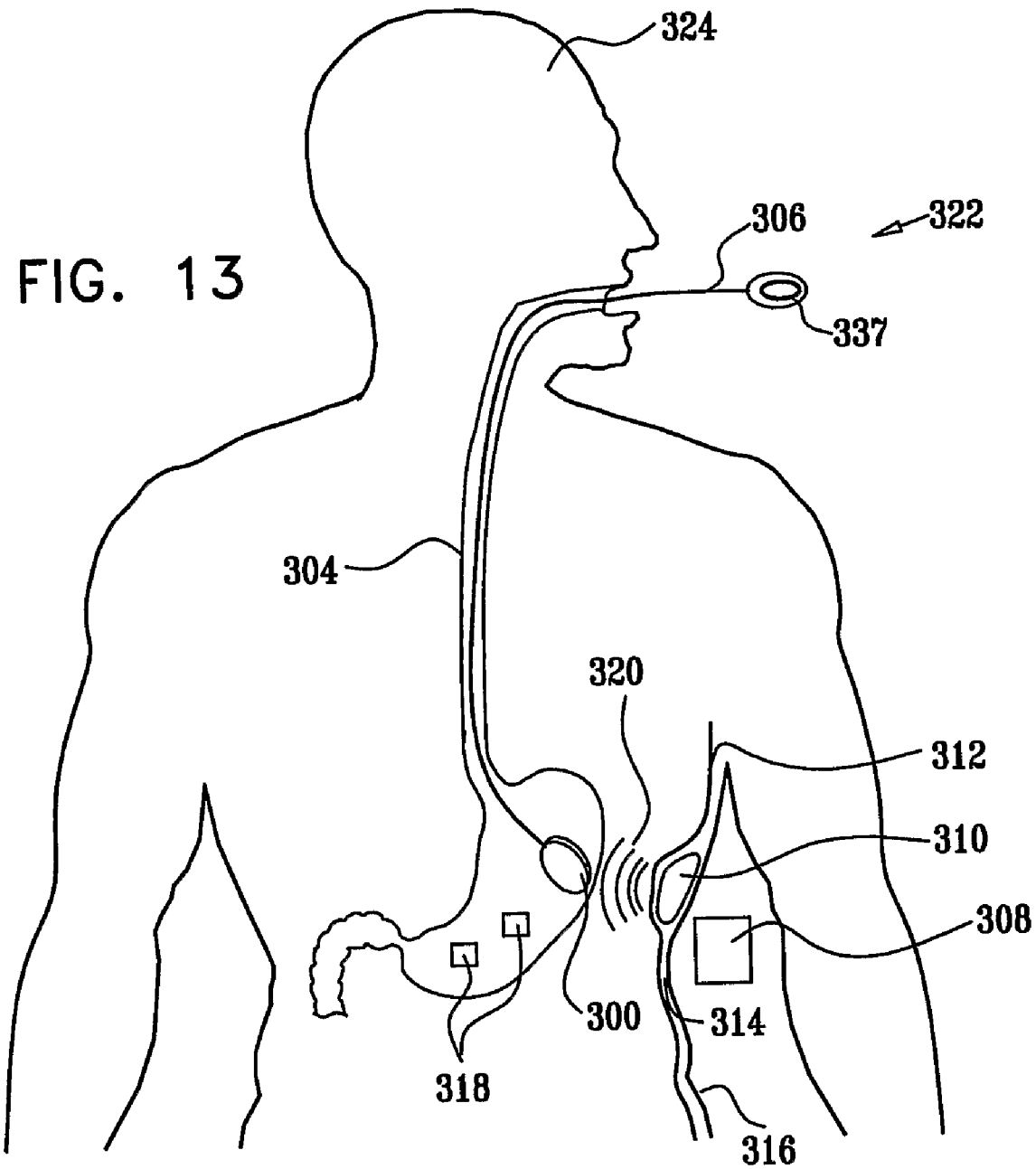
FIG. 13 is a schematic illustration of an endoscopically-implanted system, in accordance with an embodiment of the present invention.

FIG. 13 is a schematic illustration of an endoscopically-implanted system 322, in accordance with an embodiment of the present invention. An endoscope 306 comprising endoscopic controls 337 is inserted into the esophagus 304 of a patient 324. In some embodiments of the present invention, an endoscopic tool, such as endoscope 306, is used to couple a wireless device to the stomach of a patient. Typically, but not necessarily, the wireless device may be configured as a stimulation device, for example, comprising one or more wireless electrodes 318 configured to be used as part of a diet evaluation and/or regulation apparatus, similar to the diet evaluation and/or regulation apparatus described herein. It is therefore noted that although some embodiments of the present invention are described herein with respect to electrodes that are implanted during abdominal surgery to the stomach and connected via wires to a control unit, the scope of the present invention is not limited to such a configuration. FIG. 13 shows a time point when two electrodes 318 have been implanted on the stomach, and an electrode implantation tool 300 is about to implant a third electrode on the stomach.

For some applications, the extent of surgical intervention utilized to implant the diet evaluation and/or regulation apparatus is reduced by delivering the electrodes to the stomach using endoscope 306. A control unit 310 is typically implanted in the adipose tissue between the skin 316 and fascia 312 of the patient, but the abdominal cavity itself is not typically opened.

Typically, electrodes 318 endoscopically implanted on the stomach do not contain their own long-term power supplies. Instead, control unit 310 is adapted to drive the electrodes of the apparatus via electromagnetic radiation 320, but other wireless communication and powering techniques are within the scope of the current invention. In some embodiments of the present invention, the same frequency band of electromagnetic radiation is used to both control and provide power to electrodes 318 on the stomach. Alternatively, separate frequency bands are used for controlling and powering the electrodes. In some embodiments of the present invention, separate frequencies of the electromagnetic spectrum, and/or or coding techniques known in the art are used to control the various electrodes, such that individual control of each electrode can be achieved. Typically, control unit 310 drives electrodes 318 so that the apparatus functions in a similar manner to the various form of diet apparatus described herein.

The wall of the stomach comprises inner layers called the mucosa, and the submucosa, which separate the muscular layer of the stomach from the contents of the stomach. For some applications, it is advantageous to minimize the extent to which the electrodes bring the contents of the stomach (which are corrosive and not necessarily completely sterile) out of the stomach chamber and into contact with the muscular layer of the stomach or the surrounding abdominal cavity. In order to protect the muscular layer of the stomach in this manner, in an embodiment, each electrode is enclosed in a clamshell cover (e.g., the cover of electrode implantation tool 300) that is adapted to penetrate the mucosal and submucosal layers of the stomach while in a closed position. Once the clamshell cover is suitably placed in or near the submucosal layer, the clamshell cover is opened by the operator of the endoscopic tool. Subsequently, the electrode is coupled to the muscular layer of the stomach using a placement rod, that may extend from the clamshell cover. The electrode is detached from the placement rod once the electrode is suitably placed. Multiple electrodes are typically placed in the wall of the stomach in this manner in the process of providing diet evaluation and/or regulation apparatus for a patient, as described herein.

An external charger 308 is typically in wireless communication with control unit 310, and may have some or all of the functionalities described hereinabove with respect to charger 200.

Figure 14A:
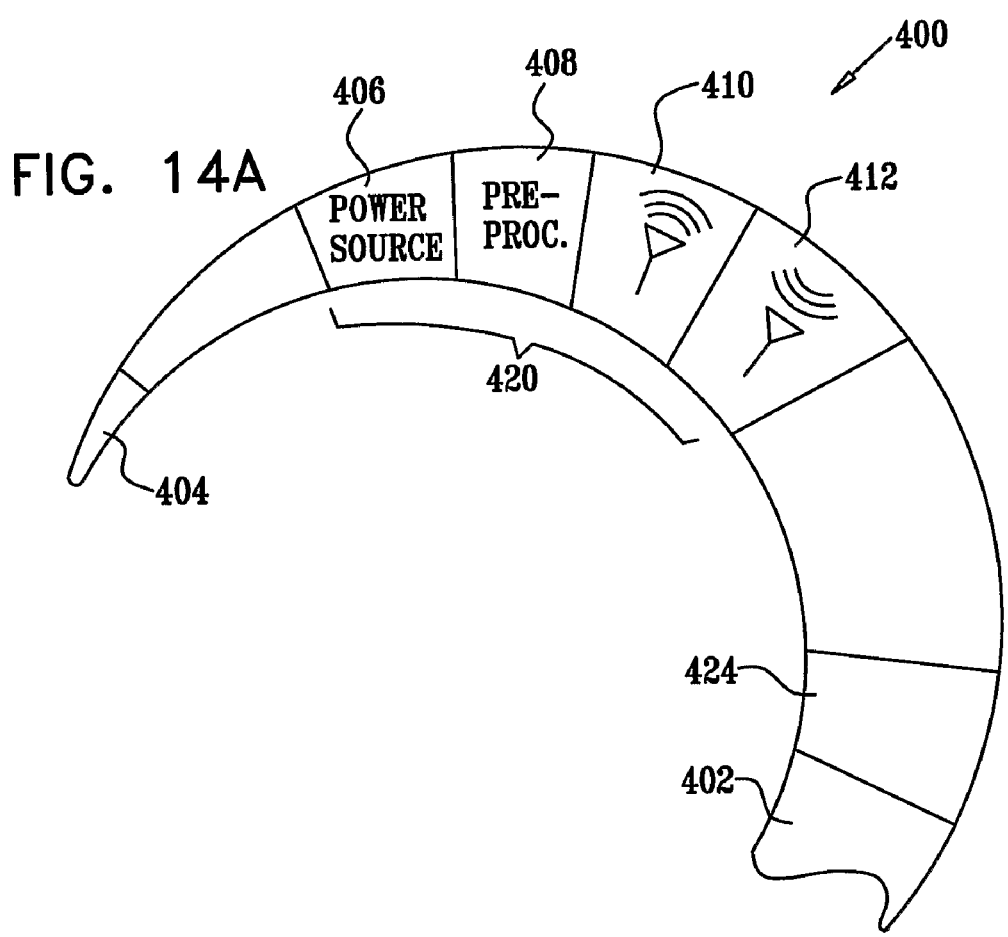
FIGS. 14A and 14B, are schematic illustrations of electrode mounts, in accordance with respective embodiments of the present invention.
Figure 14B:
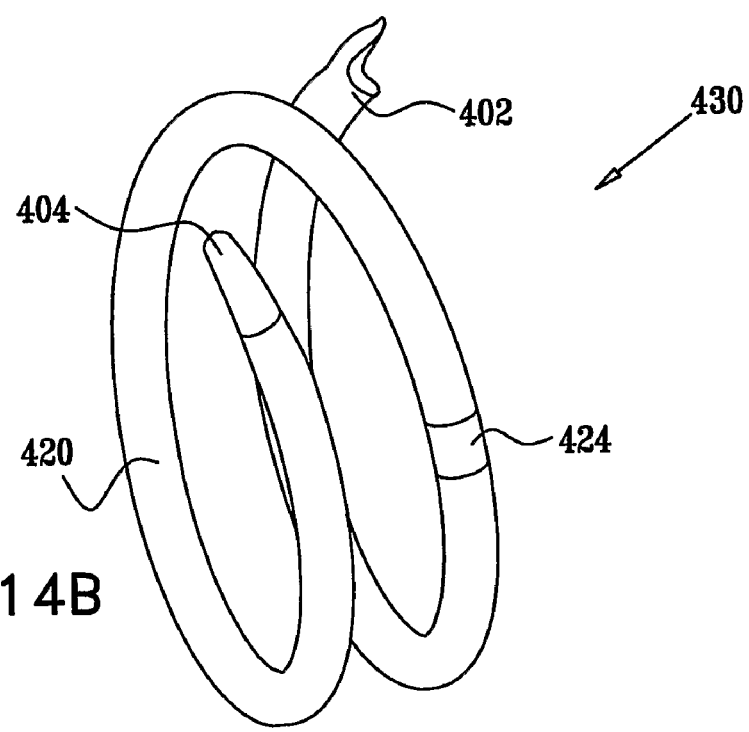

Reference is now made to FIGS. 14A and 14B, which are schematic illustrations of electrode mounts 400 and 430, in accordance with respective embodiments of the present invention. For some applications, at least some of the electrodes endoscopically implanted in the stomach wall serve as sensors of a state of the stomach. Such a sensor typically comprises a pair of needle, coil, or other electrodes 404, 424, which are adapted to be coupled to the stomach muscle. The electrodes may sense antral electrical activity, or fundic impedance, e.g., as described herein. Electrode mounts 400 and 430 typically comprise a controller portion 420, which typically comprises various subcomponents such as a modulator (e.g., a voltage-to-frequency converter) and a transmission coil 410, coupled to the modulator. Coil 410 transmits a sensor signal at a frequency set by the modulator, and this transmitted signal is detected by control unit 310. Typically, the control unit transmits a power signal towards the electrode mounts, and the power signal induces a current in a power coil 412 coupled to the electrodes. This current typically powers the operation of the modulator as well as the operation of transmission coil 410. For some applications, the current in power coil 412 also supports the operation of an analog or digital pre-processor 408 in the controller, prior to transmission of information to control unit 310. In an embodiment, a digital modulation protocol (e.g., FSK or a derivative thereof) is used.

For some embodiments of the present invention, some or all of electrodes 318 implanted on the stomach are wirelessly driven by control unit 310 to drive current into the stomach, e.g., using timings and amplitudes described herein or in the references incorporated herein by reference.

In an embodiment, electrode mounts 400 and 430 comprise a curved arrangement comprising electrodes 404 and 424 near or at either end, and controller 420 in the middle. The controller typically comprises some or all of the following: power coil 412, transmission coil 410, a modulator (e.g., a voltage-to-frequency converter), a demodulator (e.g., a frequency-to-voltage converter), an analog/digital (A/D) converter, a digital/analog (D/A) converter, digital or analog preprocessor 408, a rechargeable energy storage device (e.g., a rechargeable battery or a rechargeable capacitor) 406 and/or other circuitry useful for facilitating the operation of electrodes 318 on the stomach and wireless communication between the electrodes and control unit 310. A shaped end portion 402 of electrode mounts 400 and 430 typically prevents the electrode mount from slipping following implantation. End portion 402 may be at either or both ends of mounts 400 and 430, or may be absent if the mount is sufficiently stable following implantation.

In an embodiment, controller 420 comprises a force transducer (not shown), adapted to measure deflections of at least a portion of the curved arrangement, and to thereby facilitate a determination of local distension of the stomach. This determination of distension, in turn, serves as an indicator of eating. Typically, but not necessarily, the electrodes of the curved arrangement apply a signal to the stomach to inhibit eating. As appropriate, apparatus and techniques described with reference to FIGS. 14A and 14B may be useful with the apparatus and techniques described with reference to FIG. 13.

In an embodiment, the curved arrangement is shaped like a portion of a corkscrew (e.g., 150-270 degrees (FIG. 14A), 270-360 degrees, 360-540 degrees, 540-720 degrees (FIG. 14B), or greater than 720 degrees of a corkscrew). Typically, but not necessarily, the electrodes at either end of the curved arrangement are disposed around the corkscrew in generally opposing positions with respect to a longitudinal axis of the corkscrew, i.e., at 12 o'clock and at between 4 and 6 o'clock (e.g., at 12 o'clock and about 6 o'clock (FIG. 14A)). The electrodes themselves typically occupy some non-trivial length along the curved length of the corkscrew (e.g., 0.5 to 1.5 cm), and thus one of the electrodes may extend, for example, from 11 o'clock to 1 o'clock, while the other electrode extends from 5 o'clock to 7 o'clock. For some applications, non-opposing electrodes are utilized, e.g., electrodes located at 12 o'clock and 3 o'clock (FIG. 14B).

In an embodiment, the endoscope brings the corkscrew-shaped curved arrangement into contact with the mucosa of the stomach, typically such that that the axis of the corkscrew is generally perpendicular to a plane of the stomach at the point of contact. A small amount of pressure is applied to the stomach via the corkscrew-shaped arrangement, such that the wall of the stomach is stretched slightly. At this point, the endoscopist rotates the corkscrew-shaped arrangement, such that electrode 404 enters the mucosa, followed by controller 420 and electrode 424. For some applications, following this rotation, both electrodes are typically in contact with the muscular layer of the stomach, and not in substantial contact with the mucosa or the contents of the stomach.

In an embodiment, the curved arrangement comprises a corkscrew-shaped arrangement in which one electrode is disposed on the corkscrew between the controller and the other electrode (configuration not shown). The electrodes are still typically disposed opposite from each other, with respect to the axis of the corkscrew. Alternatively, the electrodes are closer to each other, e.g., 1-90 or 90-180 degrees apart. As described above, the corkscrew-shaped arrangement is pressed against the inner wall of the stomach. In this embodiment, however, the electrode mount is coupled to an implantation tool such that the controller is typically at the leading edge of the corkscrew as it is being rotated into the gastric wall. Alternatively, the controller enters the gastric wall after the two electrodes.

For some applications, controller 420 and both electrodes 404 and 424 reside within or almost entirely within the stomach muscle, after, implantation. Alternatively, when the controller is at the leading edge of the corkscrew, the corkscrew-shaped arrangement may be rotated until the controller protrudes from the gastric wall. For some applications, the controller remains in that position. For other applications, the corkscrew-shaped arrangement continues to be rotated until the controller leaves the stomach muscle, and sits outside of the serosal layer of the stomach.

Figure 15A:
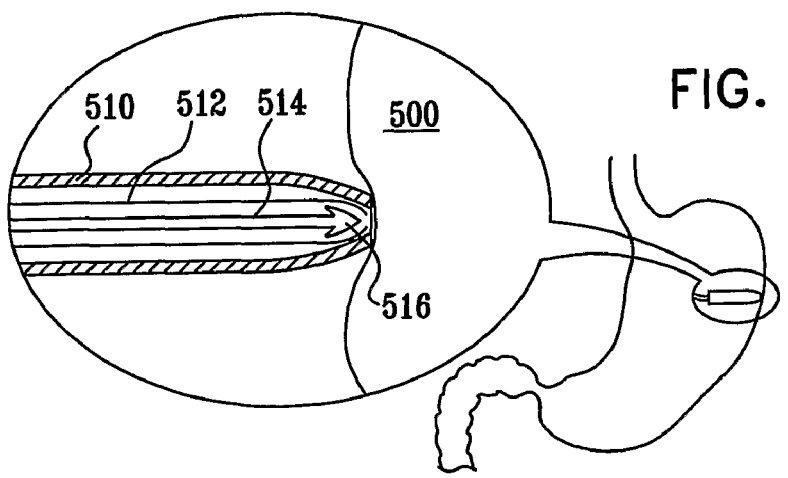
FIGS. 15A, 15B, and 15C, are schematic illustrations of an endoscopic electrode implantation procedure, in accordance with an embodiment of the present invention.
Figure 15B:
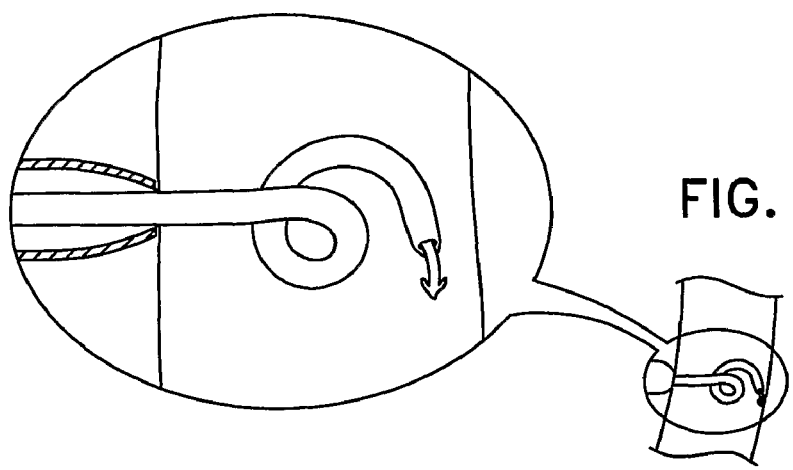
Figure 15C:
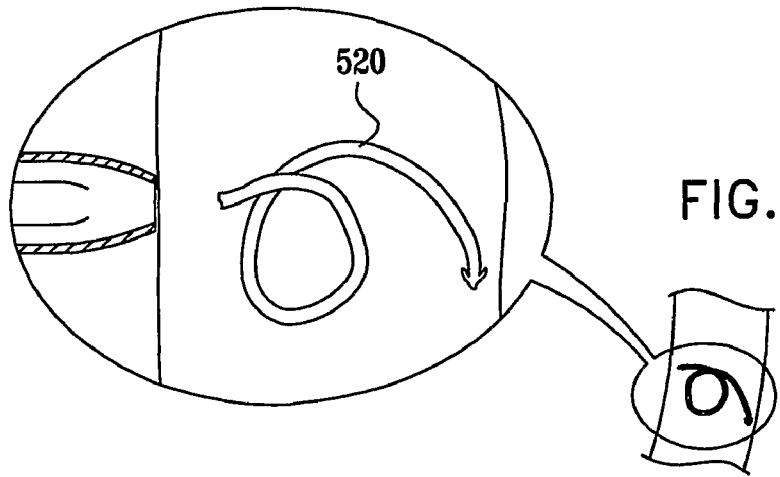

Reference is now made to FIGS. 15A, 15B, and 15C, which are schematic illustrations of an endoscopic electrode implantation procedure, in accordance with an embodiment of the present invention. In an embodiment, a curved arrangement 514 such as one of the arrangements described herein is flexible, and does not necessarily generally restore its shape after being bent. Curved arrangement 514 is inserted into a shape-defining catheter 512. The shape-defining catheter naturally assumes a curved shape (e.g., a corkscrew shape as described hereinabove), unless external forces prevent it from assuming this shape. Shape-defining catheter 512 is inserted into an endoscope 510, which maintains the shape-defining catheter in a generally straight configuration.

Typically, during a procedure, endoscope 510 brings shape-defining catheter 512 into contact with the mucosa of the stomach, and then presses the wall of the stomach so that the stomach will be taut at the contact site, and so that the axis of the endoscope will be generally perpendicular to the plane of the stomach at the contact site (FIG. 15A). Shape-defining catheter 512 is pushed out of the endoscope, punctures the mucosa, and enters the wall 500 of the stomach. While leaving the endoscope and entering the wall of the stomach, the shape-defining catheter assumes its curved shape (FIG. 15B). In this manner, shape-defining catheter 512 advances flexible curved arrangement 514 into the wall 500 of the stomach. At this point, shape-defining catheter 512 is typically removed, leaving curved arrangement 514 in contact with the stomach muscle 500, and in a corkscrew shape 520. For some applications, a hooking element 516 (e.g., a dull barb) at the distal end of the curved arrangement prevents the curved arrangement from being withdrawn from the muscle when the shape-defining catheter is withdrawn.

In an embodiment, shape-defining catheter 512 is dissolvable, typically but not necessarily after between about 10 minutes and about 2 hours in the body. In this case, the shape-defining catheter need not be removed following placement of the curved arrangement in contact with the stomach muscle. Alternatively, instead of using a discrete shape-defining catheter, the functionality associated therewith and described herein is attained by applying a dissolvable coating on curved arrangement 514. The coating is adapted to have the same general mechanical properties as those described with respect to shape-defining catheter 512. Suitable techniques for controlling the mechanical properties of a substance dissolvable in the gastrointestinal tract are known in the art. In some embodiments, the dissolvable substance comprises chitin, cellulose, a sugar, a polymer, and/or other known substances appropriate for dissolving in contact with body fluids.

In an embodiment, the flexibility of curved arrangement 514 after implantation facilitates a measurement of local distension of the stomach responsive to a change in shape of the curved arrangement. For example, a change in impedance of tissue between two electrodes on the curved arrangement may be used to indicate the extent of distension of the tissue, and to serve as a basis for a decision (by controller 420 and/or control unit 310) to apply a signal to the stomach to reduce further eating. The change in impedance may be due to a change in distance between the electrodes, a change in thickness of the tissue therebetween, and/or a change in another property of the tissue therebetween.

In an embodiment, a formable shape-defining catheter (not shown) is provided, which does not necessarily naturally assume a desired curved shape, as described hereinabove with respect to (preformed) shape-defining catheter 512. Instead, the formable shape-defining catheter rests within the endoscope without necessarily engendering substantial forces between the formable shape-defining catheter and the endoscope. In this embodiment, the formable shape-defining catheter has its curved shaped defined by a shape of a distal outlet of the endoscope, which in effect exudes the formable shape-defining catheter in a corkscrew or other desired shape. For example, the distal outlet may be located off of the axis of the endoscope and/or the distal outlet may have a characteristic axis thereof which is not parallel to the axis of the endoscope. Alternatively or additionally, one or more other elements described herein (e.g., the curved arrangement, or the dissolvable substance) are "formable," in this manner. Formable elements may comprise a metal (e.g., titanium), a polymer, and/or other materials.

FIG. 16 is a schematic illustration of a curved arrangement, in accordance with an embodiment of the present invention. In this embodiment, the curved arrangement is disposed around an endoscope 610 or other tool, and is spun off of the endoscope in order to cause implantation of the curved arrangement in stomach wall 500. In this embodiment, the curved arrangement typically has relatively high stiffness, as appropriate to maintain its shape during the insertion into stomach wall 500. Alternatively, the curved arrangement is flexible, but is surrounded by a shape-defining catheter like shape-defining catheter 512 or a dissolvable shape-defining catheter (as described hereinabove), or is coated with a dissolvable substance able to maintain its form during implantation.

For some applications, curved arrangements described herein with respect to two electrodes are provided instead with more electrodes, e.g., 4, 5, 20, 50, or 100 electrodes. FIG. 16, for example, shows a large number of electrodes 600 disposed along the length of the curved arrangement. Typically, after an initial period of calibration, a desired subset of these electrodes is used during regular operation. Optionally, electrodes 600 used for sensing are different from other electrodes 600 used for signal application. For some applications, the subsets of electrodes 600 are varied over time. In an embodiment, multiple adjacent electrodes 600 are activated in order to simulate a larger electrode.

For some applications, an advancement tool (not shown) attached to the endoscope advances (e.g., screws or pushes) the curved arrangement into the stomach wall. In an embodiment, the advancement tool is attached to the curved arrangement during the advancing, and is separated therefrom when the curved arrangement is no longer in contact with the mucosa layer of the stomach. Alternatively, the advancement tool is not attached to the curved arrangement, but instead articulates with or is lightly coupled to the curved arrangement. In this case, the advancement tool is retracted after the curved arrangement is no longer in contact with the mucosa layer of the stomach.

For some applications, multiple cartridges are provided within a single endoscope, and each cartridge comprises one or more electrodes to be implanted at a given site on the stomach. In an embodiment, all apparatus that is associated with any given cartridge is either (a) implanted on the stomach, or (b) dissolvable within the patient's body (e.g., in the stomach). In this manner, implantation of a plurality of electrodes at respective sites on the stomach does not necessarily utilize repeated insertions and withdrawals of electrodes and support tools through the endoscope.

FIGS. 17A, 17B, 17C, and 17D (not to scale) are schematic illustrations of respective stages in an endoscopic electrode implantation procedure, in accordance with an embodiment of the present invention. An endoscope 720 within the stomach pushes abdominal cavity apparatus comprising electrode apparatus comprising an insertion head 700 through the wall 500 of the stomach (FIG. 17A) into the abdominal cavity, outside of the stomach. Insertion head 700 rotates (FIG. 17B) around a hinge 710, either by activation of a release mechanism (e.g., a spring), or by force applied by the endoscopist. Electrodes 722 which may be coiled (as shown) or straight (configuration not shown) are released from the body of head 700 (FIG. 17B). Typically, but not necessarily, a release mechanism (e.g., a spring, not shown) is activated in order to cause electrodes 722 to be released from the body of head 700. FIG. 17C shows insertion head 700 being pulled towards stomach wall 500, typically by the endoscopist. FIG. 17D shows the final state of the electrodes, implanted in wall 500. For some applications, insertion head 700 remains attached to electrodes 722, and comprises a controller like controller 420.

FIGS. 18A, 18B, and 18C (not to scale) are schematic illustrations of respective stages in an endoscopic electrode implantation procedure, in accordance with another embodiment of the present invention. Except where specifically noted to the contrary, techniques described hereinabove with reference to FIGS. 17A, 17B, 17C, and 17D are typically applied with respect to FIGS. 18A, 18B, and 18C. Electrodes 724 located on the outside of insertion head 700 (FIG. 18A) are placed in contact with stomach wall 500 (FIG. 18B) due to rotation of insertion head 700 and force applied by the endoscopist to bring the insertion head closer to stomach wall 500. Subsequently, insertion head 700 is drawn to its final position against the stomach wall, and the electrodes are implanted in the wall.

For some applications (e.g., when the electrodes are needle electrodes), motion of insertion head 700 in and of itself is sufficient to place the electrodes in the wall. Alternatively, the electrodes are screwed into wall 500, typically but not necessarily during movement of insertion head 70Q towards wall 500. This screwing of the electrodes may be achieved by the endoscopist manipulating endoscopic controls 337 (FIG. 13). Alternatively, the screwing may comprise activation of a release mechanism, for example respective springs in insertion head 700, that causes the electrodes to be screwed into wall 500.

FIGS. 19A, 19B, 19C, and 19D are pictorial illustrations of respective stages in an endoscopic electrode implantation procedure, in accordance with another embodiment of the present invention. A controller 800 coupled to two electrodes 802 is pushed through the wall of the stomach, until it is outside of the stomach. The controller and electrodes may, for example, be rolled or folded and contained within an insertion head. In an embodiment, the insertion head punctures the stomach and then dissolves or is separated from the controller and electrodes, in order to arrive at the configuration shown in FIG. 19A.

Figure 19A:
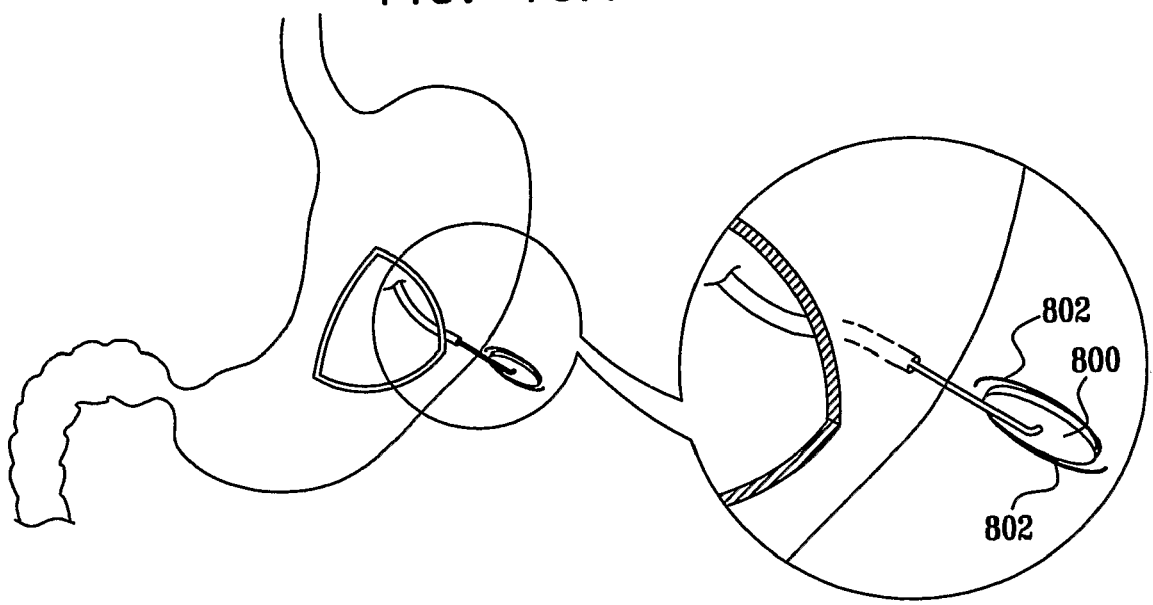
FIGS. 19A, 19B, 19C, and 19D are pictorial illustrations of respective stages in an endoscopic electrode implantation procedure, in accordance with yet another embodiment of the present invention.
Figure 19B:
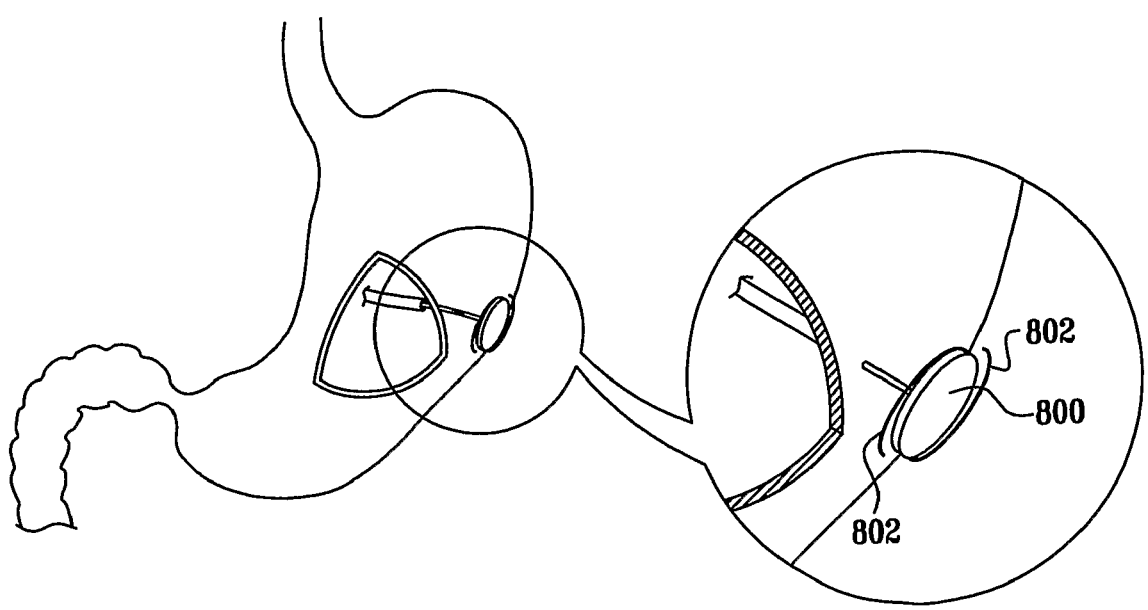
Figure 19C:
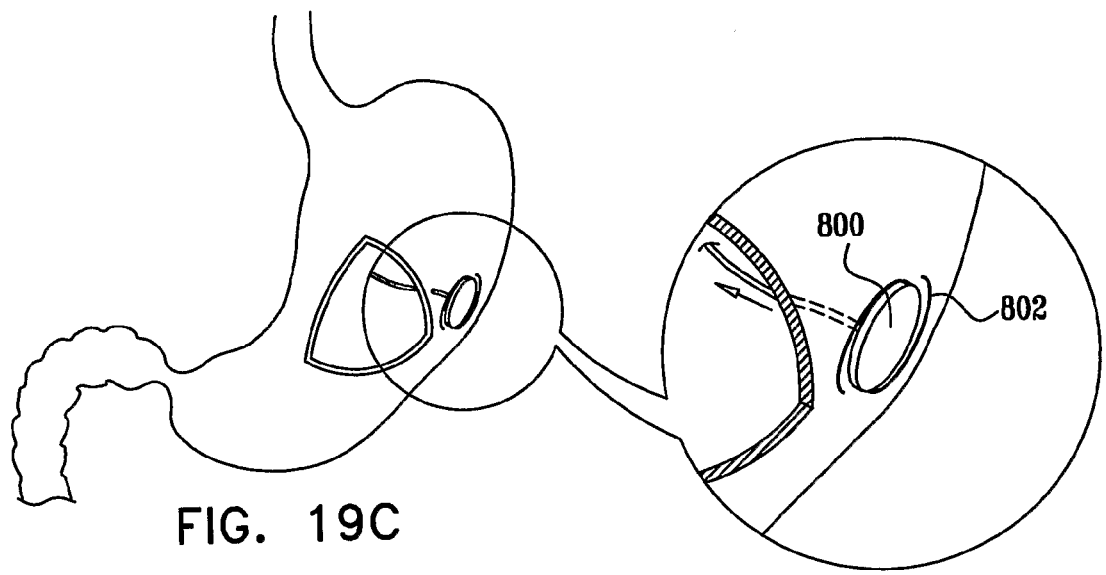
Figure 19D:
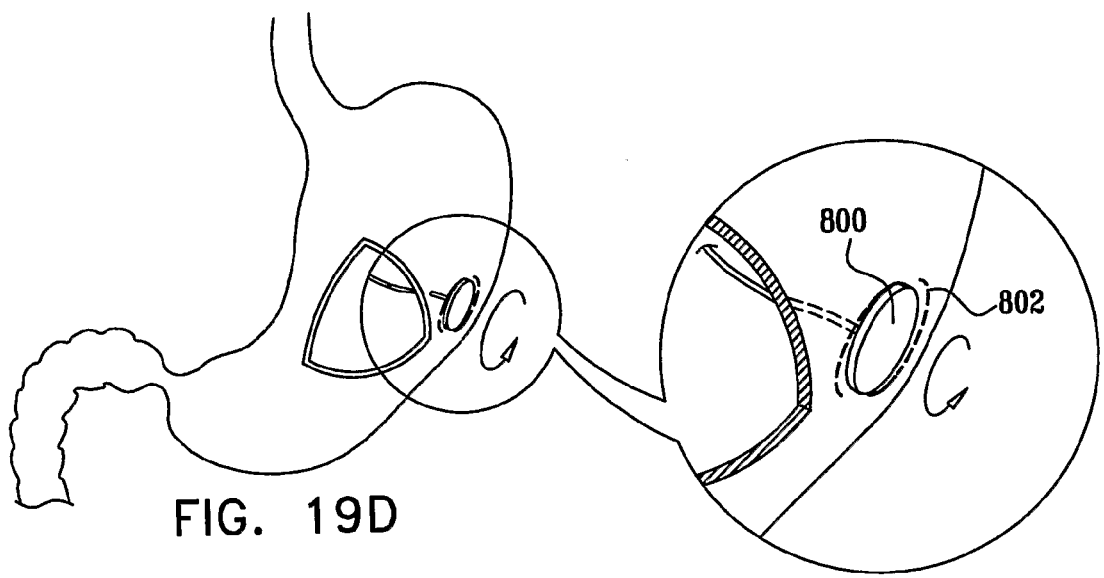

Controller 800 is subsequently rotated, in order to arrive at the configuration shown in FIG. 19B. In FIG. 19C, the controller is pulled towards the stomach. In FIG. 19D, the controller is rotated (around a different axis), in order to insert electrodes 802 into the stomach wall. Subsequently, electrodes 802 and controller 800 operate in a manner similar to that described hereinabove, e.g., with respect to controller 420 and electrodes 404 and 424.

Figure 20:
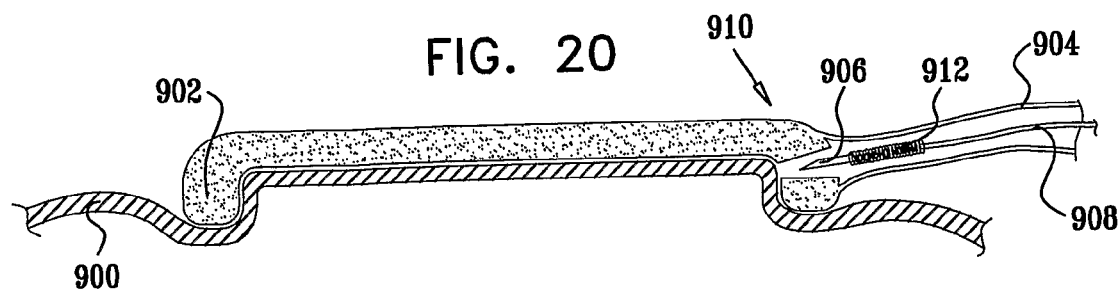
FIG. 20 is a schematic illustration of endoscopic gastric apparatus, in accordance with an embodiment of the present invention.

FIG. 20 is a schematic illustration of endoscopic gastric apparatus 910, in accordance with an embodiment of the present invention. Apparatus 910 comprises a flexible cap 902 that is coupled to conventional (or custom-made) transluminal apparatus such as an endoscope 904. The cap comprises a coupling mechanism that couples the cap to the wall 900 of the stomach, e.g., to the gastric inner wall. The coupling mechanism typically comprises a suction device. For example, cap 902 may be shaped to define one or more slots that allow suction to be applied to the gastric inner wall in order to maintain contact between cap 902 and wall 900.

A guiding needle 906 coupled to an electrode 912 is initially disposed within endoscope 904. When cap 902 is coupled to stomach wall 900, the needle is advanced from the endoscope and punctures wall 900. Electrode 912 is then placed within the gastric wall, and typically decoupled from needle 906. Needle 906 is then typically withdrawn into endoscope 904. Leads 908 are coupled via wires or wirelessly to a control unit.

In an embodiment, endoscope 908 comprises a multi-luminal endoscope, that allows the use of several tools (e.g., camera, clip-applicator, suturing device, endoscopic ultrasound) at generally the same time. For some applications, one of the lumens allows the injection of saline into the submucosa or into the gastric muscle, in order to allow passage of wires under the mucosa or in order to thicken the muscle and thereby ease the insertion of the needle. Alternatively or additionally, this lumen is used for the local injection of drugs.

In an embodiment, an applicator (which may look and/or function like cap 902) is attached to the tip of an endoscope. The applicator typically but not necessarily comprises a frame made of plastic or another material. In an embodiment, there is simultaneous implantation of two electrodes using a "two-railed" applicator, i.e., one electrode is implanted through or along one rail, and the other electrode is implanted through or along another rail. As appropriate, the electrodes may be implanted using the same technique as that described for electrode 912.

In an embodiment, a physical portion of the endoscope (e.g., the tip of the endoscope) applies pressure to the greater curvature of the stomach. Suction is applied via a lumen of the endoscope, such that the applicator applies suction to the wall of the stomach and holds the stomach in contact therewith. An endoscopic element, e.g., a second lumen in the endoscope or a second endoscope, applies positive pressure to the stomach in order to inflate the stomach and cause tight contact of the stomach with the anterior abdominal wall.

Abdominal cavity apparatus comprising a skin-puncturing needle is passed through the skin, through the abdomen, and then through the gastric wall, until the skin-puncturing needle is in contact with or otherwise coupled to the applicator. Through this skin-puncturing needle, electrode leads are inserted, e.g., using a straight or curved implantation needle. The implantation needle is passed through a series of one or more holes and/or conduits in the applicator body, in order to align the implantation needle for its insertion through the gastric tissue in contact with the applicator. This technique facilitates contact between the electrode leads which are implanted on the stomach (as described) and a control unit which is typically implanted subcutaneously.

For some applications, techniques such as (but not limited to) those described with reference to FIG. 20 are practiced in combination with techniques described in the above-referenced US Patent Application Publication 2006/0089690 to Gerber, which is incorporated herein by reference, or in combination with other patent references cited in the present patent application.

It is noted that although some embodiments of the present invention are described hereinabove with respect to endoscopic implantation of electrodes on the stomach, the scope of the present invention includes implantation of electrodes, using similar techniques, mutatis mutandis, on other tissue, e.g., another site in the gastrointestinal tract such as the esophagus, the small intestine, or the colon. Similarly, the scope of the present invention includes applying techniques described herein to non-gastrointestinal tract lumens and cavities, such as arteries, veins, and chambers of the heart, mutatis mutandis.

The scope of the present invention includes embodiments described in U.S. Provisional Patent Application 60/758,937 to Levi et al., filed Jan. 12, 2006, entitled, "Electrode assemblies, tools, and methods for gastric wall implantation," which is assigned to the assignee of the present patent application and is incorporated herein by reference. Additionally, for some applications, implantation techniques described in the '937 application are used in combination with techniques described herein, in order to facilitate gastric electrode implantation.

The scope of the present invention includes embodiments described in the following applications, which are incorporated herein by reference. In an embodiment, techniques and apparatus (e.g., glucose and insulin reduction) described in one or more of the following applications are combined with techniques and apparatus described herein:

A PCT application to Harel et al., filed Mar. 18, 2005, entitled, "Gastrointestinal methods and apparatus for use in treating disorders and controlling blood sugar,"

U.S. patent application Ser. No. 10/804,560, filed Mar. 18, 2004,

U.S. Provisional Application No. 60/488,964, filed on Jul. 21, 2003,

PCT/IL2004/000797, filed Sep. 5, 2004,

PCT/IL2004/000551 to Glasberg et al., filed Jun. 20, 2004,

U.S. Provisional Patent Application 60/480,208, filed Jun. 20, 2003, entitled, "Hepatic device for treatment, eating detection, and glucose level detection,"

U.S. Provisional Patent Application 60/488,964, filed Jul. 21, 2003, entitled, "Gastrointestinal methods and apparatus for use in treating disorders and controlling blood sugar,"

PCT/IL2004/000664 to Ben Haim et al., filed Jul. 21, 2004,

PCT/IL2004/000550, filed Jun. 20, 2004,

U.S. Provisional Patent Application 60/480,205, filed Jun. 20, 2003, entitled, "Gastrointestinal methods and apparatus for use in treating disorders,"

U.S. Provisional Patent Application 60/480,208, filed Jun. 20, 2003, entitled, "Hepatic device for treatment, eating detection, and glucose level detection,"

a US national phase application of PCT Application No. PCT/IL03/00736, which was filed on Sep. 4, 2003, U.S. application Ser. No. 10/237,263, filed on Sep. 5, 2002, PCT Application PCT/IL00/00566, filed on Sep. 13, 2000, now published as WO 01/66183, which designates the US, U.S. application Ser. No. 09/914,889, filed on Jan. 24, 2002, which is the US national phase application of PCT Application PCT/IL00/00132, filed on Mar. 5, 2000, which designates the US, U.S. Provisional Application 60/123,532, filed on Mar. 5, 1999, and a US national phase application of PCT Application PCT/IL02/00856, U.S. Provisional Patent Application No. 60/334,017, filed Nov. 29, 2001, entitled, "In situ sensing of pancreatic electrical activity,"

PCT Patent Application PCT/IL01/00501, filed May 30, 2001, entitled, "Electropancreatography,"

U.S. Provisional Patent Application 60/208,157, filed May 31, 2000, entitled, "Electrical activity sensor for the whole pancreas,"

a US provisional patent application to Ben-Haim et al., filed Feb. 17, 2005, entitled, "Charger with data transfer capabilities,"

a US provisional patent application to Kliger et al., filed Aug. 18, 2004, entitled, "Monitoring, analysis, and regulation of eating habits," and PCT Publication WO 99/03533, and its US national phase application.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
    passing an abdominal cavity apparatus into a lumen of a stomach of a patient, the abdominal cavity apparatus including a controller, and at least one electrode that is electrically coupled to the controller;
    pushing the controller through a wall of the stomach to an extra-gastric site within an abdominal cavity of the patient until no portion of the controller is within the lumen of the stomach;
    thereafter, moving the controller in a manner that places the at least one electrode in contact with the stomach wall; and
    leaving the at least one electrode in contact with the stomach wall, and the controller at the extra-gastric site.

2. The method according to claim 1, wherein passing the abdominal cavity apparatus into the lumen of the stomach comprises passing, into the lumen of the stomach, an endoscope to which the abdominal cavity apparatus is coupled.

3. The method according to claim 2, wherein moving the controller comprises using the endoscope to the pull the controller toward the wall of the stomach.

4. The method according to claim 1, wherein the electrode apparatus includes at least one needle electrode, and wherein leaving the electrode comprises leaving the needle electrode in the stomach wall.

5. The method according to claim 1,
    wherein the abdominal cavity apparatus further includes an insertion head, which includes the controller,
    wherein pushing the controller comprises pushing the insertion head through the wall of the stomach to the extra-gastric site until no portion of the insertion head is within the lumen of the stomach,
    wherein moving the controller comprises moving the insertion head in the manner that place the at least one electrode in contact with the stomach wall, and
    wherein leaving the controller comprises leaving the insertion head at the extra-gastric site.

6. The method according to claim 5, wherein the at least one electrode is initially positioned within the insertion head, and further comprising releasing the at least one electrode from the insertion head for placement in contact with the wall of the stomach.

7. The method according to claim 5, wherein moving the insertion head comprises rotating the insertion head in order to bring the at least one electrode in contact with the wall of the stomach.

8. The method according to claim 1, wherein moving the controller comprises rotating the controller in order to insert the at least one electrode into the wall of the stomach.

9. The method according to claim 1, wherein pushing comprises pushing the controller through the wall of the stomach to the extra-gastric site until the controller is entirely outside the stomach.

10. The method according to claim 1, wherein moving the controller comprises moving the controller in a manner that places the at least one electrode in the stomach wall, and wherein leaving the at least one electrode comprises leaving the at least one electrode in the stomach wall.

11. The method according to claim 10, wherein the stomach wall includes a muscular layer, and wherein leaving the at least one electrode comprises leaving the at least one electrode in the muscular layer.

12. The method according to claim 10, wherein the stomach wall includes a submucosal layer, and wherein leaving the at least one electrode comprises leaving the at least one electrode in the submucosal layer.

* * * * *